(12) United States Patent
Grammenos et al.

(10) Patent No.: US 9,763,448 B2
(45) Date of Patent: Sep. 19, 2017

(54) FUNGICIDAL MIXTURES I COMPRISING STROBILURIN-TYPE FUNGICIDES

(71) Applicant: BASF SE, Ludwigshafen (DE)

(72) Inventors: Wassilios Grammenos, Ludwigshafen (DE); Sebastian Georgios Rohrer, Ketsch (DE); Joachim Rheinheimer, Ludwigshafen (DE); Christian Winter, Ludwigshafen (DE); Ana Escribano Cuesta, Mannheim (DE); Egon Haden, Speyer (DE); Jurith Montag, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/897,935

(22) PCT Filed: Jun. 10, 2014

(86) PCT No.: PCT/EP2014/061959
§ 371 (c)(1),
(2) Date: Dec. 11, 2015

(87) PCT Pub. No.: WO2014/202421
PCT Pub. Date: Dec. 24, 2014

(65) Prior Publication Data
US 2016/0135459 A1    May 19, 2016

(30) Foreign Application Priority Data

Jun. 18, 2013 (EP) ..................... 13172461
Aug. 27, 2013 (EP) ..................... 13181864

(51) Int. Cl.
*A01N 43/56* (2006.01)
*A01N 43/653* (2006.01)

(52) U.S. Cl.
CPC ........... *A01N 43/56* (2013.01); *A01N 43/653* (2013.01)

(58) Field of Classification Search
CPC combination set(s) only.
See application file for complete search history.

(56) References Cited

U.S. PATENT DOCUMENTS 9,271,501 B2 * 3/2016 Rheinheimer ......... A01N 37/50

FOREIGN PATENT DOCUMENTS

| EP | 2 517 562 | 10/2012 |
|----|-----------|---------|
| WO | WO 2009/090181 | 7/2009 |
| WO | WO 2013/007767 | 1/2013 |
| WO | WO 2013/010862 | 1/2013 |
| WO | WO 2013/024075 | 2/2013 |
| WO | WO 2013/024076 | 2/2013 |
| WO | WO 2013/024077 | 2/2013 |
| WO | WO 2013/024080 | 2/2013 |
| WO | WO 2013/024083 | 2/2013 |
| WO | WO 2013/092224 | 6/2013 |
| WO | WO 2014/095932 | 6/2014 |
| WO | WO 2014/095994 | 6/2014 |

OTHER PUBLICATIONS

International Search Report dated Aug. 19, 2014, prepared in International Application No. PCT/EP2014/061959.
International Preliminary Report on Patentability dated Dec. 22, 2015, prepared in International Application No. PCT/EP2014/061959.

* cited by examiner

Primary Examiner — John Pak
(74) Attorney, Agent, or Firm — Brinks Gilson & Lione

(57) ABSTRACT

The present invention relates to fungicidal mixtures, comprising at least one fungicidally active strobilurin-type compound I and at least one fungicidally active compound or biopesticide II as defined in the description, and to compositions comprising these mixtures.

15 Claims, No Drawings

FUNGICIDAL MIXTURES I COMPRISING STROBILURIN-TYPE FUNGICIDES

This application is a National Stage application of International Application No. PCT/EP2014/061959 filed Jun. 10, 2014. This application also claims priority under 35 U.S.C. §119 to European Patent Application No. 13172461.9, filed Jun. 18, 2013, and European Patent Application No. 13181864.3, filed Aug. 27, 2013.

The present invention relates to mixtures comprising, as active components
1) at least one compound of formula I

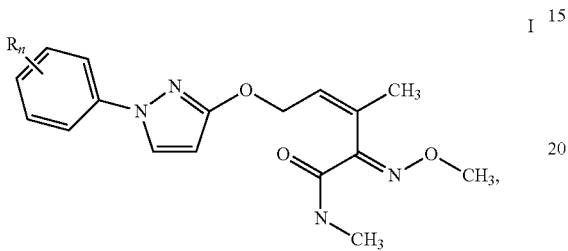

wherein
n is an integer and is 0, 1, 2, 3, 4 or 5; and
R, which may be the same or different to any other R, is halogen, hydroxyl, carboxyl, $C_1$-$C_4$-alkyl, $C_2$-$C_4$-alkenyl, $C_2$-$C_8$-alkynyl, $C_1$-$C_4$-haloalkyl, $C_1$-$C_4$-alkoxy, $C_1$-$C_4$-haloalkoxy, $C_1$-$C_4$-alkylsulfanyl, $C_1$-$C_4$-haloalkylsulfanyl, $C_1$-$C_6$-alkoxyimino-$C_1$-$C_4$-alkyl, $C_2$-$C_6$-alkenyloxyimino-$C_1$-$C_4$-alkyl, $C_2$-$C_6$-alkynyloxyimino-$C_1$-$C_4$-alkyl, $C_1$-$C_4$-alkoxyimino-$C_1$-$C_4$-alkyl, $C_1$-$C_6$-alkoxyimino-, $C_2$-$C_6$-alkenyloxyimino-, $C_2$-$C_6$-alkynyloxyimino-, $C_2$-$C_6$-haloalkenyloxyimino-, $C_3$-$C_6$-cycloalkyl, $C_3$-$C_6$-cycloalkenyl, phenyl or a 5-membered saturated, partially unsaturated or aromatic heterocyclyl which, in addition to carbon atoms, contains one to three heteroatoms from the group consisting of N, O and S as ring members; wherein the aforementioned cyclic groups R are attached via a direct bond, an oxygen or sulfur atom and where the aliphatic or cyclic groups $R^c$ for their part may carry 1, 2, 3 or up to the maximum possible number of identical or different groups $R^a$:
$R^a$, which may be the same or different to any other $R^a$, is halogen, $C_1$-$C_4$-alkyl or $C_1$-$C_4$-haloalkyl;
and
2) at least one fungicidally active compound or biopesticide II selected from groups A) to I):
A) C14 demethylase inhibitors selected from:
2-[2-chloro-4-(4-chlorophenoxy)phenyl]-1-(1,2,4-triazol-1-yl)pentan-2-ol (II-1), 1-[4-(4-chlorophenoxy)-2-(trifluoromethyl)phenyl]-1-cyclopropyl-2-(1,2,4-triazol-1-yl)ethanol (II-2), 2-[4-(4-chlorophenoxy)-2-(trifluoromethyl)phenyl]-1-(1,2,4-triazol-1-yl)butan-2-ol (II-3), 2-[2-chloro-4-(4-chlorophenoxy)phenyl]-1-(1,2,4-triazol-1-yl)butan-2-ol (II-4), 2-[4-(4-chlorophenoxy)-2-(trifluoromethyl)phenyl]-3-methyl-1-(1,2,4-triazol-1-yl)butan-2-ol (II-5), 2-[4-(4-chlorophenoxy)-2-(trifluoromethyl)phenyl]-1-(1,2,4-triazol-1-yl)propan-2-ol (II-6), 2-[2-chloro-4-(4-chlorophenoxy)phenyl]-3-methyl-1-(1,2,4-triazol-1-yl)butan-2-ol (II-7), 2-[4-(4-chlorophenoxy)-2-(trifluoromethyl)phenyl]-1-(1,2,4-triazol-1-yl)pentan-2-ol (II-8), 2-[4-(4-fluorophenoxy)-2-(trifluoromethyl)phenyl]-1-(1,2,4-triazol-1-yl)propan-2-ol (II-9), 3-(4-chloro-2-fluoro-phenyl)-5-(2,4-difluorophenyl)isoxazol-4-yl]-(3-pyridyl)methanol (II-10); 2-[2-chloro-4-(4-chlorophenoxy)phenyl]-1-(1,2,4-triazol-1-yl)pent-3-yn-2-ol (II-56); 1-[2-chloro-4-(4-chlorophenoxy)phenyl]-1-cyclopropyl-2-(1,2,4-triazol-1-yl)ethanol (II-57); 1-[2-[2-chloro-4-(4-chlorophenoxy)phenyl]-2-methoxy-pent-3-ynyl]-1,2,4-triazole (II-58); 1-[2-[2-chloro-4-(4-chlorophenoxy)phenyl]-2-cyclopropyl-2-methoxy-ethyl]-1,2,4-triazole (II-59); 1-[2-[4-(4-chlorophenoxy)-2-(trifluoromethyl)phenyl]-2-methoxy-propyl]-1,2,4-triazole (II-60); 2-[2-chloro-4-(4-chlorophenoxy)phenyl]-3,3-dimethyl-1-(1,2,4-triazol-1-yl)butan-2-ol (II-61); 1-[2-[4-(4-chlorophenoxy)-2-(trifluoromethyl)phenyl]-2-cyclopropyl-2-methoxy-ethyl]-1,2,4-triazole (II-62); 1-[2-[2-chloro-4-(4-chlorophenoxy)phenyl]-2-methoxy-3,3-dimethyl-butyl]-1,2,4-triazole (II-63); 1-[2-[4-(4-chlorophenoxy)-2-(trifluoromethyl)phenyl]-2-methoxy-butyl]1,2,4-triazole (II-64); 2-[4-(4-chlorophenoxy)-2-(trifluoromethyl)phenyl]-1-(1,2,4-triazol-1-yl)pent-3-yn-2-ol (II-65); 1-[2-[4-(4-chlorophenoxy)-2-(trifluoromethyl)phenyl]-2-methoxy-pent-3-ynyl]-1,2,4-triazole (II-66); 2-[4-(4-chlorophenoxy)-2-(trifluoromethyl)phenyl]-1-(1,2,4-triazol-1-yl)but-3-yn-2-ol (II-67); 2-[2-chloro-4-(4-chlorophenoxy)phenyl]-1-(1,2,4-triazol-1-yl)propan-2-ol (II-68); 2-[2-chloro-4-(4-fluorophenoxy)phenyl]-1-(1,2,4-triazol-1-yl)propan-2-ol (II-69); 1-[2-[2-chloro-4-(4-chlorophenoxy)phenyl]-2-methoxy-propyl]-1,2,4-triazole (II-70); 1-[2-[2-chloro-4-(4-chlorophenoxy)phenyl]-2-methoxy-butyl]-1,2,4-triazole (II-71); 1-[2-[2-chloro-4-(4-chlorophenoxy)phenyl]-2-methoxy-pentyl]-1,2,4-triazole (II-72); 2-[2-chloro-4-(4-chlorophenoxy)phenyl]-1,1,1-trifluoro-3-(1,2,4-triazol-1-yl)propan-2-ol (II-73); 2-[2-chloro-4-(4-chlorophenoxy)phenyl]-3-fluoro-1-(1,2,4-triazol-1-yl)butan-2-ol hydrochloride (II-74); 2-[2-chloro-4-(4-chlorophenoxy)phenyl]-1-(1,2,4-triazol-1-yl)pent-4-yn-2-ol (II-75); 2-[2-chloro-4-(4-chlorophenoxy)phenyl]-1-methoxy-3-(1,2,4-triazol-1-yl)propan-2-ol (II-76); 2-[2-chloro-4-(4-fluorophenoxy)phenyl]-1-methoxy-3-(1,2,4-triazol-1-yl)propan-2-ol (II-77);
B) Inhibitors of complex II selected from:
3-(difluoromethyl)-1-methyl-N-(1,1,3-trimethylindan-4-yl)pyrazole-4-carboxamide (II-11), 3-(trifluoromethyl)-1-methyl-N-(1,1,3-trimethylindan-4-yl)pyrazole-4-carboxamide (II-12), 1,3-dimethyl-N-(1,1,3-trimethylindan-4-yl)pyrazole-4-carboxamide (II-13), 3-(trifluoromethyl)-1,5-dimethyl-N-(1,1,3-trimethylindan-4-yl)pyrazole-4-carboxamide (II-14), 1,3,5-trimethyl-N-(1,1,3-trimethylindan-4-yl)pyrazole-4-carboxamide (II-15), N-(7-fluoro-1,1,3-trimethyl-indan-4-yl)-1,3-dimethyl-pyrazole-4-carboxamide (II-16), N-[2-(2,4-dichlorophenyl)-2-methoxy-1-methyl-ethyl]-3-(difluoromethyl)-1-methyl-pyrazole-4-carboxamide (II-17);
C) compounds with unknown mode of action selected from:
2,6-dimethyl-1H,5H-[1,4]dithiino[2,3-c:5,6-c']dipyrrole-1,3,5,7(2H,6H)-tetraone (II-18), ethyl(Z)-3-amino-2-cyano-3-phenyl-prop-2-enoate (II-19), tert-butyl N-[6-[[(Z)-[(1-methyltetrazol-5-yl)-phenylmethylene]amino]oxymethyl]-2-pyridyl]carbamate (II-20), pentyl N-[6-[[(Z)-[(1-methyltetrazol-5-yl)-phenyl-methylene]amino]oxymethyl]-2-pyridyl]carbamate (II-21), 2-[2-[(7,8-difluoro-2-methyl-3-quinolyl)oxy]-6-fluoro-phenyl]propan-2-ol (II-22), 2-[2-fluoro-6-[(8-fluoro-2-methyl-3-quinolyl)oxy]phenyl]propan-2-ol (II-23), 3-(5-fluoro-3,3,4,4-tetramethyl-3,4-dihydroisoquinolin-1-yl)quinolone (II-24), 3-(4,4-difluoro-3,3-dimethyl-3,4-dihydroisoquinolin-1-yl)quinoline (II-25), 3-(4,4,5-trifluoro-3,3-dimethyl-3,4-dihydroisoquinolin-1-yl)quinolone (II-26);

D) Microbial pesticides with fungicidal, bactericidal, viricidal and/or plant defense activator activity selected from:

Bacillus altudinis, Bacillus amyloliquefaciens, Bacillus amyloliquefaciens ssp. plantarum MBI 600 (II-27), B. amyloliquefaciens ssp. plantarum D747, B. megaterium, B. mojavensis (II-28), B. mycoides, B. pumilus INR-7 (II-29), B. pumilus GHA 180, B. simplex (II-30), B. solisalsi (II-31), Bacillus subtilis, Burkholderia sp., Clavibacter michiganensis (bacteriophages) (II-32), Gliocladium roseum (II-33), Microsphaeropsis ochracea, Muscodor albus, Paenibacillus alvei, Paenibacillus polymyxa (II-34), Pantoea agglomerans (II-35), Pantoea vagans, Penicillium bilaiae, Pseudomonas sp., Pseudomonas chloraphis, P. fluorescens, Sphaerodes mycoparasitica (II-36), Streptomyces lydicus (II-37), S. violaceusniger (II-38), Trichoderma fertile JM41R (II-39), Typhula phacorrhiza (II-40), Verticillium dahlia (II-42), zucchini yellow mosaic virus (avirulent strain);

E) Biochemical pesticides with fungicidal, bactericidal, viricidal and/or plant defense activator activity selected from:

harpin protein, laminarin, jasmonic acid (II-43) or salts or derivatives thereof, laminarin, Menhaden fish oil, natamycin, Plum pox virus coat protein, potassium or sodium bicarbonate, salicylic acid, tea tree oil;

F) Microbial pesticides with insecticidal, acaricidal, molluscidal and/or nematicidal activity selected from:

Agrobacterium radiobacter, Bacillus cereus, Bacillus firmus (II-44), B. thuringiensis ssp. israelensis, B. t. ssp. galleriae, B. t. ssp. kurstaki, Beauveria bassiana (II-45), Beauveria brongniartii, Burkholderia sp., Chromobacterium subtsugae, Cydia pomonella granulosis virus, Isaria fumosorosea, Lecanicillium longisporum, L. muscarium (formerly Verticillium lecanii), Metarhizium anisopliae (II-46), M. anisopliae var. anisopliae, M. anisopliae var. acridum, Paecilomyces fumosoroseus, P. lilacinus, Paenibacillus popilliae, Pasteuria spp., P. nishizawae, P. reneformis, P. thornea, P. usagae, Pseudomonas fluorescens, Pseudomonas putida, Steinernema feltiae, Steinernema kraussei, Streptomces galbus, Streptomyces microflavus;

G) Biochemical pesticides with insecticidal, acaricidal, molluscidal, pheromone and/or nematicidal activity selected from:

L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, R-1-octen-3-ol, pentatermanone, potassium silicate, sorbitol actanoate, (E,Z,Z)-3,8,11-tetradecatrienyl acetate, (Z,E)-9,12-tetradecadien-1-yl acetate, Z-7-tetradecen-2-one, Z-9-tetradecen-1-yl acetate, Z-11-tetradecenal, Z-11-tetradecen-1-ol, Acacia negra extract, extract of grapefruit seeds and pulp, extract of Chenopodium ambrosiodae, Catnip oil, Neem oil, Quillay extract (II-47), Tagetes oil;

H) Microbial pesticides with plant stress reducing, plant growth regulator, plant growth promoting and/or yield enhancing activity selected from:

Azospirillum amazonense, A. brasilense (II-48), A. lipoferum, A. irakense, A. halopraeferens, Bradyrhizobium sp. (II-49), B. japonicum (II-50), B. elkanii, B. lupini, B. liaoningense, Delftia acidovorans, Glomus intraradices, Mesorhizobium sp. (II-51), M. ciceri, M. huakii, M. loti, Paenibacillus alvei, Penicillium bilaiae (II-52), Rhizobium leguminosarum bv. phaseoli (II-53), R. l. trifolii, R. l. bv. viciae (II-54), R. tropici, Sinorhizobium meliloti (II-55);

I) Biochemical pesticides with plant stress reducing, plant growth regulator and/or plant yield enhancing activity selected from:

abscisic acid, aluminium silicate (kaolin), 3-decen-2-one, homobrassinolide, humates, indole-3-acetic acid, lysophosphatidyl ethanlamine, polymeric polyhydroxy acid, Ascophyllum nodosum (Norwegian kelp, Brown kelp) extract and Ecklonia maxima (kelp) extract.

Compounds I and their preparation and their use as fungicidally active compounds have been described in WO 2013/092224.

According to one embodiment of the invention, n is 1, 2 or 3 in formula I.

According to another embodiment, R is halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfanyl, $C_1$-$C_4$-haloalkylsulfanyl or $C_3$-$C_6$-cycloalkyl in formula I.

According to one embodiment of the invention, compounds of formula I are selected from (Z,2E)-5-[1-(4-chlorophenyl)pyrazol-3-yl]oxy-2-methoxyimino-N,3-dimethyl-pent-3-enamide (I-1), (Z,2E)-5-[1-(2,4-difluorophenyl)pyrazol-3-yl]oxy-2-methoxyimino-N,3-dimethyl-pent-3-enamide (I-2), (Z,2E)-5-[1-(2,4-dichlorophenyl)pyrazol-3-yl]oxy-2-methoxyimino-N,3-dimethyl-pent-3-enamide (I-3), (Z,2E)-5-[1-(2-chloro-4-methyl-phenyl)pyrazol-3-yl]oxy-2-methoxyimino-N,3-dimethyl-pent-3-enamide (I-4), (Z,2E)-2-methoxyimino-N,3-dimethyl-5-[1-(p-tolyl)pyrazol-3-yl]oxy-pent-3-enamide (I-5), (Z,2E)-5-[1-(2-methyl-4-fluoro-phenyl)pyrazol-3-yl]oxy-2-methoxyimino-N,3-dimethyl-pent-3-enamide (I-6), (Z,2E)-2-methoxyimino-N,3-dimethyl-5-[1-[4-(trifluoromethyl)-phenyl]pyrazol-3-yl]oxy-pent-3-enamide (I-7), (Z,2E)-5-[1-(3,4-dichlorophenyl)pyrazol-3-yl]oxy-2-methoxyimino-N,3-dimethyl-pent-3-enamide (I-8), (Z,2E)-5-[1-(3,4-dimethylphenyl)pyrazol-3-yl]oxy-2-methoxyimino-N,3-dimethyl-pent-3-enamide (I-9), (Z,2E)-5-[1-(4-fluoro-3-methyl-phenyl)pyrazol-3-yl]oxy-2-methoxyimino-N,3-dimethyl-pent-3-enamide (I-10), (Z,2E)-5-[1-(3-chloro-4-fluoro-phenyl)pyrazol-3-yl]oxy-2-methoxyimino-N,3-dimethyl-pent-3-enamide (I-11), (Z,2E)-5-[1-(3-fluoro-4-chloro-phenyl)pyrazol-3-yl]oxy-2-methoxyimino-N,3-dimethyl-pent-3-enamide (I-12), (Z,2E)-5-[1-(4-chloro-2-fluoro-phenyl)pyrazol-3-yl]oxy-2-methoxyimino-N,3-dimethyl-pent-3-enamide (I-13), (Z,2E)-5-[1-[4-(difluoromethoxy)phenyl]pyrazol-3-yl]oxy- 2-meth-oxyimino-N,3-dimethyl-pent-3-enamide (I-14), (Z,2E)-5-[1-(3-cyclopropylphenyl)pyrazol-3-yl]oxy-2-methoxyimino-N,3-dimethyl-pent-3-enamide (I-15), (Z,2E)-5-[1-[4-chloro-3-(trifluoromethyl)-phenyl]pyrazol-3-yl]oxy-2-methoxyimino-N,3-dimethyl-pent-3-enamide (I-16), (Z,2E)-2-methoxy-imino-N,3-dimethyl-5-[1-(3,4,5-trifluorophenyl)pyrazol-3-yl]oxy-pent-3-enamide (I-17) and (Z,2E)-2-methoxyimino-N,3-dimethyl-5-[1-[4-(trifluoromethylsulfanyl)phenyl]pyrazol-3-yl]oxy-pent-3-enamide (I-18).

According to another embodiment of the invention, compounds of formula I are selected from (Z,2E)-5-[1-(4-chlorophenyl)pyrazol-3-yl]oxy-2-methoxyimino-N,3-dimethyl-pent-3-enamide (I-1), (Z,2E)-5-[1-(2,4-dichlorophenyl)pyrazol-3-yl]oxy-2-methoxyimino-N,3-dimethyl-pent-3-enamide (I-3), and (Z,2E)-5-[1-(4-chloro-2-fluoro-phenyl)pyrazol-3-yl]oxy-2-methoxyimino-N,3-dimethyl-pent-3-enamide (I-13).

More preferably, component 1) in the inventive mixtures is selected from (Z,2E)-5-[1-(4-chlorophenyl)pyrazol-3-yl]oxy-2-methoxyimino-N,3-dimethyl-pent-3-enamide (I-1), (Z,2E)-5-[1-(2,4-dichlorophenyl)pyrazol-3-yl]oxy-2-methoxyimino-N,3-dimethyl-pent-3-enamide (I-3), and (Z,2E)-5-[1-(4-chloro-2-fluoro-phenyl)pyrazol-3-yl]oxy-2-methoxyimino-N,3-dimethyl-pent-3-enamide (I-13).

Preferably, the components 1) and 2) in these mixtures are present in a synergistically effective amount.

The invention also relates to a method for controlling phytopathogenic harmful fungi using mixtures of at least one compound I and at least one compound or biopesticide II and to the use of compounds I and compounds or biopesticides II for preparing such mixtures, and to compositions comprising these mixtures and seed comprising these mixtures or coated with these mixtures.

Practical agricultural experience has shown that the repeated and exclusive application of an individual active compound in the control of harmful fungi leads in many cases to a rapid selection of those fungus strains which have developed natural or adapted resistance against the active compound in question. Effective control of these fungi with the active compound in question is then no longer possible.

To reduce the risk of the selection of resistant fungus strains, mixtures of different active compounds are nowadays conventionally employed for controlling harmful fungi. By combining active compounds having different mechanisms of action, it is possible to ensure successful control over a relatively long period of time.

It is an object of the present invention to provide, with a view to effective resistance management and effective control of phytopathogenic harmful fungi, at application rates which are as low as possible, compositions which, at a reduced total amount of active compounds applied, have improved activity against the harmful fungi (synergistic mixtures) and a broadened activity spectrum, in particular for certain indications.

We have accordingly found that this object is achieved by the compositions, defined herein, comprising at least one compound I and at least one compound or biopesticide II.

Moreover, we have found that simultaneous, that is joint or separate, application of a compound I and a compound or biopesticide II or successive application of a compound I and of compound or biopesticide II allows better control of harmful fungi than is possible with the individual compounds alone (synergistic mixtures). Compounds I and/or the compounds II can be present in different crystal modifications, which may differ in biological activity.

Agriculturally acceptable salts of the compounds I encompass especially the salts of those cations or the acid addition salts of those acids whose cations and anions, respectively, have no adverse effect on the fungicidal action of the compounds I. Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may carry 1 to 4 $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium. Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound I with an acid of the corresponding anion, preferably of hydrochloric acid, hydrobromic acid, sulfuric acid, phosphoric acid or nitric acid.

The scope of the present invention includes mixtures of the (R)- and (S)-isomers and the racemates of compounds I and/or II having one or more chiral centers. As a result of hindered rotation of asymmetrically substituted groups, atrope isomers of compounds I and/or II may be present. They also form part of the subject matter of the invention.

The fungicidally active compounds II described by common names, their preparation and their activity against harmful fungi is known (cf.: http://www.alanwood.net/pesticides/); these substances are commercially available.

The compounds described by IUPAC nomenclature, their preparation and their fungicidal activity are also known (Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. No. 3,296,272; U.S. Pat. No. 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657, WO2012/168188, WO 2007/006670, WO 11/77514; WO13/047749, WO 10/069882, WO 13/047441, WO 03/16303, WO 09/90181, WO 13/007767, WO 13/010862, WO 13/024009 and WO 13/024010).

In particular, the compounds II-1 to II-9 and II-56 to II-77 can be obtained by various routes in analogy to processes known in the prior art (cf. J. Agric. Food Chem. (2009) 57, 4854-4860; EP 0 275 955 A1; DE 40 03 180 A1; EP 0 113 640 A2; EP 0 126 430 A2; U.S. Pat. No. 4,940,720; EP 354183 A2). Furthermore, compounds II-1 to II-9 and II-56 to II-77 or similar compounds from the triazole class, its preparation and use in crop protection are described in WO 2013/024076, WO 2013/024075, WO 2013/024077, WO 2013/024080, WO 2013/024083, WO 2013/007767 and WO 2013/010862 which also disclose certain compositions with other active compounds.

One embodiment of the invention relates to mixtures, wherein the component 2) is a C14 demethylase inhibitors selected from 2-[2-chloro-4-(4-chlorophenoxy)phenyl]-1-(1,2,4-triazol-1-yl)pentan-2-ol (II-1), 1-[4-(4-chlorophenoxy)-2-(trifluoromethyl)phenyl]-1-cyclopropyl-2-(1,2,4-triazol-1-yl)ethanol (II-2), 2-[4-(4-chlorophenoxy)-2-(trifluoromethyl)phenyl]-1-(1,2,4-triazol-1-yl)butan-2-ol (II-3), 2-[2-chloro-4-(4-chlorophenoxy)phenyl]-1-(1,2,4-triazol-1-yl)butan-2-ol (II-4), 2-[4-(4-chlorophenoxy)-2-(trifluoromethyl)phenyl]-3-methyl-1-(1,2,4-triazol-1-yl)butan-2-ol (II-5), 2-[4-(4-chlorophenoxy)-2-(trifluoromethyl)phenyl]-1-(1,2,4-triazol-1-yl)propan-2-ol (II-6), 2-[2-chloro-4-(4-chlorophenoxy)phenyl]-3-methyl-1-(1,2,4-triazol-1-yl)butan-2-ol (II-7), 2-[4-(4-chlorophenoxy)-2-(trifluoromethyl)phenyl]-1-(1,2,4-triazol-1-yl)pentan-2-ol (II-8), 2-[4-(4-fluorophenoxy)-2-(trifluoromethyl)phenyl]-1-(1,2,4-triazol-1-yl)propan-2-ol (II-9), 2-[2-chloro-4-(4-chlorophenoxy)phenyl]-1-(1,2,4-triazol-1-yl)pent-3-yn-2-ol (II-56); 1-[2-chloro-4-(4-chlorophenoxy)phenyl]-1-cyclopropyl-2-(1,2,4-triazol-1-yl)ethanol (II-57); 1-[2-[2-chloro-4-(4-chlorophenoxy)phenyl]-2-methoxy-pent-3-ynyl]-1,2,4-triazole (II-58); 1-[2-[2-chloro-4-(4-chlorophenoxy)phenyl]-2-cyclopropyl-2-methoxy-ethyl]-1,2,4-triazole (II-59); 1-[2-[4-(4-chlorophenoxy)-2-(trifluoromethyl)phenyl]-2-methoxy-propyl]-1,2,4-triazole (II-60); 2-[2-chloro-4-(4-chlorophenoxy)phenyl]-3,3-dimethyl-1-(1,2,4-triazol-1-yl)butan-2-ol (II-61); 1-[2-[4-(4-chlorophenoxy)-2-(trifluoromethyl)phenyl]-2-cyclopropyl-2-methoxy-ethyl]-1,2,4-triazole (II-62); 1-[2-[2-chloro-4-(4-chlorophenoxy)phenyl]-2-methoxy-3,3-dimethyl-butyl]-1,2,4-triazole (II-63); 1-[2-[4-(4-chlorophenoxy)-2-(trifluoromethyl)phenyl]-2-methoxy-butyl]1,2,4-triazole (II-64); 2-[4-(4-chlorophenoxy)-2-(trifluoromethyl)phenyl]-1-(1,2,4-triazol-1-yl)pent-3-yn-2-ol (II-65); 1-[2-[4-(4-chlorophenoxy)-2-(trifluoromethyl)phenyl]-2-methoxy-pent-3-ynyl]-1,2,4-triazole (II-66); 2-[4-(4-chlorophenoxy)-2-(trifluoromethyl)phenyl]-1-(1,2,4-triazol-1-yl)but-3-yn-2-ol (II-67); 2-[2-chloro-4-(4-chlorophenoxy)phenyl]-1-(1,2,4-triazol-1-yl)propan-2-ol (II-68); 2-[2-chloro-4-(4-fluorophenoxy)phenyl]-1-(1,2,4-triazol-1-yl)propan-2-ol (II-69); 1-[2-[2-chloro-4-(4-chloro-phenoxy)phenyl]-2-methoxy-propyl]-1,2,4-triazole (II-70); 1-[2-[2-chloro-4-(4-chlorophenoxy)-phenyl]-2-methoxy-butyl]-1,2,4-triazole (II-71); 1-[2-[2-chloro-4-(4-chlorophenoxy)phenyl]-2-methoxy-pentyl]-1,2,4-triazole (II-72); 2-[2-chloro-4-(4-chlorophenoxy)phenyl]-1,1,1-trifluoro-3-(1,2,4-triazol-1-yl)propan-2-ol (II-73); 2-[2-chloro-4-(4-chlorophenoxy)phenyl]-3-fluoro-1-(1,2,4-triazol-1-yl)butan-2-ol hydrochloride (II-74); 2-[2-chloro-4-(4-chlorophenoxy)phenyl]-1-(1,2,4-triazol-1-yl)pent-4-yn-2-ol (II-75); 2-[2-chloro-4-(4-chlorophenoxy)phenyl]-1-methoxy-3-(1,2,4-triazol-1-yl)propan-2-ol (II-76) and 2-[2-chloro-4-(4-fluorophenoxy)phenyl]-1-methoxy-3-(1,2,4-triazol-1-yl)propan-2-ol (II-77).

Owing to the basic character of their nitrogen atoms, the component 2) that is selected from II-1, II-2, II-3, II-4, II-5, II-6, II-7, II-8, II-9, II-56, II-57, II-58, II-59, II-60, II-61, II-62, II-63, II-64, II-65, II-66, II-67, II-68, II-69, II-70, II-71, II-72, II-73, II-74, II-75, II-76 and II-77 or any group of these compounds detailed herein, is capable of forming salts or adducts with inorganic or organic acids or with metal ions, in particular salts with inorganic acids.

Examples of inorganic acids are hydrohalic acids, such as hydrogen fluoride, hydrogen chloride, hydrogen bromide and hydrogen iodide, carbonic acid, sulfuric acid, phosphoric acid and nitric acid.

Suitable organic acids are, for example, formic acid and alkanoic acids, such as acetic acid, trifluoroacetic acid, trichloroacetic acid and propionic acid, and also glycolic acid, thiocyanic acid, lactic acid, succinic acid, citric acid, benzoic acid and other arylcarboxylic acids, cinnamic acid, oxalic acid, alkylsulfonic acids (sulfonic acids having straight-chain or branched alkyl radicals of 1 to 20 carbon atoms), arylsulfonic acids or aryldisulfonic acids (aromatic radicals, such as phenyl and naphthyl, which carry one or two sulfonic acid groups), alkylphosphonic acids (phosphonic acids having straight-chain or branched alkyl radicals with 1 to 20 carbon atoms), arylphosphonic acids or aryldiphosphonic acids (aromatic radicals, such as phenyl and naphthyl, which carry one or two phosphoric acid radicals), where the alkyl or aryl radicals may carry further substituents, for example p-toluenesulfonic acid, salicylic acid, p-aminosalicylic acid, 2-phenoxybenzoic acid, 2-acetoxybenzoic acid etc. Suitable metal ions are in particular the ions of the elements of the second main group, in particular calcium and magnesium, of the third and fourth main group, in particular aluminum, tin and lead, and also of the elements of transition groups one to eight, in particular chromium, manganese, iron, cobalt, nickel, copper, zinc, and others. Particular preference is given to the metal ions of the elements of transition groups of the fourth period. The metals can be present in the various valencies that they can assume.

Compounds II-1, II-2, II-3, II-4, II-5, II-6, II-7, II-8, II-9, II-56, II-57, II-58, II-59, II-60, II-61, II-62, II-63, II-64, II-65, II-66, II-67, II-68, II-69, II-70, II-71, II-72, II-73, II-74, II-75, II-76 and II-77 comprise chiral centers and they are generally obtained in the form of racemates. The R- and S-enantiomers of said compounds can be separated and isolated in pure form with methods known by the skilled person, e.g. by using chiral HPLC. Suitable for use as antimicrobial agents are both the enantiomers and compositions thereof. This applies correspondingly to the compositions. Furthermore, components 2), namely compounds II-1, II-2, II-3, II-4, II-5, II-6, II-7, II-8, II-9, II-56, II-57, II-58, II-59, II-60, II-61, II-62, II-63, II-64, II-65, II-66, II-67, II-68, II-69, II-70, II-71, II-72, II-73, II-74, II-75, II-76 and II-77, can be present in different crystal modifications, which may differ in biological activity.

In particular, in each case, a racemic composition is present. Furthermore, any other proportions of the (R)-enantiomer and the (S)-enantiomer may be present according to the present invention. This applies to every composition comprising a compound selected from II-1, II-2, II-3, II-4, II-5, II-6, II-7, II-8, II-9, II-56, II-57, II-58, II-59, II-60, II-61, II-62, II-63, II-64, II-65, II-66, II-67, II-68, II-69, II-70, II-71, II-72, II-73, II-74, II-75, II-76 and II-77 detailed herein.

According to one embodiment of the present invention, component 2) is compound II-1. Compound II-1 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-1.

According to one specific embodiment, the compound II-1 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-1 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further embodiment of the present invention, component 2) is compound II-2. Compound II-2 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-2.

According to one specific embodiment, the compound II-2 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-2 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2) is compound II-3. Compound II-3 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-3.

According to one specific embodiment, the compound II-3 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-3 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2) is compound II-4. Compound II-4 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-4.

According to one specific embodiment, the compound II-4 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-4 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2) is compound II-5. Compound II-5 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-5.

According to one specific embodiment, the compound II-5 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-5 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2) is compound II-6. Compound II-6 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-6.

According to one specific embodiment, the compound II-6 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-6 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2) is compound II-7. Compound II-7 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-7.

According to one specific embodiment, the compound II-7 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-7 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2) is compound II-8. Compound II-8 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-8.

According to one specific embodiment, the compound II-8 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-8 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2 is compound II-9. Compound II-9 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-9.

According to one specific embodiment, the compound II-9 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-9 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2) is compound II-56. Compound II-56 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-56.

According to one specific embodiment, the compound II-56 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-56 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2) is compound II-57. Compound II-57 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-57.

According to one specific embodiment, the compound II-57 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-57 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2)I is compound II-58. Compound II-58 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-58.

According to one specific embodiment, the compound II-58 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-58 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2) is compound II-59. Compound II-59 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-59.

According to one specific embodiment, the compound II-59 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-59 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2) is compound II-60. Compound II-60 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-60.

According to one specific embodiment, the compound II-60 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-60 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2) is compound II-61. Compound II-61 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-61.

According to one specific embodiment, the compound II-61 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-61 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2) is compound II-62. Compound II-62 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-62.

According to one specific embodiment, the compound II-62 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-62 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2) is compound II-63. Compound II-63 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-63.

According to one specific embodiment, the compound II-63 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-63 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2) is compound II-64. Compound II-64 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-64.

According to one specific embodiment, the compound II-64 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-64 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2) is compound II-65. Compound II-65 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-65.

According to one specific embodiment, the compound II-65 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-65 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2) is compound II-66. Compound II-66 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-66.

According to one specific embodiment, the compound II-66 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-66 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2) is compound II-67. Compound II-67 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-67.

According to one specific embodiment, the compound II-67 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-67 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2) is compound II-68. Compound II-68 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-68.

According to one specific embodiment, the compound II-68 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-68 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2) is compound II-69. Compound II-69 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-69.

According to one specific embodiment, the compound II-69 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-69 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2) is compound II-70. Compound II-70 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-70.

According to one specific embodiment, the compound II-70 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-70 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2) is compound II-71. Compound II-71 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-71.

According to one specific embodiment, the compound II-71 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-71 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2) is compound II-72. Compound II-72 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-72.

According to one specific embodiment, the compound II-72 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-72 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2) is compound II-73. Compound II-73 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-73.

According to one specific embodiment, the compound II-73 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-73 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2) is compound II-74. Compound II-74 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-74.

According to one specific embodiment, the compound II-74 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-74 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2) is compound II-75. Compound II-75 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-75.

According to one specific embodiment, the compound II-75 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-75 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2) is compound I-76. Compound II-76 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-76.

According to one specific embodiment, the compound II-76 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-76 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to still a further embodiment of the present invention, component 2) is compound II-77. Compound II-77 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of II-77.

According to one specific embodiment, the compound II-77 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound II-77 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to one embodiment of the present invention, the component 2) is selected from compounds II-68, II-69, II-7, II-73, II-75 and II-9. According to one further embodiment of the present invention, component 2) is selected from compounds II-7, II-73, II-75, II-8, II-9, II-4 and II-1. According to still a further embodiment of the present invention, component 2) is selected from compounds II-68, II-69, II-76 and II-77. According to another more embodiment of the present invention, component I is selected from compounds II-70, II-71, II-72 and II-74.

According to one further embodiment of the present invention, component 2) is selected from compounds II-56, II-57, II-6, II-2, II-5, II-58, II-3, II-59, II-60, II-61, II-62, II-63, II-64, II-65, II-66 and I-67. According to a more particular embodiment of the present invention, component 2) is selected from compounds II-56, II-57, II-58, II-59 and II-63. According to another more particular embodiment of the present invention, component 2) is selected from compounds II-6, II-2, II-5, II-3, II-60, II-62, II-64, II-65, II-66 and II-67.

According to still a further embodiment of the present invention, component 2) is selected from compounds II-56, II-57, II-6, II-2, II-5 and II-68.

According to still a further embodiment of the present invention, component 2) is selected from compounds II-56, II-57, II-6, II-2 and II-5.

According to still a further embodiment of the present invention, component 2) is selected from compound II-68 and II-69.

According to still a further embodiment of the present invention, component 2) is selected from compounds 1-[4-(4-chlorophenoxy)-2-(trifluoromethyl)phenyl]-1-cyclopropyl-2-(1,2,4-triazol-1-yl)ethanol (II-2), 2-[4-(4-chlorophenoxy)-2-(trifluoromethyl)phenyl]-3-methyl-1-(1,2,4-triazol-1-yl)butan-2-ol (II-5), 2-[4-(4-chlorophenoxy)-2-(trifluoromethyl)phenyl]-1-(1,2,4-triazol-1-yl)propan-2-ol (II-6), and 1-[2-chloro-4-(4-chlorophenoxy)phenyl]-1-cyclopropyl-2-(1,2,4-triazol-1-yl)ethanol (II-57).

Biopesticides have been defined as a form of pesticides based on micro-organisms (bacteria, fungi, viruses, nematodes, etc.) or natural products (compounds or extracts from biological sources). Biopesticides are typically created by growing and concentrating naturally occurring organisms and/or their metabolites including bacteria and other microbes, fungi, viruses, nematodes, proteins, etc. They are often considered to be important components of integrated pest management (IPM) programmes, and have received much practical attention as substitutes to synthetic chemical plant protection products (PPPs).

Biopesticides fall into two major classes, microbial and biochemical pesticides:
(1) Microbial pesticides consist of bacteria, fungi or viruses (and often include the metabolites that bacteria and fungi produce). Entomopathogenic nematodes are also classed as microbial pesticides, even though they are multi-cellular.
(2) Biochemical pesticides are naturally occurring substances that control pests or provide other crop protection uses as defined below, but are relatively non-toxic to mammals.

The biopesticides II from group D) and/or E) may also have insecticidal, acaricidal, molluscidal, pheromone, nematicidal, plant stress reducing, plant growth regulator, plant growth promoting and/or yield enhancing activity.

The biopesticides from group F) and/or G) may also have fungicidal, bactericidal, viricidal, plant defense activator, plant stress reducing, plant growth regulator, plant growth promoting and/or yield enhancing activity.

The biopesticides from group G) and/or H) may also have fungicidal, bactericidal, viricidal, plant defense activator, insecticidal, acaricidal, molluscidal, pheromone and/or nematicidal activity.

Many of these biopesticides II and III have been deposited under deposition numbers mentioned herein (the prefaces refer to the acronym of the respective culture collection), are referred to in literature, registered and/or are commercially available: aluminium silicate (Screen™ Duo from Certis LLC, USA), *Agrobacterium radiobacter* K1026 (e. g. NoGall® from BASF Agricultural Specialties Pty Ltd, Australia), *A. radiobacter* K84 (Nature 280, 697-699, 1979; e. g. GallTroll® from AG Biochem, Inc., C, USA), *Ampelomyces quisqualis* M-10 (e. g. AQ 10® from Intrachem Bio GmbH & Co. KG, Germany), *Ascophyllum nodosum* (Norwegian kelp, Brown kelp) extract or filtrate (e. g. ORKA GOLD from BASF Agricultural Specialities (Pty) Ltd., South Africa; or Goemar® from Laboratoires Goemar, France), *Aspergillus flavus* NRRL 21882 isolated from a peanut in Georgia in 1991 by USDA, National Peanut Research Laboratory (e. g. in Afla-Guard® from Syngenta, CH), mixtures of *Aureobasidium pullulans* DSM 14940 and DSM 14941 (e. g. blastospores in BlossomProtect® from bio-ferm GmbH, Germany), *Azospirillum amazonense* SpY2 (DN: BR 11140; Proc. 9$^{th}$ Int. and 1$^{st}$ Latin American PGPR meeting, Quimara, Medellin, Colombia 2012, p. 60, ISBN 978-958-46-0908-3), *A. brasilense* AZ39 (also called Az 39; INTA Az-39; Eur. J. Soil Biol 45(1), 28-35, 2009), *A. brasilense* XOH (e. g. AZOS from Xtreme Gardening, USA or RTI Reforestation Technologies International; USA), *A. brasilense* BR 11002 (Proc. 9$^{th}$ Int. and 1$^{st}$ Latin American PGPR meeting, Quimara, Medellin, Colombia 2012, p. 60, ISBN 978-958-46-0908-3), *A. brasilense* Sp245 (BR 11005; e. g. in GELFIX Gramineas from BASF Agricultural Specialties Ltd., Brazil), *A. brasilense* strains Ab-V5 and Ab-V6 (e. g. in AzoMax from Novozymes BioAg Produtos papra Agricultura Ltda., Quattro Barras, Brazil or SimbioseMaiz® from Simbiose-Agro, Cruz Alta, RS, Brazil; Plant Soil 331, 413-425, 2010), *A. lipoferum* BR 11646 (Sp31) (Proc. 9$^{th}$ Int. and 1$^{st}$ Latin American PGPR meeting, Quimara, Medellin, Colombia 2012, p. 60), *Bacillus altitudinis* 41KF2b (DSM 21631; Int. J. Syst. Evol. Microbiol. 56(7), 1465-1473, 2006), *Bacillus amyloliquefaciens* strains AP-136 (NRRL B-50614 and B-50330), AP-188 (NRRL B-50615 and B-50331), AP-218 (NRRL B-50618), AP-219 (NRRL B-50619 and B-50332), and AP-295 (NRRL B-50620 and B-50333) all known from U.S. Pat. No. 8,445,255; *B. amyloliquefaciens* IT-45 (CNCM I-3800) (e. g. Rhizocell C from ITHEC, France), *B. amyloliquefaciens* IN937a (J. Microbiol. Biotechnol. 17(2), 280-286, 2007; e. g. BioYield® from Gustafson LLC, TX, USA), *B. amyloliquefaciens* spp. *plantarum* D747 (US 20130236522 A1; FERM BP-8234; e. g. Double Nickel™ 55 WDG or Double Nickel™ LC from Certis LLC, USA), *B. amyloliquefaciens* spp. *plantarum* FZB24 isolated from plant pathogen-infested soil of a sugar beet field in Brandenburg, Germany (also called SB3615; DSM ID 96-2; J. Plant Dis. Prot. 105, 181-197, 1998; e. g. Taegro® from Novozyme Biologicals, Inc., USA), *B. amyloliquefaciens* spp. *plantarum* SB3615vPPI being a phage-resistant variant of FZB24 (MRRL B-50349; US 2011/023045 A1; from Novozyme Biologicals, Inc., USA), *B. amyloliquefaciens* ssp. *plantarum* FZB42 isolated from plant pathogen-infested soil of a sugar beet field in Brandenburg, Germany (J. Plant Dis. Prot. 105, 181-197, 1998; DSM 23117; e. g. RhizoVital® 42 from AbiTEP GmbH, Berlin, Germany), *B. amyloliquefaciens* ssp. *plantarum* GB03 (also called GBO3; ATCC SD-1397; Phytopathol. 86(11), S36, 1996; e. g. Kodiak® or BioYield® from Gustafson, Inc., USA; or Companion® from Growth Products, Ltd., White Plains, N.Y. 10603, USA), *B. amyloliquefaciens* ssp. *plantarum* MBI600 also referred to as 1430 (NRRL B-50595; Int. J. Microbiol. Res. 3(2) (2011), 120-130; US 2012/0149571 A1; e. g. Integral®, Subtilex® NG from BASF Corp., USA), *B. amyloliquefaciens* spp. *plantarum* TJ 1000 (also called 1 BE; CA 2471555 A1; ATCC BAA-390; e. g. QuickRoots™ from TJ Technologies, Watertown, S. Dak., USA), *B. cereus* CNCM I-1562 (U.S. Pat. No. 6,406,690), *B. chitinosporus* AQ746 isolated from roots in Saskatchewan, Canada (NRRL B-21618; U.S. Pat. No. 5,733,544; AgraQuest now Bayer CropScience LP, USA), *B. firmus* CNCM I-1582 (WO 2009/126473, WO 2009/124707, U.S. Pat. No. 6,406,690; e. g. Votivo® from Bayer CropScience LP, USA), *B. megaterium* strains H491 (NRRL B-50769), M018 (NRRL B-50770) and J142 (NRRL B-50771) all known from US 2014/0051571 A1 from Marrone BioInnovations, Inc., USA; *B. mojavensis* AP-209 (NRRL B-50616; U.S. Pat. No. 8,445,255), *B. mycoides* AQ726 (NRRL B-21664; U.S. Pat. No. 5,906,818; from Bayer Crop Science, Germany), *B. mycoides* strain J (e.g. BmJ WG from Certis, USA against potato virus Y), *B. pumilus* GB34 (ATCC 700814; e. g. YieldShield® from Gustafson LLC, TX, USA), *B. pumilus* GHA 180 isolated from apple tree rhizosphere in Mexico (IDAC 260707-01; e. g. in PRO-MIX® BX from Premier Horticulture, 1, avenue Premier, Rivie're-du-Loup, Quebec, Canada G5R6C1), *B. pumilus* KFP9F (NRRL B-50754; WO 2014/029697; e. g. BAC-UP or FUSION-P from BASF Agricultural Specialities (Pty) Ltd., South Africa), *B. pumilus* INR-7 otherwise referred to as BU-F22 and BU-F33 (NRRL B-50185, NRRL B-50153; U.S. Pat. No. 8,445,255), *B. pumilus* QST 2808 (NRRL B-30087; e. g. Sonata® or Ballad® Plus from AgraQuest Inc., USA), *B. solisalsi* AP-217 (NRRL B-50617; U.S. Pat. No. 8,445,255), *B. subtilis* CX-9060 (Federal Register 77(7), 1633-1637; by Certis U.S.A., L.L.C.), *B. subtilis* FB17 also called UD 1022 or UD10-22 isolated from red beet roots in North America (ATCC PTA-11857; System. Appl. Microbiol. 27, 372-379, 2004; US 2010/0260735; WO 2011/109395); *B. subtilis* GB07 (Phytopathol. 86(11), S36, 1996; Epic® from Gustafson, Inc., USA), *B. subtilis* QST-713 isolated from a California peach orchard in 1995 (NRRL B-21661; e. g. Rhapsody®, Serenade® MAX or Serenade® ASO from AgraQuest Inc., USA), *B. thuringiensis* ssp. *aizawai* ABTS-1857 (also called ABG-6346; ATCC SD-1372; e. g. XenTari® from BioFa AG, Münsingen, Germany), *B. t.* ssp. *aizawai* SAN 401 I, ABG-6305 (WO 2013/087709); *Bacillus t.* ssp. *israelensis* AM65-52 of Serotype H-14 (ATCC SD-1276; e. g. VectoBac® from Valent BioSciences, IL, USA), *Bacillus thuringiensis* ssp. *kurstaki* SB4 (NRRL B-50753; e. g. Beta Pro® from BASF Agricultural Specialities (Pty) Ltd., South Africa), *B. t.* ssp. *kurstaki* ABTS-351 identical to HD-1 (ATCC SD-1275; e. g. Dipel® DF from Valent BioSciences, IL, USA), *B. t.* ssp. *kurstaki* EG 2348 (NRRL B-18208; e. g. Lepinox® or Rapax® from CBC (Europe) S.r.I., Italy), *B. t.* ssp. *tenebrionis* DSM 2803 of Serotype H 8a, 8b (identical to NRRL B-15939; EP 0 585 215 B1; Mycogen Corp.), *B. t.* ssp. *tenebrionis* NB-125 (also referred to as SAN 418 I or ABG-6479; EP 0 585 215 B1; DSM 5526; former production strain of Novo-Nordisk), *B. t.* ssp. *tenebrionis* NB-176 (or NB-176-1; a gamma-irridated, induced high-yielding mutant of strain NB-125; EP 585 215 B1; DSM 5480; e. g. Novodor® from Valent BioSciences, Switzerland), *Beauveria bassiana* JW-1 (ATCC 74040; e. g. Naturalis® from CBC (Europe) S.r.I., Italy), *B. bassiana* DSM 12256 (US 200020031495; e. g. BioExpert® SC from Live Systems Technology S.A., Colombia), *B. bassiana* GHA (ATCC 74250; e. g. BotaniGard® 22WGP from Laverlam Int. Corp., USA), *B. bassiana* PPRI 5339 (ARSEF 5339; NRRL 50757; e. g. BroadBand® from BASF Agricultural Specialities (Pty) Ltd., South Africa), *B. brongniartii* for control of cockchafer (J. Appl. Microbiol. 100(5), 1063-72, 2006; e. g. Melocont® from Agrifutur, Agrianello, Italy), *Bradyrhizobium* sp. (e. g. Vault® from BASF Corp., USA), *B. sp. (Arachis)* CB1015 presumably originally collected in India (IITA 1006, USDA 3446; from Australian Inoculants Research Group; http://www.qaseeds.com.au/inoculant_applic.php). *B.* sp. *(Arachis)* strains deposited at SEMIA and known from FEMS Microbiol. Letters 303(2), 123-131, 2010; Revista Brasileira de Ciencia do Solo 35(3), 739-742, 2011, ISSN 0100-0683: SEMIA 6144, SEMIA 6462 (BR 3267) and SEMIA 6464 (BR 3262); *B.* sp. *(Vigna)* PNL01 (Bisson and Mason, Apr. 29, 2010, Project report, Worcester Polytechnic Institute, Worcester, Mass., USA: http:// www.wpi.edu/Pubs/E-project/Available/E-project-042810-163614/; e. g. Vault® Peanut Liquid from BASF Corp., USA), *B. elkanii* SEMIA 587 (Appl. Environ. Microbiol. 73(8), 2635, 2007; e. g. GELFIX 5 from BASF Agricultural Specialties Ltd., Brazil), *B. elkanii* SEMIA 5019 (=29W; Appl. Environ. Microbiol. 73(8), 2635, 2007; e. g. GELFIX 5 from BASF Agricultural Specialties Ltd., Brazil), *B. elkanii* USDA 76, *B. elkanii* USDA 94*B. elkanii* USDA 3254, *B. elkanii* U-1301 and U-1302 (e. g. Nitragin® Optimize from Novozymes Bio As S.A., Brazil, or Nlitrasec for soybean from LAGE y Cia, Brazil), *B. japonicum* (e. g. VAULT® from BASF Corp., USA), *B. japonicum* 532c isolated from Wisconsin field (Nitragin 61A152; Can. J. Plant. Sci. 70, 661-666, 1990; e. g. in Rhizoflo®, Histick®, Hicoat® Super from BASF Agricultural Specialties Ltd., Canada), *B. japonicum* E-109 variant of strain USDA 138 (INTA E109, SEMIA 5085; Eur. J. Soil Biol. 45, 28-35, 2009; Biol. Fertil. Soils 47, 81-89, 2011), *B. japonicum* G49 (MSDJ G49; C. R. Acad. Agric. Fr. 73, 163-171, 1987); *B. japonicum* strains deposited at SEMIA known from Appl. Environ. Microbiol. 73(8), 2635, 2007: SEMIA 566 isolated from North American inoculant in 1966 and used in Brazilian commercial inoculants from 1966 to 1978, SEMIA 586 originally isolated in Maryland, USA, in 1961 but received from Australia in 1966 and used in Brazilian inoculants in 1977 (CB 1809, USDA 136, Nitragin 61A136, RCR 3407), SEMIA 5079 a natural variant of SEMIA 566 used in commercial inoculants since 1992 (CPAC 15; e. g. GELFIX 5 or ADHERE 60 from BASF Agricultural Specialties Ltd., Brazil), *B. japonicum* SEMIA 5080 a natural variant of SEMIA 586 used in commercial inoculants since 1992 (CPAC 7; e. g. GELFIX 5 or ADHERE 60 from BASF Agricultural Specialties Ltd., Brazil); *B. japonicum* TA-11 (TA11 NOD$^+$) (NRRL B-18466; U.S. Pat. No. 5,021,076; Appl. Environ. Microbiol. 56, 2399-2403, 1990; e. g. VAULT® NP, from BASF Corp., USA), *B. japonicum* strains deposited at USDA known from U.S. Pat. No. 7,262,151 and Appl. Environ. Microbiol. 60, 940-94, 1994: USDA 3 isolated from *Glycine max* in Virginia (USA) in 1914, USDA 31 (=Nitragin 61A164) od Serogroup 31 isolated from *Glycine max* in Wisconsin (USA) in 1941, USDA 76 isolated from plant passage of strain USDA 74 (Serogroup 76) which has been isolated from *G. max* in California (USA) in 1956, USDA 110 (=IITA 2121, SEMIA 5032, RCR 3427, ARS I-110 and Nitragin 61A89; Serogroup 110) isolated from *G. max* in Florida in 1959, USDA 121 isolated from *G. max* in Ohio (USA) in 1965 (Crop Science 26(5), 911-916, 1986); *B. japonicum* WB74 (e. g. Eco-Rhiz Soya from Plant Health Products (Pty) Ltd, South Africa; or Soybean inoculant from Stimuplant CC, South Africa), *B. lupini* LL13 isolated from *Lupinus iuteus* nodules from French soils (deposited at INRA, France; http://agriculture.gouv.fr/IMG/pdf/ch20060216.pdf), *B. lupini* strains from Australia and known from Palta J. A., Berger J. B. (eds), Proceed. 12$^{th}$ International Lupin Conference, 14-18 Sep. 2008, Fremantle, Western Australia, International Lupin Association, Canterbury, New Zealand, 47-50, http://www.upins.org/pdf/conference/2008/Agronomy%20and%20Production/John%20Howieson%20and%20G%20OHara.pdf; Appl. Environ. Microbiol. 71, 7041-7052, 2005; Australian J. Exp. Agricult. 36(1), 63-70, 1996: strains WU425 isolated in Esperance, Western Australia from a non-Australian legume *Ornithopus compressus*, WSM471 isolated from *Ornithopus pinnatus* in Oyster Harbour, Western Australia, and WSM4024 isolated from lupins in Australia by CRS during a 2005 survey; *Burkholderia* sp. A396 (NRRL B-50319; WO 2013/032693; Marrone Bio Innovations, Inc., USA), *Candida oleophila* I-182 (NRRL Y-18846; Phytoparasitica 23(3), 231-234, 1995; e. g. Aspire® from Ecogen Inc., USA;), *C. oleophila* strain O (NRRL Y-2317; Biological Control 51, 403-408, 2009), *Candida saitoana* (e. g. Biocure® [in mixture with lysozyme] and BioCoat® from Micro Flo Company, USA (BASF SE) and Arysta), chitosan (e. g. Armour-Zen® from BotriZen Ltd., NZ), *Clonostachys rosea* f. *catenulate* (also named *Gliocladium catenulatum*) J1446 isolated from Finnish field soil (NJF seminar No 389: Pest, disease and weed management in strawberry; Finland 8-9 Nov. 2006 in NJF Report 2(10), 15-15, 2006; DSM 9212; e. g. Primastop® or Prestop® from Verdera Oy, Finland), *Chromobacterium subtsugae* PRAA4-1 isolated from soil under an eastern hemlock (*Tsuga canadensis*) in the Catoctin Mountain region of central Maryland (NRRL B-30655; e. g. Grandevo® from Marrone Bio Innovations, USA), *Coniothyrium minitans* CON/M/91-08 (WO 1996/021358; DSM 9660; e. g. Contans® WG, Intercept® WG from Prophyta Biologischer Pflanzenschutz GmbH, Germany), *Cryphonectria parasitica* (hypovirulent strains; Microbiol. Reviews 56(4), 561-576, 1992; e. g. product Endothia parasitica from CNICM, France), *Cryptococcus albidus*(e. g. YIELD PLUS® from Anchor Bio-Technologies, South Africa), *Cryptophlebia leucotreta* granulovirus (CrleGV) (e. g. CRYPTEX from Adermatt Biocontrol, Switzerland), *Cydia pomonella* granulovirus (CpGV) V03 (DSM GV-0006; e. g. Madex® Max from Andermatt Biocontrol, Switzerland), CpGV V22 (DSM GV-0014; e. g. Madex® Twin from Adermatt Biocontrol, Switzerland), *Delftia acidovorans* RAY209 (ATCC PTA-4249; WO 2003/57861; e. g. BioBoost® from Brett Young, Winnipeg, Canada), *Dilophosphora alopecuri*(FarmNote 396, February 2010, Department of Agriculture and Food, Government of Western Australia; e.g. Twist Fungus from BASF Agricultural Specialties Pty Ltd, Australia), *Ecklonia maxima* (kelp) extract (J. Ecological Engineering 14(1), 48-52, 2013; e. g. KELPAK SL from Kelp Products Ltd, South Africa), *Flavobacterium* sp. H492 (ATCC B-505584; WO 2013/138398; e. g. MBI-302 from Marrone Bio Innovations, USA for soyean cyst nematode control), formononetin (U.S. Pat. No. 5,002,603; e. g. Myconate® from Plant Health Care plc, U.K.), *Fusarium oxysporum* Fo47 (non-pathogenic strain isolated from a suppressive soil located at Châteaurenard, France; Appl. Environ. Microbiol 68(8), 4044-4060, 2002; Fusaclean® from Natural Plant Protection, N.P.P. (société anonyme) Route d'Artix F-64150 Nogueres, France), *F. oxysporum* 251/2RB (Prevention Today Vol. 2, n. 1-2, 47-62, 2006; e. g. Biofox® C from S.I.A.P.A., Italy); *Glomus intraradices* (e. g. Myc® 4000 from ITHEC, France), *Glomus intraradices* RTI-801 (e. g. MYKOS from Xtreme Gardening, USA or RTI Reforestation Technologies International; USA), grapefruit seeds and pulp extract (e. g. BC-1000 from Chemie S.A., Chile), harpin (alpha-beta) protein (Science 257, 85-88, 1992; e. g. Messenger™ or HARP-N-Tek from Plant Health Care plc, U.K.), *Helicoverpa armigera* nucleopolyhedrovirus (HearNPV) (J. Invertebrate Pathol. 107, 112-126, 2011; e. g. Helicovex® from Adermatt Biocontrol, Switzerland), *Heterorhabditis bacteriophora* (e. g. Nemasys® G from BASF Agricultural Specialities Limited, UK), *Isaria fumosorosea* Apopka-97 (ATCC 20874; Biocontrol Science Technol. 22(7), 747-761, 2012; e. g. PFR-97™ or PreFeRal® from Certis LLC, USA), *L. fumosorosea* FE 9901 (ARSEF 4490; Biocontrol Science Technol. 22(7), 747-761, 2012; e. g. blastospores in NoFly™ WP from Natural Industries, Inc., Houston, Tex., USA or from Novozymes, U.S.A.), cis-jasmone (U.S. Pat.

No. 6,890,525; U.S. Pat. No. 8,221,736; Plant Bioscience Limited, Norwich, U.K.), laminarin (e. g. in Vacciplant® from Laboratoires Goemar, St. Malo, France or Stähler S A, Switzerland), *Lecanicillium longisporum* KV42 and KV71 (e. g. Vertalec® from Koppert BV, Netherlands), *L. muscarium* Ve6 (also called KV01; IMI 19-79, CABI 268317, CBS 102071, ARSEF 5128; e. g. Mycotal® from Koppert BV, Netherlands), *Lysobacter antibioticus* 13-1 (Biological Control 45, 288-296, 2008), *L. antibioticus* HS124 (Curr. Microbiol. 59(6), 608-615, 2009), *L. enzymogenes* 3.1T8 (Microbiol. Res. 158, 107-115, 2003; Biological Control 31(2), 145-154, 2004); *Mesorhizobium* spp. strains known from Soil Biol. Biochem. 36(8), 1309-1317, 2004; Plant and Soil 348(1-2), 231-243, 2011: *M.* sp. WSM1271 collected in Sardinia, Italy, from plant host *Biserrula pelecinus*, *M.* sp. WSM 1497 collected in Mykonos, Greece, from *Biserrula pelecinus*, *Mesorhizobium ciceri* CC1192 collected in Israel from *Cicer arietinum* nodules (UPM 848, CECT 5549; Can. J. Microbiol. 48, 279-284, 2002; from Horticultural Research Station, Gosford, Australia), *M. huakuii* HN3015 isolated from *Astralagus sinicus* in a rice-growing field of Southern China (World J. Microbiol. Biotechn. 23(6), 845-851, 2007, ISSN 0959-3993), *M. loti* CC829 isolated from *L. ulginosus* nodules in USA (NZP 2012; commerical inoculant for *Lotus pedunculatus* and *L. ulginosus* in Australia), and *M. loti* SU343 isolated from host nodules in USA (commercial inoculant for *Lotus corniculatus* in Australia); *Metarhizium anisopliae* FI-1045 (AGAL V10/0104285; WO 2012/018266; e. g. Biocane® from BASF Agricultural Specialties Pty Ltd, Australia), *M. anisopliae* var. *anisopliae* F52 also called 275 or V275 (DSM 3884, ATCC 90448; e. g. Met52® Novozymes Biologicals BioAg Group, Canada), *M. anisopliae* ICIPE 69 isolated from a soil sample obtained from the Democratic Republic of Congo (DRC) and using the Galleria bait method in 1990 (e. g. Metathripol from ICIPE, Nairobe, Kenya), *M. anisopliae* var. *acridum* IMI 330189 isolated from *Ornithacris cavroisi* in Niger (NRRL 50758; e. g. Green Muscle® from BASF Agricultural Specialities (Pty) Ltd., South Africa), *M. a.* var. *acridum* FI-985 isolated from a spur-throated locust, Austracris guttulosa (Walker), near Rockhampton, Queensland, Australia, in 1979 (ARSEF 324; Memoirs of the Entomological Society of Canada 171, 287-300, 1997; e. g. Green Guard® SC from BASF Agricultural Specialties Pty Ltd, Australia), *Metschnikowia fructicola* 277 isolated from the surface of grape berries (cv. Superior) grown in the central part of Israel (U.S. Pat. No. 6,994,849; NRRL Y-30752; e. g. Shemer® from Agrogreen, Israel, now distributed by Bayer CropSciences, Germany), *Microdochium dimerum* L13 (CNCM I-3141; e. g. Antibot® from Agrauxine, France), *Microsphaeropsis ochracea* P130A isolated from apple leaves from an abandoned orchard, St-Joseph-du-Lac, Quebec, Canada in 1993 (ATCC 74412; Mycologia 94(2), 297-301, 2002), *Muscodor albus* QST 20799 also called 620 originally isolated from the bark of a cinnamon tree in Honduras (NRRL 30547; e. g. Muscudor™ or QRD300 from AgraQuest, USA), *Muscodor albus* SA-13 (NRRL B-50774; US 2014/0086879 A1; e. g. MBI-601-EP from Marrone BioInnovations, Inc., USA), Neem oil (e. g. Trilogy®, Triact® 70 EC from Certis LLC, USA), *Nomuraea rileyi* strains SA86101, GU87401, SR86151, CG128 and VA9101 (Braz. Arch. Biol. Technol. 46(1), 13-19, 2003; WO 2013/110594), *Paecilomyces lilacinus* 251 isolated from infected nematode eggs in the Philippines (AGAL 89/030550; WO1991/02051; Crop Protection 27, 352-361, 2008; e. g. BioAct®/MeloCon® from Prophyta, Germany), *P. lilacinus* DSM 15169 (e. g. Nemata® SC from Live Systems Technology S.A., Colombia), *P. lilacinus* BCP2 (NRRL 50756; Acta agriculturae Slovenica, 101-2, 263-275, 2013; e. g. PL Gold from BASF Agricultural Specialities (Pty) Ltd., South Africa), *Paenibacillus alvei* NAS6G6 (WO 2014/029697; NRRL B-50755; e.g. BAC-UP from BASF Agricultural Specialities (Pty) Ltd., South Africa in mixture with *Bacillus pumilus* KFP9F), *P. polymyxa* PKB1 (ATCC 202127; Can. J. Microbiol. 48(2), 159-169, 2002), *Pantoea agglomerans* E325 (NRRL B-21856; Phytopathol. 101 (10), 1234-41, 2011; Trees 26, 227-238, 2012; Bloomtime Biological™ from Northwest Agricultural Products, Inc., USA), *Pantoea vagans* (formerly *agglomerans*) C9-1 originally isolated in 1994 from apple stem tissue for control of fire blight in apple (J. Bacteriol. 192(24), 6486-6487, 2010; e. g. BlightBan C9-1® from NuFrams America Inc., USA), *Pasteuria* sp. ATCC PTA-9643 (WO 2010/085795), *Pasteuria* sp. Ph3 isolated from turfgrass soil samples collected at the DeBary Golf Course in central Florida (ATCC SD-5832; WO 2012/064527; for control of *Hoplolaimus galeatus* nematode from *Pasteuria* Bioscience, Inc. now Syngenta Crop Protection, LLC, USA), *Pasteuria* sp. Pr3 isolated from soil samples collected in the south-eastern United States (ATCC SD-5834; for control of *Rotylenchulus reniformis* nematode potentially of species *P. ramosa*; Naviva® ST from Syngenta Crop Protection, LLC, USA), *P. nishizawae* (WO 2010/80619), *P. nishizawae* Pn1 (Federal Register 76(22), 5808, Feb. 2, 2011; ATCC SD-5833; e.g. Clariva™ PN from Syngenta Crop Protection, LLC, USA), *P. penetrans* (U.S. Pat. No. 5,248,500; Del Monte Corp.), *P. ramosa* (WO 2010/080619), *P. thornea* (WO 2010/080619), *P. usgae* BL1 (ATCC SD-5835; J. Nematol. 42(2): 87-90, 2010; ibid. 43(2), 101-109, 2011; e. g. Econem™ for control of *Belonolaimus longicaudatus* from *Pasteuria* BioScience now Syngenta sold by Harell's LLC, Florida, USA for use on turf for management of *Belonolaimus longicaudatus*), *Penicillium bilaiae* (also called *P. bilaii*) strains ATCC 18309 (=ATCC 74319), ATCC 20851 and/or ATCC 22348 (=ATCC 74318) originally isolated from soil in southern Alberta (Fertilizer Res. 39, 97-103, 1994; Can. J. Plant Sci. 78(1), 91-102, 1998; U.S. Pat. No. 5,026,417, WO 1995/017806; e. g. Jump Start®, Provide® from Novozymes Biologicals BioAg Group, Canada), *P. bilaiae* NRRL 50162 and NRRL 50169 (WO 2010/037228), *Phlebiopsis gigantea* (e. g. RotStop® from Verdera Oy, Finland), *Pichia anomala* WRL-076 (NRRL Y-30842; U.S. Pat. No. 8,206,972), potassium bicarbonate (e. g. Amicarb® from Stähler S A, Switzerland), potassium silicate (e. g. Sil-MATRIX™ from Certis LLC, USA), *Pseudozyma flocculosa* PF-A22 UL (e. g. Sporodex® L from Plant Products Co. Ltd., Canada), *Pseudomonas* sp. Proradix (DSM 13134; WO 2001/40441, e. g. PRORADIX from Sourcon Padena GmbH & Co. KG, Hechinger Str. 262, 72072 Tuibingen, Germany), *P. chloraphis* MA 342 (Microbiology Monographs 18, 21-43, 2011; e. g. Cerall® or Cedemon® from BioAgri AB, Uppsala, Sweden or Intrachem Bio Deutschland GmbH & Co. KG, Bad Camberg, Germany), *P. fluorescens* (e.g. in Bio Cure-B from T. Stanes & Company Limited, India; or in Blight-End from Agri Naturals, Mumbai, India), *P. fluorescens* A506 (Phytopathol 97(2), 244-249, 2007; ATCC 31948; e. g. BlightBan® from NuFarm Americas, Inc., Morrisville, N.C., USA), *P. fluorescens* ATCC 13525 of biovar I=biotype A; originally isolated from pre-filter tanks in England (DSM 50090; registered for use in Canada), *P. fluorescens* CHA0 (Mol. Plant Microbe Interact. 5(1), 4-13, 1992), *P. fluorescens* CL 145A (J. Invertebr. Pathol. 113(1), 104-14, 2013; e. g. Zequanox® from Marrone BioInnovations, Davis, Calif., USA), *P. fluorescens* NCIB 12089 (EP 0210734 A!;

Victus® from Mauri Laboratories, 9 Moorebank Ave., Moorebank, NSW 2170, Australia), *P. fluorescens* Pf-5 isolated from root surface of cotton (ATCC BAA-477), *P. putida* ATCC 202153 (EMBRAPA 63/88 4 B; WO 2004/ 0245865), *Pythium oligandrum* DV 74 (US 2013/0035230; ATCC 38472; e. g. Poyversum® from Remeslo SSRO, Biopreparaty, Czech Rep. and from Gowan, USA), *Reynoutria sachalinensis* extract (EP 0307510 B1; e. g. Regalia® SC from Marrone BioInnovations, Davis, Calif., USA or Milsana® from BioFa AG, Germany), *Rhizobium leguminosarum* bv. *phaseoli* (e. g. RHIZO-STICK from BASF Corp., USA), *R. leguminosarum* bv. *phaseoli* RG-B10 (USDA 9041; from Int. J. Syst. Bacteriol. 46(1), 240-244, 1996; Int. J. Syst. Evol. Microbiol. 50, 159-170, 2000; e. g. Nodulator® Dry Bean in Africa, HiStick NT Dry bean in US, and Nodulator® Dry Bean in Canada from BASF Corp., USA, or BASF Agricultural Specialties Ltd., Canada), *R. l.* bv. *trifolii* CB782 (Nodulaid® peat for Kenya white clover from BASF Agricultural Specialties Pty Ltd, Australia), *R. l.* bv. *trifolii* CC275e (Nodulaid® peat for NZ white clover from BASF Agricultural Specialties Pty Ltd, Australia), *R. l.* bv. *trifolii* CC283b (ICMP 4073b; Proc. New Zealand Grassland Assoc. 56, 101-105, 1994; Microbiol. 153, 3184-3195, 2007; Nodulaid® peat for Caucasian clover from BASF Agricultural Specialties Pty Ltd, Australia), *R. l.* bv. *trifolii* CC1099 (Inoculating Legumes: A Practical Guide, ed. Grain Research and Development Corporation, 2012, ISBN 978-1-921779-45-9; e. g. Nodulaid® peat for sainfoin from BASF Agricultural Specialties Pty Ltd, Australia), *R. l.* bv. *trifolii* RP113-7 (Appl. Environ. Microbiol. 44(5), 1096-1101, 1982; e. g. Dormal® from BASF Corp., USA), *R. l.* bv. *trifolii* TA1 (Appl. Environ. Microbiol. 49(1), 127-131, 1985; e. g. Nodulaid® peat for white clover from BASF Agricultural Specialties Pty Ltd, Australia), *R. l.* bv. *trifolii* strain WSM1325 isolated in 1993 from the Greek Island of Serifos (Stand. Genomic Sci. 2(3), 347-356, 2010; Inoculating Legumes: A Practical Guide, ed. Grain Research and Development Corporation, 2012, ISBN 978-1-921779-45-9; Nodulaid® peat for sub clover and Nodulator® granules for sub clover both from BASF Agricultural Specialties Pty Ltd, Australia, for a broad range of annual clovers of Mediterranean origin), *R. l.* bv. *trifolii* strain WSM2304 isolated from *Trifolium polymorphum* in Uruguay in 1998 (Stand. Genomic Sci. 2(1), 66-76, 2010), *R. l.* bv. *viciae* P1NP3Cst being a Streptomycin-resistant mutant of P1 NP3C isolated from pea root nodules in Bretenière, France (also referred to as 1435; New Phytol. 176, 680-690, 2007; ibid. 179(1), 224-235, 2008; e. g. Nodulator® PL Peat Granule from BASF Corp., USA; or Nodulator® XL PL from BASF Agricultural Specialties Ltd., Canada), *R. l.* bv. *viciae* RG-P2 also called P2 isolated from pea root nodules in Sakatchewan, Canada (e. g RhizUP peat for peas and lentils in Canada from BASF Agricultural Specialties Ltd., Canada), *R. l.* bv. *viciae* SU303 (e. g. Nodulaid® Group E from BASF Agricultural Specialties Pty Ltd, Australia), *R. l.* bv. *viciae* WSM1455 (e. g. Nodulaid® Group F from BASF Agricultural Specialties Pty Ltd, Australia), *R. tropici* CC511 (Agronomy, N.Z. 36, 4-35, 2006; e. g. Nodulaid® peat for common bean from BASF Agricultural Specialties Pty Ltd, Australia) *R. tropici* CIAT 899 isolated in Colombia (SEMIA 4077; Rev. Ciênc. Agron. 44(4) Fortaleza October/ December 2013; e. g. Nitrafix® FEIJÃO peat for beans from BASF Agricultural Specialties Ltd., Brazil in mixture with strain SEMIA 4080), *R. tropici* H12 isolated in Planaltina, DF, Cerrados, Brazil (SEMIA 4088; Appl. Microbiol. Biotechnol. 93(5), 2035-49, 2012; e. g. Nitrafix® FEIJÃO from BASF Agricultural Specialties Ltd., Brazil), *R. tropici* PRF 81 isolated in Paraná, Brazil (SEMIA 4080; Soil Biology & Biochemistry 39, 867-876, 2007; BMC Microbiol. 12, 84, 2012; Nitrafix® FEIJÃO peat for beans from BASF Agricultural Specialties Ltd., Brazil in mixture with strain SEMIA 4077), *Sinorhizobium meliloti* RCR2011 also called 2011 or SU47 (MSDJ0848; Mol. Gen. Genomics 272, 1-17, 2004; e. g. Dormal® Alfalfa & Luzerne from BASF Corp., USA; Nitragin® Gold from Novozymes Biologicals BioAg Group, Canada), *Sphaerodes mycoparasitica* SMCD2220 also called SMCD2220-01 (IDAC 301008-01; WO 2011/ 022809), *Spodoptera littoralis* nucleopolyhedrovirus (SpliNPV) (e.g. in LITTOVIR from Andermatt Biocontrol, Switzerland), *Steinernema carpocapsae* (e. g. Millenium® from BASF Agricultural Specialities Limited, UK), *S. feltiae* (Nemashield® from BioWorks, Inc., USA; Nemasys® from BASF Agricultural Specialities Limited, UK), *S. kraussei* L137 (Nemasys® L from BASF Agricultural Specialities Limited, UK), *Streptomyces galbus* AQ6047 (NRRL 30232; WO 2012/135763; AgraQuest now Bayer CropScience LP, USA); *S. galbus* M1064 (NRRL 50334; WO 2012/135763; AgraQuest now Bayer CropScience LP, USA); *S. griseoviridis* K61 (Crop Protection 25, 468-475, 2006; e. g. Mycostop® from Verdera Oy, Espoo, Finland), *S. lydicus* WYEC 108 (U.S. Pat. No. 5,403,584; e. g. Actinovate® from Natural Industries, Inc., USA), *S. violaceusniger* YCED-9 (U.S. Pat. No. 5,968,503; e. g. DT-9® from Natural Industries, Inc., USA), *Talaromyces flavus* V117b isolated from soil (e. g. Protus® WG from Prophyta, Germany), *Trichoderma asperellum* SKT-1 isolated from the rhizosphere of Japanese lawngrass (FERM P-16510; J. Gen. Plant Pathol. 71(5), 351-356, 2005; e. g. Eco-Hope® from Kumiai Chemical Industry Co., Ltd., Japan), *T. asperellum* ICC 012 isolated from a soil in central Italy that was found to suppress plant disease (IMI 392716; e. g. Tenet WP, Remdier WP or Bioten WP from Isagro NC, USA, Bio-Tam™ from AgraQuest, USA), *T. asperellum* TV1 formerly *T. viride* (MUCL 43093; e. g. *T. viride* TV1 from Agribiotec srl, Italy or Xedavir from Xeda Italia, Italy), *T. atroviride* LC52 (e. g. Sentinel® from Agrimm Technologies Ltd, NZ), *T. atroviride* CNCM I-1237 (e. g. Esquive® WG from Agrauxine S.A., France, e. g. against pruning wound diseases on vine and plant root pathogens), *T. fertile* JM41R (NRRL 50759; e. g. Trichoplus™ from BASF Agricultural Specialities (Pty) Ltd., South Africa), *T. gamsii* ICC 080 (IMI 392151; e. g. Tenet WP, Remdier WP, Bioten WP from Isagro NC, USA, Bio-Tam™ from AgraQuest, USA), *T. harzianum* T-22 also called KRL-AG2 (ATCC 20847; BioControl 57, 687-696, 2012; e. g. Plantshield® from BioWorks Inc., USA or SabrEx™ from Advanced Biological Marketing Inc., Van Wert, Ohio, USA), *T. harzianum* T-35 and T-315 (ATCC 20691; EP 0133878 B1; e. g. Root Pro® from Mycontrol Ltd., Israel), *T. harzianum* T-39 (CNCM I-952; EP 0466133 B2; e. g. Trichodex® or *Trichoderma* 2000® from Mycontrol Ltd., Israel and Makhteshim Ltd., Israel), mixture of *T. harzianum* and *T. viride* (e. g. Trichopel® from Agrimm Technologies Ltd, NZ), mixture of *T. harzianum* ICC012 and *T. viride* ICC080 (e. g. Remdier® WP from Isagro Ricerca, Italy), *T. polysporum* IMI 206039 (ATCC 20476; e. g. Binab® from BINAB Bio-Innovation AB, Sweden in mixture with *T. atroviride* IMI 206040), *T. stromaticum* (e. g. Tricovab® from C.E.P.L.A.C., Brazil), *T. virens* G1-3 also called G1-3 or GL-3 (CA 2471555 A1; ATCC 58678; e.g. QuickRoots™ from TJ Technologies, Watertown, S. Dak., USA in mixture with *B. amyloliquefaciens* TJ1000), *T. virens* GL-21 also called G1-21 isolated from a sclerotium of *Sclerotinia minor* (U.S. Pat. No. 7,429,477; e. g. Soilguard® 12G from Certis LLC, USA; EPA Registration Number: 70051-3 and EPA Establishment Number: 067250-IL-001), *T. virens* G-41 also called 041, #41X or ABM 127 isolated from soil samples taken from *Aphanomyces*-suppressive bean fields in Livingston County, N.Y. (ATCC 20906; U.S. Pat. No. 4,996,157; e. g. Rootshield® PLUS from BioWorks, Inc., USA), *T. viride* (J. Biological Control 23(1), 31-36, 2009; e. g. Trieco® from Ecosense Labs. (India) Pvt. Ltd., India; or Bio-Cure® F from T. Stanes & Co. Ltd., India), and *Ulocladium oudemansii* HRU3 (Agronomy 3, 632-647, 2013; e. g. Botry-Zen® from Botry-Zen Ltd, NZ).

Strains can be obtained from culture collections and deposition centers (listed by their acronym=strain prefix here: http://www.wfcc.info/ccinfo/collection/by_acronym/) such as strains with prefaces AGAL or NMI from: National Measurement Institute, 1/153 Bertie Street, Port Melbourne, Victoria, Australia 3207; ATCC: American Type Culture Collection, 10801 University Blvd., Manassas, Va. 20110-2209, USA; BR: Embrapa Agrobiology Diazothrophic Microbial Culture Collection, P.O. Box 74.505, Seropedica, Rio de Janeiro, 23.851-970, Brazil; CABI or IMI: CABI Europe—International Mycological Institute, Bakeham Lane, Egham, Surrey, TW20 9TYNRRL, UK; CB: The CB *Rhizobium* Collection, School of Environment and Agriculture, University of Western Sydney, Hawkesbury, Locked Bag 1797, South Penrith Distribution Centre, NSW 1797, Australia; CBS: Centraalbureau voor Schimmelcultures, Fungal Biodiversity Centre, Uppsalaan 8, PO Box 85167, 3508 AD Utrecht, Netherlands; CC: Division of Plant Industry, CSIRO, Canberra, Australia; CNCM: Collection Nationale de Cultures de Microorga-nismes, Institute Pasteur, 25 rue du Docteur Roux, F-75724 PARIS Cedex 15; CPAC: Embra-pa-Cerrados, CX.Postal 08223, Planaltina, DF, 73301-970, Brazil; DSM: Leibniz-Institut DSMZ-Deutsche Sammlung von Mikroorganismen und Zellkulturen GmbH, Inhoffenstraβe 7 B, 38124 Braunschweig, Germany; IDAC: International Depositary Authority of Canada Collection, Canada; ICMP: Interntional Collection of Micro-organisms from Plants, Landcare Research, Private Bag 92170, Auckland Mail Centre, Auckland 1142, New Zealand; IITA: IITA, PMB 5320, Ibadan, Nigeria; INTA: Agriculture Collection Laboratory of the Instituto de Microbiologia y Zoologia Agricola (IMYZA), Instituto Nacional de Tecnologi'a Agropecuaria (INTA), Castelar, Argentina; MSDJ: Laboratoire de Microbiologie des Sols, INRA, Dijon, France; MUCL: Mycothèque de I'Université catholique de Louvain, Croix du Sud 2, box L7.05.06, 1348 Louvain-la-Neuve, Belgium; NCIMB or NICB: The National Collections of Industrial and Marine Bacteria Ltd., Torry Research Station, P.O. Box 31, 135 Abbey Road, Aberdeen, AB9 8DG, Scotland; Nitragin: Nitragin strain collection, The Nitragin Company, Milwaukee, Wis., USA, NRRL or ARSEF (collection of entomopathogenic fungi): ARS Culture Collection of the National Center for Agricultural Utilization Research, Agricultural Research Service, U.S. Department of Agriculture, 1815 North University Street, Peoria, Ill. 61604, USA; NZP: Department of Scientific and Industrial Research Culture Collection, Applied Biochemistry Division, Palmerston North, New Zealand; PPRI: ARC-Plant Protection Research Institute, Private Bag X134, Queenswood Pretoria, Gauteng, 0121, South Africa; SEMIA: FEPAGRO-Fundagção Estadual de Pesquisa Agropecuária, Rua Gonçalves Dias, 570, Bairro Menino Deus, Porto Alegre/RS, Brazil; SRDI: SARDI, Adelaide, South Australia; USDA: U.S. Department of Agriculture, Agricultural Research Service, Soybean and Alfalfa Research Laboratory, BARC-West, 10300 Baltimore Boulevard, Building 011, Beltsville, Md. 20705, USA (Beltsville Rhiz. Cult. Catalog: http://pdf.usaid.gov/pdf_docs/PNAAW891.pdf); and WSM: Murdoch University, Perth, Western Australia. Further strains may be found at: http://gcm.wfcc.info/; http://www.landcareresearch.co.nz/resources/collections/icmp.

Jasmonic acid, its salts (jasmonates) or derivatives include without limitation potassium, sodium, lithium, ammonium, dimethylammonium, isopropylammonium, diolammonium and diethtriethanolammonium jasmonate; and also jasmonic acid methyl ester, jasmonic acid amide, jasmonic acid methylamide, jasmonic acid-L-amino acid (amide-linked) conjugates (e. g. conjugates with L-isoleucine, L-valine, L-leucine, or L-phenylalanine), 12-oxo-phytodienoic acid, coronatine, coronalon, coronafacoyl-L-serine, coronafacoyl-L-threonine, methyl esters of 1-oxo-indanoyl-isoleucine, methyl esters of 1-oxo-indanoyl-leucine, cis-jasmone, linoleic acid or derivatives thereof, and combinations of any of the above.

According to one embodiment of the inventive mixtures, the component 2) is a biopesticide II from the groups D) to I) selected from:

D) Microbial pesticides with fungicidal, bactericidal, viricidal and/or plant defense activator activity: *Bacillus* altitudinis 41KF2b, *Bacillus amyloliquefaciens* AP-136, *B. amyloliquefaciens* AP-188, *B. amyloliquefaciens* AP-218, *B. amyloliquefaciens* AP-219, *B. amyloliquefaciens* AP-295, *B. amyloliquefaciens* IN937a, *B. amyloliquefaciens* IT-45, *B. amyloliquefaciens* ssp. *plantarum* D747, *B. amyloliquefaciens* ssp. *plantarum* MBI600 (NRRL B-50595), *B. amyloliquefaciens* ssp. *plantarum* TJ1000, *B. mojavensis* AP-209, *B. mycoides* AQ726, *B. mycoides* strain J, *B. pumilus* INR-7, *B. pumilus* GHA 180, *B. simplex* ABU 288, *B. solisalsi* AP-217, *B. subtilis* CX-9060, *B. subtilis* FB17, *B. subtilis* GB07, *Clavibacter michiganensis* (bacteriophages), *Gliocladium roseum* 321U, *Microsphaeropsis ochracea* P130A, *Muscodor albus* QST 20799, *Muscodor albus* SA-13, *Paenibacillus alvei* NAS6G6, *Paenibacillus polymyxa* PKB1, *Pantoea agglomerans* E325, *Pantoea vagans* C9-1, *Penicillium bilaiae* ATCC 22348, *P. bilaiae* ATCC 20851, *Penicillium bilaiae* ATCC 18309, *Phlebiopsis gigantea*, *Pichia anomala* WRL-76, *Pseudomonas* sp. Proradix, *Pseudomonas chloraphis* MA 342, *P. fluorescens* A506, *P. fluorescens* CL 145A, *P. fluorescens* NCIB 12089, *P. fluorescens* Pf-5, *P. fluorescens* WCS 374, *P. fluorescens* ATCC 13525, *P. fluorescens* CHA0, *P. putida* ATCC 202153, *Sphaerodes mycoparasitica* SMCD2220, *S. lydicus* WYEC 108, *S. violaceusniger* XL-2, *S. violaceusniger* YCED-9, *Trichoderma fertile* JM41R, *Typhula phacorrhiza* 94671, *Verticillium dahlia*, zucchini yellow mosaic virus (avirulent strain);

E) Biochemical pesticides with fungicidal, bactericidal, viricidal and/or plant defense activator activity: harpin protein, laminarin, Menhaden fish oil, natamycin, Plum pox virus coat protein, potassium bicarbonate, salicylic acid, potassium or sodium bicarbonate, tea tree oil;

F) Microbial pesticides with insecticidal, acaricidal, molluscidal and/or nematicidal activity: *Agrobacterium radiobacter* K1026, *A. radiobacter* K84, *Bacillus firmus* I-1582; *B. thuringiensis* ssp. *aizawai* strains: ABTS-1857, SAN 401 I, ABG-6305 and ABG-6346; *B. t.* ssp. *israelensis* AM65-52, *B. t.* ssp. *israelensis* SUM-6218, *B. t.* ssp. *galleriae* SDS-502, *B. t.* ssp. *kurstaki* EG 2348, *B. t.* ssp. *kurstaki* SB4, *B. t.* ssp. *kurstaki* ABTS-351 (HD-1), *Beauveria bassiana* ATCC 74040, *B. bassiana* GHA, *B. bassiana* H123, *B. bassiana* DSM 12256, *B. bassiana*

PPRI 5339, *B. brongniartii*, *Burkholderia* sp. A396, *Chromobacterium subtsugae* PRAA4-1, *Cydia pomonella* granulosis virus V22, *Cydia pomonella* granulosis virus V1, *Cryptophlebia leucotreta* granulovirus (CrleGV), *Flavobacterium* sp. H492, *Helicoverpa armigera* nucleopolyhedrovirus (HearNPV), *Isaria fumosorosea* Apopka-97, *Lecanicillium longisporum* KV42, *L. longisporum* KV71, *L. muscarium* KV01, *Metarhizium anisopliae* FI-985, *M. anisopliae* FI-1045, *M. anisopliae* F52, *M. anisopliae* ICIPE 69, *M. anisopliae* var. *acridum* IMI 330189; *Nomuraea rileyi* strains: SA86101, GU87401, SR86151, CG128 and VA9101; *Paecilomyces fumosoroseus* FE 9901, *P. lilacinus* 251, *P. lilacinus* DSM 15169, *P. lilacinus* BCP2, *Paenibacillus popilliae* Dutky-1940 (NRRL B-2309=ATCC 14706), *P. popilliae* Dutky 1, *P. popilliae* KLN 3, *Pasteuria* sp. Ph3, *Pasteuria* sp. ATCC PTA-9643, *Pasteuria* sp. ATCC SD-5832, *P. nishizawae* Pn1, *P. penetrans*, *P. ramosa*, *P.* sp. Pr-3, *P. thornea*, *P. usgae*, *Pseudomonas fluorescens* CL 145A, *Spodoptera littoralis* nucleopolyhedrovirus (SpliNPV), *Steinernema carpocapsae*, *S. feltiae*, *S. kraussei* L137;

G) Biochemical pesticides with insecticidal, acaricidal, molluscidal, pheromone and/or nematicidal activity: L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, cis-jasmone, lavanulyl senecioate, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, R-1-octen-3-ol, pentatermanone, potassium silicate, sorbitol actanoate, (E,Z,Z)-3,8,11-tetradecatrienyl acetate, (Z,E)-9,12-tetradecadien-1-yl acetate, Z-7-tetradecen-2-one, Z-9-tetradecen-1-yl acetate, Z-11-tetradecenal, Z-11-tetradecen-1-ol, *Acacia negra* extract, extract of grapefruit seeds and pulp, extract of *Chenopodium ambrosiodes*, Catnip oil, Neem oil, Quillay extract, Tagetes oil;

H) Microbial pesticides with plant stress reducing, plant growth regulator, plant growth promoting and/or yield enhancing activity: *Azospirillum amazonense* BR 11140 (SpY2), *A. brasilense* Ab-V5, *A. brasilense* Ab-V6, *A. brasilense* AZ39, *A. brasilense* XOH, *A. brasilense* Sp245 (BR 11005), *A. brasilense* BR 11002, *A. lipoferum* BR 11646 (Sp31), *A. irakense*, *A. halopraeferens*, *Bradyrhizobium* sp. PNL01, *B.* sp. (*Arachis*) CB1015, *B.* sp. (*Arachis*) USDA 3446, *B.* sp. (*Arachis*) SEMIA 6144, *B.* sp. (*Arachis*) SEMIA 6462, *B.* sp. (*Arachis*) SEMIA 6464, *B.* sp. (*Vigna*), *B. elkanii* SEMIA 587, *B. elkanii* SEMIA 5019, *B. elkanii* U-1301, *B. elkanii* U-1302, *B. elkanii* USDA 74, *B. elkanii* USDA 76, *B. elkanii* USDA 94, *B. elkanii* USDA 3254, *B. japonicum* 532c, *B. japonicum* CPAC 15, *B. japonicum* E-109, *B. japonicum* G49, *B. japonicum* TA-11, *B. japonicum* USDA 3, *B. japonicum* USDA 31, *B. japonicum* USDA 76, *B. japonicum* USDA 110, *B. japonicum* USDA 121, *B. japonicum* USDA 123, *B. japonicum* USDA 136, *B. japonicum* SEMIA 566, *B. japonicum* SEMIA 5079, *B. japonicum* SEMIA 5080, *B. japonicum* WB74, *B. liaoningense*, *B. lupini* LL13, *B. lupini* WU425, *B. lupini* WSM471, *B. lupini* WSM4024, *Glomus intraradices* RTI-801, *Mesorhizobium* sp. WSM1271, *M.* sp. WSM1497, *M. ciceri* CC1192, *M. huakii*, *M. loti* CC829, *M. loti* SU343, *Rhizobium leguminosarum* bv. *phaseoli* RG-B10, *R. l.* bv. *trifolii* RP113-7, *R. l.* bv. *trifolii* 095, *R. l.* bv. *trifolii* TA1, *R. l.* bv. *trifolii* CC283b, *R. l.* bv. *trifolii* CC275e, *R. l.* bv. *trifolii* CB782, *R. l.* bv. *trifolii* CC1099, *R. l.* bv. *trifolii* WSM1325, *R. l.* bv. *viciae* SU303, *R. l.* bv. *viciae* WSM1455, *R. l.* bv. *viciae* P1NP3Cst, *R. l.* bv. *viciae* RG-P2, *R. tropici* PRF 81, *R. tropici* SEMIA 4077, *R. tropici* CC511(L.5.70), *Sinorhizobium meliloti* RCR2011, *S. meliloti* NRG185, *S. meliloti* RR1128;

I) Biochemical pesticides with plant stress reducing, plant growth regulator and/or plant yield enhancing activity: abscisic acid, aluminium silicate (kaolin), 3-decen-2-one, formononectin, genistein, hesperetin, homobrassinolide, humates, methyl jasmonate, cis-jasmone, lysophosphatidyl ethanlamine, naringenin, polymeric polyhydroxy acid, salicylic acid, *Ascophyllum nodosum* (Norwegian kelp, Brown kelp) extract and *Ecklonia maxima* (kelp) extract.

*Bacillus amyloliquefaciens* subsp. *plantarum* MBI600 as biopesticide II having the accession number NRRL B-50595 is deposited with the United States Department of Agriculture on Nov. 10, 2011 under the strain designation *Bacillus subtilis* 1430. It has also been deposited at The National Collections of Industrial and Marine Bacteria Ltd. (NCIB), Torry Research Station, P.O. Box 31, 135 Abbey Road, Aberdeen, AB9 8DG, Scotland under accession number 1237 on Dec. 22, 1986. *Bacillus amyloliquefaciens* MBI600 is known as plant growth-promoting rice seed treatment from Int. J. Microbiol. Res. ISSN 0975-5276, 3(2) (2011), 120-130 and further described e.g. in US 2012/0149571 A1. This strain MBI600 is commercially available as liquid formulation product Integral® (Becker-Underwood Inc., USA).

*Metarhizium anisopliae* IMI33 is commercially available from Becker Underwood as product Green Guard. *M. anisopliae* var *acridium* strain IMI 330189 (NRRL-50758) is commercially available from Becker Underwood as product Green Muscle.

According to one embodiment of the inventive mixtures, the at least one biopesticide II is *Bacillus amyloliquefaciens* subsp. *plantarum* MBI600. These mixtures are particularly suitable in soybean.

According to another embodiment of the inventive mixtures, the at least one biopesticide II is *B. pumilus* strain INR-7 (otherwise referred to as BU-F22 (NRRL B-50153) and BU-F33 (NRRL B-50185). These mixtures are particularly suitable in soybean and corn.

According to another embodiment of the inventive mixtures, the at least one biopesticide II is *Bacillus simplex*, preferably *B. simplex* strain ABU 288 (NRRL B-50340). These mixtures are particularly suitable in soybean and corn.

According to another embodiment of the inventive mixtures, the at least one biopesticide II is *Trichoderma fertile* strain JM41R. These mixtures are particularly suitable in soybean and corn.

According to another embodiment of the inventive mixtures, the at least one biopesticide II is *Sphaerodes mycoparasitica*, preferably *Sphaerodes mycoparasitica* strain IDAC 301008-01 (also referred to as strain SMCD2220-01). These mixtures are particularly suitable in soybean and corn.

According to another embodiment of the inventive mixtures, the at least one biopesticide II is *Beauveria bassiana*, preferably *Beauveria bassiana* strain PPRI5339. These mixtures are particularly suitable in soybean and corn.

According to another embodiment of the inventive mixtures, the at least one biopesticide II is *Metarhizium anisopliae* or *M. anisopliae* var. *acridium*, preferably selected from *M anisolpiae* strain IMI33 and *M. anisopliae* var. *acridium* strain IMI 330189. These mixtures are particularly suitable in soybean and corn.

According to another embodiment of the inventive mixtures, *Bradyrhizobium* sp. (meaning any *Bradyrhizobium* species and/or strain) as biopesticide II is *Bradyrhizobium japonicum* (*B. japonicum*). These mixtures are particularly suitable in soybean. Preferably *B. japonicum* is not one of the strains TA-11 and/or 532c. *B. japonicum* strains were cultivated using media and fermentation techniques known in the art, e.g. in yeast extract-mannitol broth (YEM) at 27° C. for about 5 days.

References for various *B. japonicum* strains are given e.g. in U.S. Pat. No. 7,262,151 (*B. japonicum* strains USDA 110 (=IITA 2121, SEMIA 5032, RCR 3427, ARS I-110, Nitragin 61A89; isolated from *Glycine max* in Florida in 1959, Serogroup 110; Appl Environ Microbiol 60, 940-94, 1994), USDA 31 (=Nitragin 61A164; isolated from *Glycine max* in Wisconsin in 1941, USA, Serogroup 31), USDA 76 (plant passage of strain USDA 74 which has been isolated from *Glycine max* in California, USA, in 1956, Serogroup 76), USDA 121 (isolated from *Glycine max* in Ohio, USA, in 1965), USDA 3 (isolated from *Glycine max* in Virginia, USA, in 1914, Serogroup 6) and USDA 136 (=CB 1809, SEMIA 586, Nitragin 61A136, RCR 3407; isolated from *Glycine max* in Beltsville, Md. in 1961; Appl Environ Microbiol 60, 940-94, 1994). USDA refers to United States Department of Agriculture Culture Collection, Beltsville, Md., USA (see e.g. Beltsville *Rhizobium* Culture Collection Catalog March 1987 ARS-30). Further suitable *B. japonicum* strain G49 (INRA, Angers, France) is described in Fernandez-Flouret, D. & Cleyet-Marel, J. C. (1987) C R Acad Agric Fr 73, 163-171), especially for soybean grown in Europe, in particular in France. Further suitable *B. japonicum* strain TA-11 (TA11 NOD$^+$) (NRRL B-18466) is i.a. described in U.S. Pat. No. 5,021,076; Appl Environ Microbiol (1990) 56, 2399-2403 and commercially available as liquid inoculant for soybean (VAULT® NP, Becker Underwood, USA). Further *B. japonicum* strains as example for biopesticide II are described in US2012/0252672A. Further suitable and especially in Canada commercially available strain 532c (The Nitragin Company, Milwaukee, Wis., USA, field isolate from Wisconsin; Nitragin strain collection No. 61A152; Can J Plant Sci 70 (1990), 661-666).

Other suitable and commercially available *B. japonicum* strains (see e.g. Appl Environ Microbiol 2007, 73(8), 2635) are SEMIA 566 (isolated from North American inoculant in 1966 and used in Brazilian commercial inoculants from 1966 to 1978), SEMIA 586 (=CB 1809; originally isolated in Maryland, USA but received from Australia in 1966 and used in Brazilian inoculants in 1977), CPAC 15 (=SEMIA 5079; a natural variant of SEMIA 566 used in commercial inoculants since 1992) and CPAC 7 (=SEMIA 5080; a natural variant of SEMIA 586 used in commercial inoculants since 1992). These strains are especially suitable for soybean grown in Australia or South America, in particular in Brazil. Some of the abovementioned strains have been re-classified as a novel species *Bradyrhizobium elkanii*, e.g. strain USDA 76 (Can. J. Microbiol., 1992, 38, 501-505).

Another suitable and commercially available *B. japonicum* strain is E-109 (variant of strain USDA 138, see e.g. Eur. J. Soil Biol. 45 (2009) 28-35; Biol Fertil Soils (2011) 47:81-89, deposited at Agriculture Collection Laboratory of the Instituto de Microbiologia y Zoologia Agricola (IMYZA), Instituto Nacional de Tecnologi'a Agropecuaria (INTA), Castelar, Argentina). This strain is especially suitable for soybean grown in South America, in particular in Argentina.

The present invention also relates to mixtures, wherein the at least one biopesticide II is selected from *Bradyrhizobium elkanii* and *Bradyrhizobium liaoningense* (*B. elkanii* and *B. liaoningense*), more preferably from *B. elkanii*. These mixtures are particularly suitable in soybean. *B. elkanii* and liaoningense were cultivated using media and fermentation techniques known in the art, e.g. in yeast extract-mannitol broth (YEM) at 27° C. for about 5 days.

Suitable and commercially available *B. elkanii* strains are SEMIA 587 and SEMIA 5019 (=29 W) (see e.g. Appl Environ Microbiol 2007, 73(8), 2635) and USDA 3254 and USDA 76 and USDA 94. Further commercially available *B. elkanii* strains are U-1301 and U-1302 (e. g. product Nitroagin® Optimize from Novozymes Bio As S.A., Brazil or NITRASEC for soybean from LAGE y Cia, Brazil). These strains are especially suitable for soybean grown in Australia or South America, in particular in Brazil.

The present invention also relates to mixtures, wherein the at least one biopesticide II is selected from *Bradyrhizobium japonicum* (*B. japonicum*) and further comprises a compound III, wherein compound III is selected from jasmonic acid or salts or derivatives thereof including cis-jasmone, preferably methyl-jasmonate or cis-jasmone.

The present invention also relates to mixtures, wherein biopesticide II is selected from *Bradyrhizobium* sp. (*Arachis*) (*B*. sp. *Arachis*) which shall describe the cowpea miscellany cross-inoculation group which includes inter alia indigenous cowpea bradyrhizobia on cowpea (*Vigna unguiculata*), siratro (*Macroptilium atropurpureum*), lima bean (*Phaseolus lunatus*), and peanut (*Arachis hypogaea*). This mixture comprising compound I and *B*. sp. *Arachis* is especially suitable for use in peanut, Cowpea, Mung bean, Moth bean, Dune bean, Rice bean, Snake bean and Creeping vigna, in particular peanut.

Suitable and commercially available *B*. sp. (*Arachis*) strain is CB1015 (=IITA 1006, USDA 3446 presumably originally collected in India; from Australian Inoculants Research Group; see e.g. http://www.qaseeds.com.au/inoculant_applic.php; Beltsville *Rhizobium* Culture Collection Catalog March 1987 USDA-ARS ARS-30). These strains are especially suitable for peanut grown in Australia, North America or South America, in particular in Brazil. Further suitable strain is *bradyrhizobium* sp. PNL01 (Becker Underwood; ISO Rep Marita McCreary, QC Manager Padma Somasageran; IDENTIFICATION OF RHIZOBIA SPECIES THAT CAN ESTABLISH NITROGEN-FIXING NODULES IN CROTALARIA LONGIROSTRATA. Apr. 29, 2010, University of Massachusetts Amherst: http://www.wpi.edu/Pubs/E-project/Available/E-project-042810-163614/unrestricted/Bisson.Mason._Identification_of_Rhizobia_Species_That_can_Establish_Nitrogen-Fixing_Nodules_in_Crotalia_Longirostrata.pdf).

Suitable and commercially available *Bradyrhizobium* sp. (*Arachis*) strains especially for cowpea and peanut but also for soybean are *Bradyrhizobium* SEMIA 6144, SEMIA 6462 (=BR 3267) and SEMIA 6464 (=BR 3262) (deposited at FEPAGRO-MIRCEN, R. Gonçalves Dias, 570 Porto Alegre-RS, 90130-060, Brazil; see e.g. FEMS Microbiology Letters (2010) 303(2), 123-131; Revista Brasileira de Ciencia do Solo (2011) 35(3); 739-742, ISSN 0100-0683).

The present invention also relates to mixtures wherein the at least one biopesticide II is selected from *Bradyrhizobium* sp. (*Arachis*) and further comprises a compound III, wherein compound III is selected from jasmonic acid or salts or derivatives thereof including cis-jasmone, preferably methyl-jasmonate or cis-jasmone.

The present invention also relates to mixtures, wherein biopesticide II is selected from *Bradyrhizobium* sp. (*Lupine*) (also called *B. lupini*, *B. lupines* or *Rhizobium lupini*). This mixture is especially suitable for use in dry beans and lupins.

Suitable and commercially available *B. lupini* strain is LL13 (isolated from *Lupinus iuteus* nodules from French soils; deposited at INRA, Dijon and Angers, France; http://agriculture.gouv.fr/IMG/pdf/ch20060216.pdf). This strain is especially suitable for lupins grown in Australia, North America or Europe, in particular in Europe.

Further suitable and commercially available *B. lupini* strains WU425 (isolated in Esperance, Western Australia from a non-Australian legume *Ornthopus compressus*), WSM4024 (isolated from lupins in Australia by CRS during a 2005 survey) and WSM471 (isolated from *Ornithopus pinnatus* in Oyster Harbour, Western Australia) are described e.g. in Palta J. A. and Berger J. B. (eds), 2008, Proceedings 12$^{th}$ International Lupin Conference, 14-18 Sep. 2008, Fremantle, Western Australia. International Lupin Association, Canterbury, New Zealand, 47-50, ISBN 0-86476-153-8: http://www.lupins.org/pdf/conference/2008/Agronomy%20and%20Production/John%20Howieson%20and%20G%20OHara.pdf; Appl Environ Microbiol (2005) 71, 7041-7052 and Australian J. Exp. Agricult. (1996) 36(1), 63-70.

The present invention also relates to mixtures wherein the at least one biopesticide II is selected from *Bradyrhizobium* sp. (*Lupine*) (*B. lupini*) and further comprises a compound III, wherein compound III is selected from jasmonic acid or salts or derivatives thereof including cis-jasmone, preferably methyl-jasmonate or cis-jasmone.

The present invention also relates to mixtures, wherein the at least one biopesticide II is selected from *Mesorhizobium* sp. (meaning any *Mesorhizobium* species and/or strain), more preferably *Mesorhizobium ciceri*. These mixtures are particularly suitable in cowpea.

Suitable and commercially available *M.* sp. strains are e.g. *M. ciceri* CC1192 (=UPM 848, CECT 5549; from Horticultural Research Station, Gosford, Australia; collected in Israel from *Cicer arietinum* nodules; Can J Microbial (2002) 48, 279-284) and *Mesorhizobium* sp. strains WSM1271 (collected in Sardinia, Italy, from plant host *Biserrula pelecinus*), WSM 1497 (collected in Mykonos, Greece, from plant host *Biserrula pelecinus*), *M. loti* strains CC829 (commerical inoculant for *Lotus pedunculatus* and *L. ulginosus* in Australia, isolated from *L. ulginosus* nodules in USA) and SU343 (commercial inoculant for *Lotus corniculatus* in Australia; isolated from host nodules in USA) all of which are deposited at Western Australian Soil Microbiology (WSM) culture collection, Australia and/or CSIRO collection (CC), Canberra, Australian Capirtal Territory (see e.g. Soil Biol Biochem (2004) 36(8), 1309-1317; Plant and Soil (2011) 348(1-2), 231-243).

Suitable and commercially available *M. loti* strains are e.g. *M. loti* CC829 for *Lotus pedunculatus*.

The present invention also relates to mixtures wherein the at least one biopesticide II is selected from *Bradyrhizobium* sp. (*Lupine*) (*B. lupini*) and further comprises a compound III, wherein compound III is selected from jasmonic acid or salts or derivatives thereof including cis-jasmone, preferably methyl-jasmonate or cis-jasmone.

The present invention also relates to mixtures comprising a biopesticide II, wherein biopesticide II is selected from *Mesorhizobium huakuii*, also referred to as *Rhizobium huakuii* (see e.g. Appl. Environ. Microbiol. 2011, 77(15), 5513-5516). These mixtures are particularly suitable in *Astralagus*, e.g. *Astalagus sinicus* (Chinese milkwetch), *Thermopsis*, e.g. *Thermopsis luinoides* (Goldenbanner) and alike. Suitable and commercially available *M. huakuii* strain is HN3015 which was isolated from *Astralagus sinicus* in a rice-growing field of Southern China (see e.g. World J. Microbiol. Biotechn. (2007) 23(6), 845-851, ISSN 0959-3993).

The present invention also relates to mixtures wherein the at least one biopesticide II is selected from *Mesorhizobium huakuii* and further comprises a compound III, wherein compound III is selected from jasmonic acid or salts or derivatives thereof including cis-jasmone, preferably methyl-jasmonate or cis-jasmone.

The present invention also relates to mixtures, wherein the at least one biopesticide II is selected from *Azospirillum amazonense, A. brasilense, A. lipoferum, A. irakense, A. halopraeferens*, more preferably from *A. brasilense*, in particular selected from *A. brasilense* strains BR 11005 (SP 245) and AZ39 which are both commercially used in Brazil and are obtainable from EMBRAPA, Brazil. These mixtures are particularly suitable in soybean.

Humates are humic and fulvic acids extracted from a form of lignite coal and clay, known as leonardite. Humic acids are organic acids that occur in humus and other organically derived materials such as peat and certain soft coal. They have been shown to increase fertilizer efficiency in phosphate and micro-nutrient uptake by plants as well as aiding in the development of plant root systems.

Salts of jasmonic acid (jasmonate) or derivatives include without limitation the jasmonate salts potassium jasmonate, sodium jasmonate, lithium jasmonate, ammonium jasmonate, dimethylammonium jasmonate, isopropylammonium jasmonate, diolammonium jasmonate, diethtriethanolammonium jasmonate, jasmonic acid methyl ester, jasmonic acid amide, jasmonic acid methylamide, jasmonic acid-L-amino acid (amide-linked) conjugates (e.g., conjugates with L-isoleucine, L-valine, L-leucine, or L-phenylalanine), 12-oxo-phytodienoic acid, coronatine, coronafacoyl-L-serine, coronafacoyl-L-threonine, methyl esters of 1-oxo-indanoyl-isoleucine, methyl esters of 1-oxo-indanoyl-leucine, coronalon (2-[(6-ethyl-l-oxo-indane-4-carbonyl)-amino]-3-methyl-pentanoic acid methyl ester), linoleic acid or derivatives thereof and cis-jasmone, or combinations of any of the above. More preferably, jasmonic acid derivatives are selected from jasmonic acid, methyl jasmonate and cis-jasmone.

According to a further embodiment, the mixture comprise as component 3) a biopesticide from group T), preferably selected from abscisic acid, aluminium silicate (kaolin), humates, indole-3-acetic acid, *Ascophyllum nodosum* (Norwegian kelp, Brown kelp) extract and *Ecklonia maxima* (kelp) extract.

The inventive mixtures comprising as biopesticide II a microbial pesticide from groups D), F) and H) may be formulated as an inoculant for a plant. The term "inoculant" means a preparation that includes an isolated culture of a microbial pesticide and optionally a carrier, which may include a biologically acceptable medium.

The abovementioned microbial pesticides may be isolated or substantially purified. The terms "isolated" or "substantially purified" refers to microbial pesticides that have been removed from a natural environment and have been isolated or separated, and are at least 60% free, preferably at least 75% free, and more preferably at least 90% free, even more preferably at least 95% free, and most preferably at least 100% free from other components with which they were naturally associated. An "isolated culture" refers to a culture of the microbial pesticides that does not include significant amounts of other materials such as other materials which normally are found in natural habitat in which the microbial pesticides grows and/or from which the microbial pesticides normally may be obtained. An "isolated culture" may be a culture that does not include any other biological, microorganism, and/or bacterial species in quantities sufficient to interfere with the replication of the "isolated culture." Isolated cultures of microbial pesticides may be combined to prepare a mixed culture of microbial pesticides.

Herein, microbial pesticides may be supplied in any physiological state such as active or dormant. Dormant microbial pesticides may be supplied for example frozen, dried, or lyophilized or partly desiccated (procedures to produce these partly desiccated organisms are given in WO2008/002371) or in form of spores.

Preference is also given to mixtures comprising as biopesticide II (component 2) a biopesticide from group D), preferably selected from *Bacillus amyloliquefaciens* herein even more preferably from strains AP-136, AP-188, AP-218, AP-219, AP-295, IN937a, IT-45; *B. amyloliquefaciens* ssp. *plantarum* herein even more preferably from strains MBI600, D747 and TJ1000; *B. mojavensis* AP-209; *B. pumilus* GHA 180 and INR-7; *B. simplex* herein more preferably strain ABU 288; *B. solisalsi* herein more preferably strain AP-217; *B. subtilis* herein even more preferably selected from strains CX-9060, FB17 and GB07; *Muscodor albus* herein more preferably strains QST 20799 and SA-13; *Paenibacillus alvei* herein more preferably strain NAS6G6, *Paenibacillus polymyxa* herein more preferably strain PKB1, *Penicillium bilaiae* herein more preferably strains ATCC 22348, ATCC 20581 and ATCC 18309; *Pseudomonas fluorescens* herein more preferably strain A506; *Sphaerodes mycoparasitica* herein more preferably strain SMCD2220; *Trichoderma fertile* herein more preferably strain JM41R.

Preference is also given to mixtures comprising as biopesticide II (component 2) a biopesticide from group D), even more preferably selected from even more preferably from *B. amyloliquefaciens* AP-188, *B. amyloliquefaciens* ssp. *plantarum* MBI600, *B. pumilus* INR-7, *B. simplex* ABU 288, *B. subtilis* FB17, *Paenibacillus alvei* NAS6G6 and *Trichoderma fertile* JM41R.

According to one embodiment of the inventive mixtures, the at least one biopesticide II is *Bacillus amyloliquefaciens* ssp. *plantarum* MBI600. These mixtures are particularly suitable in soybean.

According to another embodiment of the inventive mixtures, the at least one biopesticide II is *B. pumilus* INR-7. These mixtures are particularly suitable in soybean and corn.

According to a further embodiment, the at least one biopesticide II is *Bacillus simplex*, preferably *B. simplex* ABU 288. These mixtures are particularly suitable in soybean and corn.

According to a further embodiment, the at least one biopesticide II is *Bacillus subtilis*, preferably *B. subtilis* strain FB17.

According to one embodiment of the inventive mixtures, the at least one biopesticide II is selected from *Bacillus amyloliquefaciens* AP-136, *B. amyloliquefaciens* AP-188, *B. amyloliquefaciens* AP-218, *B. amyloliquefaciens* AP-219, *B. amyloliquefaciens* AP-295, *B. amyloliquefaciens* ssp. *plantarum* TJ1000, *B. amyloliquefaciens* ssp. *plantarum* D747, *B. amyloliquefaciens* ssp. *plantarum* MBI600, *B. mojavensis* AP-209, *B. pumilus* INR-7, *B. pumilus* GHA 180, *B. simplex* ABU 288, *B. solisalsi* AP-217, *B. subtilis* CX-9060, *B. subtilis* FB17 and *B. subtilis* GB07. These mixtures are particularly suitable in soybean and corn, in particular for seed treatment.

According to a further embodiment, the at least one biopesticide II is selected from *Streptomyces* spp., preferably from *S. griseoviridis*, *S. lydicus* and *S. violaceusniger*, in particular from strains *S. griseoviridis* K61, *S. lydicus* WYEC 108, *S. violaceusniger* XL-2 and *S. violaceusniger* YCED-9.

According to a further embodiment, the at least one biopesticide II is selected from *Pseudomonas* spp., preferably selected from *P. chloraphis* herein more preferably strain MA 342 and *Pseudomonas* sp. DSM 13134; *P. fluorescens* herein more preferably selected from strains A506, WCS 374 and Pf-5; and *P. putida* herein more preferably strain ATCC 202153.

The present invention also relates to mixtures wherein the at least one biopesticide II is selected from the fungal species *Muscodor albus* preferably from the strains SA-13 and QST 20799, which are particularly suitable for soil and seed treatment against soil-borne pathogens and/or nematodes.

Preference is also given to mixtures comprising as biopesticide II (component 2) a biopesticide from group L2), preferably selected methyl-jasmonate, cis-jasmone, laminarin, *Reynoutria sachalinensis* extract and tea tree oil; even more preferable from methyl jasmonate, cis-jasmone and laminarin.

Preference is also given to mixtures comprising as biopesticide II (component 2) a biopesticide from group L3), preferably selected from *Agrobacterium radiobacter* herein preferably strain K1026, *Bacillus firmus* herein preferably strain I-1582, *Bacillus thuringiensis* ssp. *kurstaki* herein preferably strain SB4, *Beauveria bassiana* herein preferably selected from strains GHA, H123, DSM 12256 and PPRI 5339; *Burkholderia* sp. and herein preferably strain A396, *Metarhizium anisopliae* var. *acridum* herein preferably strain IMI 330189, *M. anisopliae* herein preferably selected from strains FI-985, FI-1045, F52 and ICIPE 69; *Paecilomyces lilacinus* herein preferably selected from strains 251, DSM 15169 and BCP2, *Paenibacillus popilliae* herein preferably selected from strains Dutky-1940, KLN 3 and Dutky 1; *Pasteuria nishazawa* and herein preferably strain Pn1.

Preference is also given to mixtures comprising as biopesticide II (component 2) a biopesticide from group L3), even more preferably from *Bacillus thuringiensis* ssp. *kurstaki* SB4, *B. bassiana* DSM 12256, *B. bassiana* PPRI 5339, *Metarhizium anisopliae* var. *acridum* IMI 330189, *M. anisopliae* FI-985, *M. anisopliae* FI-1045, *Paecilomyces lilacinus* DSM 15169, *P. lilacinus* BCP2, *P. lilacinus* 251, *Paenibacillus popilliae* Dutky-1940, *P. popilliae* KLN 3 and *P. popilliae* Dutky 1.

According to a further embodiment, the at least one biopesticide II is *Beauveria brongniartii*.

According to a further embodiment, the at least one biopesticide II is *Metarhizium anisopliae* or *M. anisopliae* var. *acridium*, preferably selected from *M. anisopliae* FI-1045, *M. anisopliae* F52, *M. anisopliae* var. *acridum* strains FI-985 and IMI 330189; in particular strain IMI 330189. These mixtures are particularly suitable for control of arthropod pests in soybean and corn.

According to a further embodiment, the at least one biopesticide II is *Lecanicillium* sp., preferably selected from *Lecanicillium longisporum* KV42, *L. longisporum* KV71 and *L. muscarium* KV01.

According to a further embodiment, the at least one biopesticide II is *Paecilomyces fumosoroseus*, preferably strain FE 9901 especially for white fly control.

According to a further embodiment, the at least one biopesticide II is selected from *Nomuraea rileyi*, preferably strains SA86101, GU87401, SR86151, CG128 and VA9101; and *P. lilacinus*, preferably strains 251, DSM 15169 or BCP2, in particular BCP2, which strains especially control the growth of plant-pathogenic nematodes.

According to a further embodiment, the at least one biopesticide II is *Bacillus firmus*, preferably spores of strain CNCM I-1582, preferably useful for seed treatment of soybean and corn against nematodes and insects.

According to a further embodiment, the at least one biopesticide II is *Bacillus cereus*, preferably spores of CNCM I-1562, preferably useful for seed treatment of soybean and corn against nematodes and insects.

According to a further embodiment, the at least one biopesticide II is a mixture of spores of *B. firmus* and *B. cereus*, preferably mixtures spores of above mentioned strains CNCM I-1582 and CNCM I-1562, preferably useful for seed treatment of soybean and corn against nematodes and insects.

According to a further embodiment, the at least one biopesticide II is selected from *Bacillus t.* ssp. *kurstaki* preferably from strains EG 2348, SB4 and ABTS-351 (HD-1), in particular *B. t.* ssp. *kurstaki* SB4. These strains are used for control of lepidopteran larvae, but without noctuidae.

According to one embodiment of the inventive mixtures, the at least one biopesticide II is selected from *Bacillus firmus* CNCM I-1582, *Paecilomyces lilcinus* 251, *Pasteuria nishizawa* Pn1 and *Burkholderia* sp. A396 having nematicidal, acaricidal and/or insecticidal activity. These mixtures are particularly suitable in soybean and corn, in particular for seed treatment.

Preference is also given to mixtures comprising as biopesticide II (component 2) a biopesticide from group L4), preferably selected from methyl jasmonate, Acacia negra extract, extract of grapefruit seeds and pulp, Catnip oil, Neem oil, Quillay extract and Tagetes oil, in particular methyl jasmonate or water-based Quillay extract.

Preference is also given to mixtures comprising as biopesticide II (component 2) a biopesticide from group L5), preferably selected from *Azospirillum amazonense, A. brasilense, A. lipoferum, A. irakense, A. halopraeferens, Bradyrhizobium* sp. (*Arachis*), *Bradyrhizobium* sp. (*Vigna*), *B. elkanii, B. japonicum; Paenibacillus alvei, Penicillium bilaiae, Rhizobium leguminosarum* bv. *phaseoli, R. l.* bv. *trifolii, R. l.* bv. *viciae*, and *Sinorhizobium meliloti*.

Preference is also given to mixtures comprising as biopesticide II (component 2) a biopesticide from group L5) selected from *Azospirillum amazonense* SpY2, *A. brasilense* XOH, *A. brasilense* Sp245, *A. brasilense* Cd, *A. brasilense* Ab-V5, *A. brasilense* Ab-V6, *A. lipoferum* Sp31, *Bradyrhizobium* sp. (*Vigna*) PNL1, *B. elkanii* SEMIA 587, *B. elkanii* SEMIA 5019, *B. japonicum* SEMIA 5079, *B. japonicum* SEMIA 5080, *B. japonicum* TA-11, *B. japonicum* 532c, *Paenibacillus alvei* NAS6G6, *Peniciillium bilaiae* strains ATCC 18309, ATCC 20851 and ATCC 22348; *Rhizobium leguminosarum* bv. *phaseoli* RG-B10, *R. l.* bv. *viciae* P1NP3Cst, *R. l.* bv. *viciae* $R^G$-P2, *R. l.* bv. *trifolii* RP113-7, *R. l.* bv. *viciae* SU303, *R. l.* bv. *viciae* WSM1455, *R. tropici* SEMIA 4077, *R. tropici* PRF 81 and *Sinorhizobium meliloti*; even more preferably selected from *Azospirillum brasilense* Sp245, *Bradyrhizobium* sp. (*Vigna*) PNL1, B *B. elkanii* SEMIA 587, *B. elkanii* SEMIA 5019, *B. japonicum* SEMIA 5079, *B. japonicum* SEMIA 5080, *B. japonicum* TA-11 and *B. japonicum* 532c.

The present invention also relates to mixtures, wherein the at least one biopesticide II is selected from *Azospirillum amazonense, A. brasilense, A. lipoferum, A. irakense* and *A. halopraeferens*, more preferably from *A. brasilense*, in particular selected from *A. brasilense* strains Sp245 and AZ39 which are both commercially used in Brazil and are obtainable from EMBRAPA-Agrobiologia, Brazil, and strains Ab-V5 and Ab-V6; in particular mixtures of these strains Ab-V5 and Ab-V6. These mixtures are particularly suitable in soybean, especially as seed treatment.

The present invention also relates to mixtures wherein the at least one biopesticide II is selected from *A. amazonense, A. brasilense, A. lipoferum, A. irakense* and *A. halopraeferens*, more preferably *A. brasilense*, and further comprises a pesticide III, wherein pesticide III is selected from jasmonic acid, its salts and derivatives thereof, preferably methyl-jasmonate or cis-jasmone.

According to another embodiment of the inventive mixtures, *Bradyrhizobium* spp. (meaning any *Bradyrhizobium* species and/or strain) as biopesticide II is *B. japonicum*. These mixtures are particularly suitable in soybean. Certain *B. japonicum* strains have been re-classified as a novel species *B. elkanii*, e. g. strain USDA 76 (Can. J. Microbiol. 38, 501-505, 1992). *Bradyrhizobium* spp. are cultivated using media and fermentation techniques known in the art, e. g. in yeast extract-mannitol broth (YEM) at 27° C. for about 5 days.

The present invention also relates to mixtures, wherein the at least one biopesticide II is selected from *Bradyrhizobium* spp., even more preferably from *B.* sp. (*Arachis*), *B. elkanii, B. japonicum, B. liaoningense* and *B. lupini*, and further comprises a pesticide III (component 3), wherein pesticide III is selected from jasmonic acid, its salts and derivatives thereof, preferably methyl-jasmonate or cis-jasmone.

Preferably, *B. japonicum* is selected from strains E-109, SEMIA 5079, SEMIA 5080, TA-11 and 532c. According to a further embodiment, mixtures of *B. japonicum* strains TA-11 and 532c or *B. japonicum* strains SEMIA 5079 and 5080 are used. The strains having a prefix SEMIA are especially suitable for soybean grown in Australia or South America, in particular in Brazil. More preferably, mixtures of *B. japonicum* SEMIA 5079 and SEMIA 5080 are used. *B. japonicum* WB74 is especially suitable for soybean grown in South America and Africa, in particular in South Africa. Strain E-109 is especially suitable for soybean grown in South America, in particular in Argentina.

The present invention also relates to mixtures, wherein the at least one biopesticide II is selected from *B. japonicum* and further comprises a pesticide III, wherein pesticide III is selected from jasmonic acid, its salts and derivatives thereof, preferably methyl-jasmonate or cis-jasmone.

The present invention also relates to mixtures, wherein the at least one biopesticide II is selected from *Bradyrhizobium elkanii* and *Bradyrhizobium liaoningense*, more preferably from *B. elkanii* even more preferably *B. elkanii* strains SEMIA 587 and SEMIA 5019; in particular mixtures of both. These mixtures are particularly suitable in soybean in Australia or South America, in particular in Brazil.

The present invention also relates to mixtures, wherein biopesticide II is selected from *Bradyrhizobium* sp. (*Arachis*) and *B.* sp. (*Vigna*) which shall describe the cowpea miscellany cross-inoculation group which includes inter alia indigenous cowpea bradyrhizobia on cowpea (*Vigna unguiculata*), siratro (*Macroptilium atropurpureum*), lima bean (*Phaseolus lunatus*), and peanut (*Arachis hypogaea*), in particular in particular *B.* sp. (*Vigna*) strain PNL1. This mixture comprising as biopesticide II *B.* sp. (*Arachis*) or *B.* sp. (*Vigna*) is especially suitable for use in peanut, cowpea, Mung bean, Moth bean, Dune bean, Rice bean, Snake bean and Creeping *vigna*, in particular peanut.

The present invention also relates to mixtures, wherein the at least one biopesticide II is selected from *Bradyrhizobium lupini* (also called *B.* sp. (*Lupine*), *B. lupines* or

*Rhizobium lupini*). These mixtures are especially suitable for use in dry beans and lupins. Preferably, *B. lupini* is strain LL13. This strain is especially suitable for lupins grown in Australia, North America or Europe, in particular in Europe.

The present invention also relates to mixtures wherein the at least one biopesticide II is selected from *Rhizobium leguminosarum* bv. *phaseoli* especially for the legume common bean (*Phaseolus vulgaris*), but also for other for various legumes such as alfalfa, clover, peas, beans, lentils, soybeans, peanuts and other crops such as corn and lettuce, even more preferably strain RG-B10 thereof; *R. l.* bv. *trifolii*, especially strain RP113-7 thereof, *R. l.* bv. *viciae*, in particular strains RG-P2, SU303, WSM1455 and P1NP3Cst thereof, in particular P1NP3Cst; *R. tropici*, especially strains CC511, CIAT 899 and PRF 81 thereof; and *Sinorhizobium meliloti*, especially strain RCR2011 thereof. Further *R. l.* bv. *phaseoli* or *R. etli* strains are e. g. known from the above mentioned references and Appl. Environ. Microbiol. 45(3), 737-742, 1983; ibida 54(5), 1280-1283, 1988.

According to a further embodiment, in the inventive mixtures biopesticide II is selected from one compound II selected from *Sinorhizobium meliloti* more preferably from RCR2011, *S. meliloti* NRG185, *S. meliloti* RR1128, *S. meliloti* SU277,

*R. tropici* is useful for a range of legume crops especially all kind of clovers e. g. in tropical regions such as Brazil. Preferably, mixtures comprise as *R. tropici* at least one strain selected from CC511, CIAT899, H12 and PRF 81.

The present invention also relates to mixtures wherein the at least one biopesticide II is selected from *R. leguminosarum* bv. *phaseoli*, *R. l.* bv. *trifolii*, *R. l.* bv. *viciae*, *R. tropici* and *Sinorhizobium meliloti*, and further comprises a pesticide III, wherein pesticide III is selected from jasmonic acid, its salts and derivatives thereof, preferably methyljasmonate or cis-jasmone.

According to a further embodiment, the at least one biopesticide II is selected from *Delftia acidovorans*, in particular strain RAY209, especially in soybean and canola.

Particularly preferred are the following binary mixtures listed in Table A wherein compounds I are selected from compounds I-1 to I-18 and compounds II are selected from compounds and biopesticides II-1 to II-55 as defined above and listed:

TABLE A

Binary Mixtures A-1 to A-990 comprising as active ingredients one compound I as defined and numbered above as component 1) (Co. 1) and one compound II as defined and numbered above as component 2) (Co. 2).

| Mixt. | Co. 1 | Co. 2 |
|---|---|---|
| A-1 | I-1 | II-1 |
| A-2 | I-1 | II-2 |
| A-3 | I-1 | II-49 |
| A-4 | I-1 | II-3 |
| A-5 | I-1 | II-4 |
| A-6 | I-1 | II-5 |
| A-7 | I-1 | II-6 |
| A-8 | I-1 | II-7 |
| A-9 | I-1 | II-8 |
| A-10 | I-1 | II-9 |
| A-11 | I-1 | II-10 |
| A-12 | I-1 | II-11 |
| A-13 | I-1 | II-12 |
| A-14 | I-1 | II-13 |
| A-15 | I-1 | II-14 |
| A-16 | I-1 | II-15 |
| A-17 | I-1 | II-16 |
| A-18 | I-1 | II-17 |

TABLE A-continued

Binary Mixtures A-1 to A-990 comprising as active ingredients one compound I as defined and numbered above as component 1) (Co. 1) and one compound II as defined and numbered above as component 2) (Co. 2).

| Mixt. | Co. 1 | Co. 2 |
|---|---|---|
| A-19 | I-1 | II-18 |
| A-20 | I-1 | II-19 |
| A-21 | I-1 | II-20 |
| A-22 | I-1 | II-21 |
| A-23 | I-1 | II-22 |
| A-24 | I-1 | II-23 |
| A-25 | I-1 | II-24 |
| A-26 | I-1 | II-25 |
| A-27 | I-1 | II-26 |
| A-28 | I-1 | II-27 |
| A-29 | I-1 | II-28 |
| A-30 | I-1 | II-29 |
| A-31 | I-1 | II-30 |
| A-32 | I-1 | II-31 |
| A-33 | I-1 | II-32 |
| A-34 | I-1 | II-33 |
| A-35 | I-1 | II-34 |
| A-36 | I-1 | II-35 |
| A-37 | I-1 | II-36 |
| A-38 | I-1 | II-37 |
| A-39 | I-1 | II-38 |
| A-40 | I-1 | II-39 |
| A-41 | I-1 | II-40 |
| A-42 | I-1 | II-41 |
| A-43 | I-1 | II-42 |
| A-44 | I-1 | II-43 |
| A-45 | I-1 | II-44 |
| A-46 | I-1 | II-45 |
| A-47 | I-1 | II-46 |
| A-48 | I-1 | II-47 |
| A-49 | I-1 | II-48 |
| A-50 | I-1 | II-50 |
| A-51 | I-1 | II-51 |
| A-52 | I-1 | II-52 |
| A-53 | I-1 | II-53 |
| A-54 | I-1 | II-54 |
| A-55 | I-1 | II-55 |
| A-56 | I-2 | II-1 |
| A-57 | I-2 | II-2 |
| A-58 | I-2 | II-49 |
| A-59 | I-2 | II-3 |
| A-60 | I-2 | II-4 |
| A-61 | I-2 | II-5 |
| A-62 | I-2 | II-6 |
| A-63 | I-2 | II-7 |
| A-64 | I-2 | II-8 |
| A-65 | I-2 | II-9 |
| A-66 | I-2 | II-10 |
| A-67 | I-2 | II-11 |
| A-68 | I-2 | II-12 |
| A-69 | I-2 | II-13 |
| A-70 | I-2 | II-14 |
| A-71 | I-2 | II-15 |
| A-72 | I-2 | II-16 |
| A-73 | I-2 | II-17 |
| A-74 | I-2 | II-18 |
| A-75 | I-2 | II-19 |
| A-76 | I-2 | II-20 |
| A-77 | I-2 | II-21 |
| A-78 | I-2 | II-22 |
| A-79 | I-2 | II-23 |
| A-80 | I-2 | II-24 |
| A-81 | I-2 | II-25 |
| A-82 | I-2 | II-26 |
| A-83 | I-2 | II-27 |
| A-84 | I-2 | II-28 |
| A-85 | I-2 | II-29 |
| A-86 | I-2 | II-30 |
| A-87 | I-2 | II-31 |
| A-88 | I-2 | II-32 |
| A-89 | I-2 | II-33 |
| A-90 | I-2 | II-34 |
| A-91 | I-2 | II-35 |

TABLE A-continued

Binary Mixtures A-1 to A-990 comprising as active ingredients one compound I as defined and numbered above as component 1) (Co. 1) and one compound II as defined and numbered above as component 2) (Co. 2).

| Mixt. | Co. 1 | Co. 2 |
| --- | --- | --- |
| A-92 | I-2 | II-36 |
| A-93 | I-2 | II-37 |
| A-94 | I-2 | II-38 |
| A-95 | I-2 | II-39 |
| A-96 | I-2 | II-40 |
| A-97 | I-2 | II-41 |
| A-98 | I-2 | II-42 |
| A-99 | I-2 | II-43 |
| A-100 | I-2 | II-44 |
| A-101 | I-2 | II-45 |
| A-102 | I-2 | II-46 |
| A-103 | I-2 | II-47 |
| A-104 | I-2 | II-48 |
| A-105 | I-2 | II-50 |
| A-106 | I-2 | II-51 |
| A-107 | I-2 | II-52 |
| A-108 | I-2 | II-53 |
| A-109 | I-2 | II-54 |
| A-110 | I-2 | II-55 |
| A-111 | I-3 | II-1 |
| A-112 | I-3 | II-2 |
| A-113 | I-3 | II-49 |
| A-114 | I-3 | II-3 |
| A-115 | I-3 | II-4 |
| A-116 | I-3 | II-5 |
| A-117 | I-3 | II-6 |
| A-118 | I-3 | II-7 |
| A-119 | I-3 | II-8 |
| A-120 | I-3 | II-9 |
| A-121 | I-3 | II-10 |
| A-122 | I-3 | II-11 |
| A-123 | I-3 | II-12 |
| A-124 | I-3 | II-13 |
| A-125 | I-3 | II-14 |
| A-126 | I-3 | II-15 |
| A-127 | I-3 | II-16 |
| A-128 | I-3 | II-17 |
| A-129 | I-3 | II-18 |
| A-130 | I-3 | II-19 |
| A-131 | I-3 | II-20 |
| A-132 | I-3 | II-21 |
| A-133 | I-3 | II-22 |
| A-134 | I-3 | II-23 |
| A-135 | I-3 | II-24 |
| A-136 | I-3 | II-25 |
| A-137 | I-3 | II-26 |
| A-138 | I-3 | II-27 |
| A-139 | I-3 | II-28 |
| A-140 | I-3 | II-29 |
| A-141 | I-3 | II-30 |
| A-142 | I-3 | II-31 |
| A-143 | I-3 | II-32 |
| A-144 | I-3 | II-33 |
| A-145 | I-3 | II-34 |
| A-146 | I-3 | II-35 |
| A-147 | I-3 | II-36 |
| A-148 | I-3 | II-37 |
| A-149 | I-3 | II-38 |
| A-150 | I-3 | II-39 |
| A-151 | I-3 | II-40 |
| A-152 | I-3 | II-41 |
| A-153 | I-3 | II-42 |
| A-154 | I-3 | II-43 |
| A-155 | I-3 | II-44 |
| A-156 | I-3 | II-45 |
| A-157 | I-3 | II-46 |
| A-158 | I-3 | II-47 |
| A-159 | I-3 | II-48 |
| A-160 | I-3 | II-50 |
| A-161 | I-3 | II-51 |
| A-162 | I-3 | II-52 |
| A-163 | I-3 | II-53 |
| A-164 | I-3 | II-54 |
| A-165 | I-3 | II-55 |
| A-166 | I-4 | II-1 |
| A-167 | I-4 | II-2 |
| A-168 | I-4 | II-49 |
| A-169 | I-4 | II-3 |
| A-170 | I-4 | II-4 |
| A-171 | I-4 | II-5 |
| A-172 | I-4 | II-6 |
| A-173 | I-4 | II-7 |
| A-174 | I-4 | II-8 |
| A-175 | I-4 | II-9 |
| A-176 | I-4 | II-10 |
| A-177 | I-4 | II-11 |
| A-178 | I-4 | II-12 |
| A-179 | I-4 | II-13 |
| A-180 | I-4 | II-14 |
| A-181 | I-4 | II-15 |
| A-182 | I-4 | II-16 |
| A-183 | I-4 | II-17 |
| A-184 | I-4 | II-18 |
| A-185 | I-4 | II-19 |
| A-186 | I-4 | II-20 |
| A-187 | I-4 | II-21 |
| A-188 | I-4 | II-22 |
| A-189 | I-4 | II-23 |
| A-190 | I-4 | II-24 |
| A-191 | I-4 | II-25 |
| A-192 | I-4 | II-26 |
| A-193 | I-4 | II-27 |
| A-194 | I-4 | II-28 |
| A-195 | I-4 | II-29 |
| A-196 | I-4 | II-30 |
| A-197 | I-4 | II-31 |
| A-198 | I-4 | II-32 |
| A-199 | I-4 | II-33 |
| A-200 | I-4 | II-34 |
| A-201 | I-4 | II-35 |
| A-202 | I-4 | II-36 |
| A-203 | I-4 | II-37 |
| A-204 | I-4 | II-38 |
| A-205 | I-4 | II-39 |
| A-206 | I-4 | II-40 |
| A-207 | I-4 | II-41 |
| A-208 | I-4 | II-42 |
| A-209 | I-4 | II-43 |
| A-210 | I-4 | II-44 |
| A-211 | I-4 | II-45 |
| A-212 | I-4 | II-46 |
| A-213 | I-4 | II-47 |
| A-214 | I-4 | II-48 |
| A-215 | I-4 | II-50 |
| A-216 | I-4 | II-51 |
| A-217 | I-4 | II-52 |
| A-218 | I-4 | II-53 |
| A-219 | I-4 | II-54 |
| A-220 | I-4 | II-55 |
| A-221 | I-5 | II-1 |
| A-222 | I-5 | II-2 |
| A-223 | I-5 | II-49 |
| A-224 | I-5 | II-3 |
| A-225 | I-5 | II-4 |
| A-226 | I-5 | II-5 |
| A-227 | I-5 | II-6 |
| A-228 | I-5 | II-7 |
| A-229 | I-5 | II-8 |
| A-230 | I-5 | II-9 |
| A-231 | I-5 | II-10 |
| A-232 | I-5 | II-11 |
| A-233 | I-5 | II-12 |
| A-234 | I-5 | II-13 |
| A-235 | I-5 | II-14 |
| A-236 | I-5 | II-15 |
| A-237 | I-5 | II-16 |

TABLE A-continued

Binary Mixtures A-1 to A-990 comprising as active ingredients one compound I as defined and numbered above as component 1) (Co. 1) and one compound II as defined and numbered above as component 2) (Co. 2).

| Mixt. | Co. 1 | Co. 2 |
|---|---|---|
| A-238 | I-5 | II-17 |
| A-239 | I-5 | II-18 |
| A-240 | I-5 | II-19 |
| A-241 | I-5 | II-20 |
| A-242 | I-5 | II-21 |
| A-243 | I-5 | II-22 |
| A-244 | I-5 | II-23 |
| A-245 | I-5 | II-24 |
| A-246 | I-5 | II-25 |
| A-247 | I-5 | II-26 |
| A-248 | I-5 | II-27 |
| A-249 | I-5 | II-28 |
| A-250 | I-5 | II-29 |
| A-251 | I-5 | II-30 |
| A-252 | I-5 | II-31 |
| A-253 | I-5 | II-32 |
| A-254 | I-5 | II-33 |
| A-255 | I-5 | II-34 |
| A-256 | I-5 | II-35 |
| A-257 | I-5 | II-36 |
| A-258 | I-5 | II-37 |
| A-259 | I-5 | II-38 |
| A-260 | I-5 | II-39 |
| A-261 | I-5 | II-40 |
| A-262 | I-5 | II-41 |
| A-263 | I-5 | II-42 |
| A-264 | I-5 | II-43 |
| A-265 | I-5 | II-44 |
| A-266 | I-5 | II-45 |
| A-267 | I-5 | II-46 |
| A-268 | I-5 | II-47 |
| A-269 | I-5 | II-48 |
| A-270 | I-5 | II-50 |
| A-271 | I-5 | II-51 |
| A-272 | I-5 | II-52 |
| A-273 | I-5 | II-53 |
| A-274 | I-5 | II-54 |
| A-275 | I-5 | II-55 |
| A-276 | I-6 | II-1 |
| A-277 | I-6 | II-2 |
| A-278 | I-6 | II-49 |
| A-279 | I-6 | II-3 |
| A-280 | I-6 | II-4 |
| A-281 | I-6 | II-5 |
| A-282 | I-6 | II-6 |
| A-283 | I-6 | II-7 |
| A-284 | I-6 | II-8 |
| A-285 | I-6 | II-9 |
| A-286 | I-6 | II-10 |
| A-287 | I-6 | II-11 |
| A-288 | I-6 | II-12 |
| A-289 | I-6 | II-13 |
| A-290 | I-6 | II-14 |
| A-291 | I-6 | II-15 |
| A-292 | I-6 | II-16 |
| A-293 | I-6 | II-17 |
| A-294 | I-6 | II-18 |
| A-295 | I-6 | II-19 |
| A-296 | I-6 | II-20 |
| A-297 | I-6 | II-21 |
| A-298 | I-6 | II-22 |
| A-299 | I-6 | II-23 |
| A-300 | I-6 | II-24 |
| A-301 | I-6 | II-25 |
| A-302 | I-6 | II-26 |
| A-303 | I-6 | II-27 |
| A-304 | I-6 | II-28 |
| A-305 | I-6 | II-29 |
| A-306 | I-6 | II-30 |
| A-307 | I-6 | II-31 |
| A-308 | I-6 | II-32 |
| A-309 | I-6 | II-33 |
| A-310 | I-6 | II-34 |
| A-311 | I-6 | II-35 |
| A-312 | I-6 | II-36 |
| A-313 | I-6 | II-37 |
| A-314 | I-6 | II-38 |
| A-315 | I-6 | II-39 |
| A-316 | I-6 | II-40 |
| A-317 | I-6 | II-41 |
| A-318 | I-6 | II-42 |
| A-319 | I-6 | II-43 |
| A-320 | I-6 | II-44 |
| A-321 | I-6 | II-45 |
| A-322 | I-6 | II-46 |
| A-323 | I-6 | II-47 |
| A-324 | I-6 | II-48 |
| A-325 | I-6 | II-50 |
| A-326 | I-6 | II-51 |
| A-327 | I-6 | II-52 |
| A-328 | I-6 | II-53 |
| A-329 | I-6 | II-54 |
| A-330 | I-6 | II-55 |
| A-331 | I-7 | II-1 |
| A-332 | I-7 | II-2 |
| A-333 | I-7 | II-49 |
| A-334 | I-7 | II-3 |
| A-335 | I-7 | II-4 |
| A-336 | I-7 | II-5 |
| A-337 | I-7 | II-6 |
| A-338 | I-7 | II-7 |
| A-339 | I-7 | II-8 |
| A-340 | I-7 | II-9 |
| A-341 | I-7 | II-10 |
| A-342 | I-7 | II-11 |
| A-343 | I-7 | II-12 |
| A-344 | I-7 | II-13 |
| A-345 | I-7 | II-14 |
| A-346 | I-7 | II-15 |
| A-347 | I-7 | II-16 |
| A-348 | I-7 | II-17 |
| A-349 | I-7 | II-18 |
| A-350 | I-7 | II-19 |
| A-351 | I-7 | II-20 |
| A-352 | I-7 | II-21 |
| A-353 | I-7 | II-22 |
| A-354 | I-7 | II-23 |
| A-355 | I-7 | II-24 |
| A-356 | I-7 | II-25 |
| A-357 | I-7 | II-26 |
| A-358 | I-7 | II-27 |
| A-359 | I-7 | II-28 |
| A-360 | I-7 | II-29 |
| A-361 | I-7 | II-30 |
| A-362 | I-7 | II-31 |
| A-363 | I-7 | II-32 |
| A-364 | I-7 | II-33 |
| A-365 | I-7 | II-34 |
| A-366 | I-7 | II-35 |
| A-367 | I-7 | II-36 |
| A-368 | I-7 | II-37 |
| A-369 | I-7 | II-38 |
| A-370 | I-7 | II-39 |
| A-371 | I-7 | II-40 |
| A-372 | I-7 | II-41 |
| A-373 | I-7 | II-42 |
| A-374 | I-7 | II-43 |
| A-375 | I-7 | II-44 |
| A-376 | I-7 | II-45 |
| A-377 | I-7 | II-46 |
| A-378 | I-7 | II-47 |
| A-379 | I-7 | II-48 |
| A-380 | I-7 | II-50 |
| A-381 | I-7 | II-51 |
| A-382 | I-7 | II-52 |
| A-383 | I-7 | II-53 |

TABLE A-continued

Binary Mixtures A-1 to A-990 comprising as active ingredients one compound I as defined and numbered above as component 1) (Co. 1) and one compound II as defined and numbered above as component 2) (Co. 2).

| Mixt. | Co. 1 | Co. 2 |
|---|---|---|
| A-384 | I-7 | II-54 |
| A-385 | I-7 | II-55 |
| A-386 | I-8 | II-1 |
| A-387 | I-8 | II-2 |
| A-388 | I-8 | II-49 |
| A-389 | I-8 | II-3 |
| A-390 | I-8 | II-4 |
| A-391 | I-8 | II-5 |
| A-392 | I-8 | II-6 |
| A-393 | I-8 | II-7 |
| A-394 | I-8 | II-8 |
| A-395 | I-8 | II-9 |
| A-396 | I-8 | II-10 |
| A-397 | I-8 | II-11 |
| A-398 | I-8 | II-12 |
| A-399 | I-8 | II-13 |
| A-400 | I-8 | II-14 |
| A-401 | I-8 | II-15 |
| A-402 | I-8 | II-16 |
| A-403 | I-8 | II-17 |
| A-404 | I-8 | II-18 |
| A-405 | I-8 | II-19 |
| A-406 | I-8 | II-20 |
| A-407 | I-8 | II-21 |
| A-408 | I-8 | II-22 |
| A-409 | I-8 | II-23 |
| A-410 | I-8 | II-24 |
| A-411 | I-8 | II-25 |
| A-412 | I-8 | II-26 |
| A-413 | I-8 | II-27 |
| A-414 | I-8 | II-28 |
| A-415 | I-8 | II-29 |
| A-416 | I-8 | II-30 |
| A-417 | I-8 | II-31 |
| A-418 | I-8 | II-32 |
| A-419 | I-8 | II-33 |
| A-420 | I-8 | II-34 |
| A-421 | I-8 | II-35 |
| A-422 | I-8 | II-36 |
| A-423 | I-8 | II-37 |
| A-424 | I-8 | II-38 |
| A-425 | I-8 | II-39 |
| A-426 | I-8 | II-40 |
| A-427 | I-8 | II-41 |
| A-428 | I-8 | II-42 |
| A-429 | I-8 | II-43 |
| A-430 | I-8 | II-44 |
| A-431 | I-8 | II-45 |
| A-432 | I-8 | II-46 |
| A-433 | I-8 | II-47 |
| A-434 | I-8 | II-48 |
| A-435 | I-8 | II-50 |
| A-436 | I-8 | II-51 |
| A-437 | I-8 | II-52 |
| A-438 | I-8 | II-53 |
| A-439 | I-8 | II-54 |
| A-440 | I-8 | II-55 |
| A-441 | I-9 | II-1 |
| A-442 | I-9 | II-2 |
| A-443 | I-9 | II-49 |
| A-444 | I-9 | II-3 |
| A-445 | I-9 | II-4 |
| A-446 | I-9 | II-5 |
| A-447 | I-9 | II-6 |
| A-448 | I-9 | II-7 |
| A-449 | I-9 | II-8 |
| A-450 | I-9 | II-9 |
| A-451 | I-9 | II-10 |
| A-452 | I-9 | II-11 |
| A-453 | I-9 | II-12 |
| A-454 | I-9 | II-13 |
| A-455 | I-9 | II-14 |
| A-456 | I-9 | II-15 |
| A-457 | I-9 | II-16 |
| A-458 | I-9 | II-17 |
| A-459 | I-9 | II-18 |
| A-460 | I-9 | II-19 |
| A-461 | I-9 | II-20 |
| A-462 | I-9 | II-21 |
| A-463 | I-9 | II-22 |
| A-464 | I-9 | II-23 |
| A-465 | I-9 | II-24 |
| A-466 | I-9 | II-25 |
| A-467 | I-9 | II-26 |
| A-468 | I-9 | II-27 |
| A-469 | I-9 | II-28 |
| A-470 | I-9 | II-29 |
| A-471 | I-9 | II-30 |
| A-472 | I-9 | II-31 |
| A-473 | I-9 | II-32 |
| A-474 | I-9 | II-33 |
| A-475 | I-9 | II-34 |
| A-476 | I-9 | II-35 |
| A-477 | I-9 | II-36 |
| A-478 | I-9 | II-37 |
| A-479 | I-9 | II-38 |
| A-480 | I-9 | II-39 |
| A-481 | I-9 | II-40 |
| A-482 | I-9 | II-41 |
| A-483 | I-9 | II-42 |
| A-484 | I-9 | II-43 |
| A-485 | I-9 | II-44 |
| A-486 | I-9 | II-45 |
| A-487 | I-9 | II-46 |
| A-488 | I-9 | II-47 |
| A-489 | I-9 | II-48 |
| A-490 | I-9 | II-50 |
| A-491 | I-9 | II-51 |
| A-492 | I-9 | II-52 |
| A-493 | I-9 | II-53 |
| A-494 | I-9 | II-54 |
| A-495 | I-9 | II-55 |
| A-496 | I-10 | II-1 |
| A-497 | I-10 | II-2 |
| A-498 | I-10 | II-49 |
| A-499 | I-10 | II-3 |
| A-500 | I-10 | II-4 |
| A-501 | I-10 | II-5 |
| A-502 | I-10 | II-6 |
| A-503 | I-10 | II-7 |
| A-504 | I-10 | II-8 |
| A-505 | I-10 | II-9 |
| A-506 | I-10 | II-10 |
| A-507 | I-10 | II-11 |
| A-508 | I-10 | II-12 |
| A-509 | I-10 | II-13 |
| A-510 | I-10 | II-14 |
| A-511 | I-10 | II-15 |
| A-512 | I-10 | II-16 |
| A-513 | I-10 | II-17 |
| A-514 | I-10 | II-18 |
| A-515 | I-10 | II-19 |
| A-516 | I-10 | II-20 |
| A-517 | I-10 | II-21 |
| A-518 | I-10 | II-22 |
| A-519 | I-10 | II-23 |
| A-520 | I-10 | II-24 |
| A-521 | I-10 | II-25 |
| A-522 | I-10 | II-26 |
| A-523 | I-10 | II-27 |
| A-524 | I-10 | II-28 |
| A-525 | I-10 | II-29 |
| A-526 | I-10 | II-30 |
| A-527 | I-10 | II-31 |
| A-528 | I-10 | II-32 |
| A-529 | I-10 | II-33 |

TABLE A-continued

Binary Mixtures A-1 to A-990 comprising as active ingredients one compound I as defined and numbered above as component 1) (Co. 1) and one compound II as defined and numbered above as component 2) (Co. 2).

| Mixt. | Co. 1 | Co. 2 |
|---|---|---|
| A-530 | I-10 | II-34 |
| A-531 | I-10 | II-35 |
| A-532 | I-10 | II-36 |
| A-533 | I-10 | II-37 |
| A-534 | I-10 | II-38 |
| A-535 | I-10 | II-39 |
| A-536 | I-10 | II-40 |
| A-537 | I-10 | II-41 |
| A-538 | I-10 | II-42 |
| A-539 | I-10 | II-43 |
| A-540 | I-10 | II-44 |
| A-541 | I-10 | II-45 |
| A-542 | I-10 | II-46 |
| A-543 | I-10 | II-47 |
| A-544 | I-10 | II-48 |
| A-545 | I-10 | II-50 |
| A-546 | I-10 | II-51 |
| A-547 | I-10 | II-52 |
| A-548 | I-10 | II-53 |
| A-549 | I-10 | II-54 |
| A-550 | I-10 | II-55 |
| A-551 | I-11 | II-1 |
| A-552 | I-11 | II-2 |
| A-553 | I-11 | II-49 |
| A-554 | I-11 | II-3 |
| A-555 | I-11 | II-4 |
| A-556 | I-11 | II-5 |
| A-557 | I-11 | II-6 |
| A-558 | I-11 | II-7 |
| A-559 | I-11 | II-8 |
| A-560 | I-11 | II-9 |
| A-561 | I-11 | II-10 |
| A-562 | I-11 | II-11 |
| A-563 | I-11 | II-12 |
| A-564 | I-11 | II-13 |
| A-565 | I-11 | II-14 |
| A-566 | I-11 | II-15 |
| A-567 | I-11 | II-16 |
| A-568 | I-11 | II-17 |
| A-569 | I-11 | II-18 |
| A-570 | I-11 | II-19 |
| A-571 | I-11 | II-20 |
| A-572 | I-11 | II-21 |
| A-573 | I-11 | II-22 |
| A-574 | I-11 | II-23 |
| A-575 | I-11 | II-24 |
| A-576 | I-11 | II-25 |
| A-577 | I-11 | II-26 |
| A-578 | I-11 | II-27 |
| A-579 | I-11 | II-28 |
| A-580 | I-11 | II-29 |
| A-581 | I-11 | II-30 |
| A-582 | I-11 | II-31 |
| A-583 | I-11 | II-32 |
| A-584 | I-11 | II-33 |
| A-585 | I-11 | II-34 |
| A-586 | I-11 | II-35 |
| A-587 | I-11 | II-36 |
| A-588 | I-11 | II-37 |
| A-589 | I-11 | II-38 |
| A-590 | I-11 | II-39 |
| A-591 | I-11 | II-40 |
| A-592 | I-11 | II-41 |
| A-593 | I-11 | II-42 |
| A-594 | I-11 | II-43 |
| A-595 | I-11 | II-44 |
| A-596 | I-11 | II-45 |
| A-597 | I-11 | II-46 |
| A-598 | I-11 | II-47 |
| A-599 | I-11 | II-48 |
| A-600 | I-11 | II-50 |
| A-601 | I-11 | II-51 |
| A-602 | I-11 | II-52 |
| A-603 | I-11 | II-53 |
| A-604 | I-11 | II-54 |
| A-605 | I-11 | II-55 |
| A-606 | I-12 | II-1 |
| A-607 | I-12 | II-2 |
| A-608 | I-12 | II-49 |
| A-609 | I-12 | II-3 |
| A-610 | I-12 | II-4 |
| A-611 | I-12 | II-5 |
| A-612 | I-12 | II-6 |
| A-613 | I-12 | II-7 |
| A-614 | I-12 | II-8 |
| A-615 | I-12 | II-9 |
| A-616 | I-12 | II-10 |
| A-617 | I-12 | II-11 |
| A-618 | I-12 | II-12 |
| A-619 | I-12 | II-13 |
| A-620 | I-12 | II-14 |
| A-621 | I-12 | II-15 |
| A-622 | I-12 | II-16 |
| A-623 | I-12 | II-17 |
| A-624 | I-12 | II-18 |
| A-625 | I-12 | II-19 |
| A-626 | I-12 | II-20 |
| A-627 | I-12 | II-21 |
| A-628 | I-12 | II-22 |
| A-629 | I-12 | II-23 |
| A-630 | I-12 | II-24 |
| A-631 | I-12 | II-25 |
| A-632 | I-12 | II-26 |
| A-633 | I-12 | II-27 |
| A-634 | I-12 | II-28 |
| A-635 | I-12 | II-29 |
| A-636 | I-12 | II-30 |
| A-637 | I-12 | II-31 |
| A-638 | I-12 | II-32 |
| A-639 | I-12 | II-33 |
| A-640 | I-12 | II-34 |
| A-641 | I-12 | II-35 |
| A-642 | I-12 | II-36 |
| A-643 | I-12 | II-37 |
| A-644 | I-12 | II-38 |
| A-645 | I-12 | II-39 |
| A-646 | I-12 | II-40 |
| A-647 | I-12 | II-41 |
| A-648 | I-12 | II-42 |
| A-649 | I-12 | II-43 |
| A-650 | I-12 | II-44 |
| A-651 | I-12 | II-45 |
| A-652 | I-12 | II-46 |
| A-653 | I-12 | II-47 |
| A-654 | I-12 | II-48 |
| A-655 | I-12 | II-50 |
| A-656 | I-12 | II-51 |
| A-657 | I-12 | II-52 |
| A-658 | I-12 | II-53 |
| A-659 | I-12 | II-54 |
| A-660 | I-12 | II-55 |
| A-661 | I-13 | II-1 |
| A-662 | I-13 | II-2 |
| A-663 | I-13 | II-49 |
| A-664 | I-13 | II-3 |
| A-665 | I-13 | II-4 |
| A-666 | I-13 | II-5 |
| A-667 | I-13 | II-6 |
| A-668 | I-13 | II-7 |
| A-669 | I-13 | II-8 |
| A-670 | I-13 | II-9 |
| A-671 | I-13 | II-10 |
| A-672 | I-13 | II-11 |
| A-673 | I-13 | II-12 |
| A-674 | I-13 | II-13 |
| A-675 | I-13 | II-14 |

TABLE A-continued

Binary Mixtures A-1 to A-990 comprising as active ingredients one compound I as defined and numbered above as component 1) (Co. 1) and one compound II as defined and numbered above as component 2) (Co. 2).

| Mixt. | Co. 1 | Co. 2 |
|---|---|---|
| A-676 | I-13 | II-15 |
| A-677 | I-13 | II-16 |
| A-678 | I-13 | II-17 |
| A-679 | I-13 | II-18 |
| A-680 | I-13 | II-19 |
| A-681 | I-13 | II-20 |
| A-682 | I-13 | II-21 |
| A-683 | I-13 | II-22 |
| A-684 | I-13 | II-23 |
| A-685 | I-13 | II-24 |
| A-686 | I-13 | II-25 |
| A-687 | I-13 | II-26 |
| A-688 | I-13 | II-27 |
| A-689 | I-13 | II-28 |
| A-690 | I-13 | II-29 |
| A-691 | I-13 | II-30 |
| A-692 | I-13 | II-31 |
| A-693 | I-13 | II-32 |
| A-694 | I-13 | II-33 |
| A-695 | I-13 | II-34 |
| A-696 | I-13 | II-35 |
| A-697 | I-13 | II-36 |
| A-698 | I-13 | II-37 |
| A-699 | I-13 | II-38 |
| A-700 | I-13 | II-39 |
| A-701 | I-13 | II-40 |
| A-702 | I-13 | II-41 |
| A-703 | I-13 | II-42 |
| A-704 | I-13 | II-43 |
| A-705 | I-13 | II-44 |
| A-706 | I-13 | II-45 |
| A-707 | I-13 | II-46 |
| A-708 | I-13 | II-47 |
| A-709 | I-13 | II-48 |
| A-710 | I-13 | II-50 |
| A-711 | I-13 | II-51 |
| A-712 | I-13 | II-52 |
| A-713 | I-13 | II-53 |
| A-714 | I-13 | II-54 |
| A-715 | I-13 | II-55 |
| A-716 | I-14 | II-1 |
| A-717 | I-14 | II-2 |
| A-718 | I-14 | II-49 |
| A-719 | I-14 | II-3 |
| A-720 | I-14 | II-4 |
| A-721 | I-14 | II-5 |
| A-722 | I-14 | II-6 |
| A-723 | I-14 | II-7 |
| A-724 | I-14 | II-8 |
| A-725 | I-14 | II-9 |
| A-726 | I-14 | II-10 |
| A-727 | I-14 | II-11 |
| A-728 | I-14 | II-12 |
| A-729 | I-14 | II-13 |
| A-730 | I-14 | II-14 |
| A-731 | I-14 | II-15 |
| A-732 | I-14 | II-16 |
| A-733 | I-14 | II-17 |
| A-734 | I-14 | II-18 |
| A-735 | I-14 | II-19 |
| A-736 | I-14 | II-20 |
| A-737 | I-14 | II-21 |
| A-738 | I-14 | II-22 |
| A-739 | I-14 | II-23 |
| A-740 | I-14 | II-24 |
| A-741 | I-14 | II-25 |
| A-742 | I-14 | II-26 |
| A-743 | I-14 | II-27 |
| A-744 | I-14 | II-28 |
| A-745 | I-14 | II-29 |
| A-746 | I-14 | II-30 |
| A-747 | I-14 | II-31 |
| A-748 | I-14 | II-32 |
| A-749 | I-14 | II-33 |
| A-750 | I-14 | II-34 |
| A-751 | I-14 | II-35 |
| A-752 | I-14 | II-36 |
| A-753 | I-14 | II-37 |
| A-754 | I-14 | II-38 |
| A-755 | I-14 | II-39 |
| A-756 | I-14 | II-40 |
| A-757 | I-14 | II-41 |
| A-758 | I-14 | II-42 |
| A-759 | I-14 | II-43 |
| A-760 | I-14 | II-44 |
| A-761 | I-14 | II-45 |
| A-762 | I-14 | II-46 |
| A-763 | I-14 | II-47 |
| A-764 | I-14 | II-48 |
| A-765 | I-14 | II-50 |
| A-766 | I-14 | II-51 |
| A-767 | I-14 | II-52 |
| A-768 | I-14 | II-53 |
| A-769 | I-14 | II-54 |
| A-770 | I-14 | II-55 |
| A-771 | I-15 | II-1 |
| A-772 | I-15 | II-2 |
| A-773 | I-15 | II-49 |
| A-774 | I-15 | II-3 |
| A-775 | I-15 | II-4 |
| A-776 | I-15 | II-5 |
| A-777 | I-15 | II-6 |
| A-778 | I-15 | II-7 |
| A-779 | I-15 | II-8 |
| A-780 | I-15 | II-9 |
| A-781 | I-15 | II-10 |
| A-782 | I-15 | II-11 |
| A-783 | I-15 | II-12 |
| A-784 | I-15 | II-13 |
| A-785 | I-15 | II-14 |
| A-786 | I-15 | II-15 |
| A-787 | I-15 | II-16 |
| A-788 | I-15 | II-17 |
| A-789 | I-15 | II-18 |
| A-790 | I-15 | II-19 |
| A-791 | I-15 | II-20 |
| A-792 | I-15 | II-21 |
| A-793 | I-15 | II-22 |
| A-794 | I-15 | II-23 |
| A-795 | I-15 | II-24 |
| A-796 | I-15 | II-25 |
| A-797 | I-15 | II-26 |
| A-798 | I-15 | II-27 |
| A-799 | I-15 | II-28 |
| A-800 | I-15 | II-29 |
| A-801 | I-15 | II-30 |
| A-802 | I-15 | II-31 |
| A-803 | I-15 | II-32 |
| A-804 | I-15 | II-33 |
| A-805 | I-15 | II-34 |
| A-806 | I-15 | II-35 |
| A-807 | I-15 | II-36 |
| A-808 | I-15 | II-37 |
| A-809 | I-15 | II-38 |
| A-810 | I-15 | II-39 |
| A-811 | I-15 | II-40 |
| A-812 | I-15 | II-41 |
| A-813 | I-15 | II-42 |
| A-814 | I-15 | II-43 |
| A-815 | I-15 | II-44 |
| A-816 | I-15 | II-45 |
| A-817 | I-15 | II-46 |
| A-818 | I-15 | II-47 |
| A-819 | I-15 | II-48 |
| A-820 | I-15 | II-50 |
| A-821 | I-15 | II-51 |

TABLE A-continued

Binary Mixtures A-1 to A-990 comprising as active ingredients one compound I as defined and numbered above as component 1) (Co. 1) and one compound II as defined and numbered above as component 2) (Co. 2).

| Mixt. | Co. 1 | Co. 2 |
|---|---|---|
| A-822 | I-15 | II-52 |
| A-823 | I-15 | II-53 |
| A-824 | I-15 | II-54 |
| A-825 | I-15 | II-55 |
| A-826 | I-16 | II-1 |
| A-827 | I-16 | II-2 |
| A-828 | I-16 | II-49 |
| A-829 | I-16 | II-3 |
| A-830 | I-16 | II-4 |
| A-831 | I-16 | II-5 |
| A-832 | I-16 | II-6 |
| A-833 | I-16 | II-7 |
| A-834 | I-16 | II-8 |
| A-835 | I-16 | II-9 |
| A-836 | I-16 | II-10 |
| A-837 | I-16 | II-11 |
| A-838 | I-16 | II-12 |
| A-839 | I-16 | II-13 |
| A-840 | I-16 | II-14 |
| A-841 | I-16 | II-15 |
| A-842 | I-16 | II-16 |
| A-843 | I-16 | II-17 |
| A-844 | I-16 | II-18 |
| A-845 | I-16 | II-19 |
| A-846 | I-16 | II-20 |
| A-847 | I-16 | II-21 |
| A-848 | I-16 | II-22 |
| A-849 | I-16 | II-23 |
| A-850 | I-16 | II-24 |
| A-851 | I-16 | II-25 |
| A-852 | I-16 | II-26 |
| A-853 | I-16 | II-27 |
| A-854 | I-16 | II-28 |
| A-855 | I-16 | II-29 |
| A-856 | I-16 | II-30 |
| A-857 | I-16 | II-31 |
| A-858 | I-16 | II-32 |
| A-859 | I-16 | II-33 |
| A-860 | I-16 | II-34 |
| A-861 | I-16 | II-35 |
| A-862 | I-16 | II-36 |
| A-863 | I-16 | II-37 |
| A-864 | I-16 | II-38 |
| A-865 | I-16 | II-39 |
| A-866 | I-16 | II-40 |
| A-867 | I-16 | II-41 |
| A-868 | I-16 | II-42 |
| A-869 | I-16 | II-43 |
| A-870 | I-16 | II-44 |
| A-871 | I-16 | II-45 |
| A-872 | I-16 | II-46 |
| A-873 | I-16 | II-47 |
| A-874 | I-16 | II-48 |
| A-875 | I-16 | II-50 |
| A-876 | I-16 | II-51 |
| A-877 | I-16 | II-52 |
| A-878 | I-16 | II-53 |
| A-879 | I-16 | II-54 |
| A-880 | I-16 | II-55 |
| A-881 | I-17 | II-1 |
| A-882 | I-17 | II-2 |
| A-883 | I-17 | II-49 |
| A-884 | I-17 | II-3 |
| A-885 | I-17 | II-4 |
| A-886 | I-17 | II-5 |
| A-887 | I-17 | II-6 |
| A-888 | I-17 | II-7 |
| A-889 | I-17 | II-8 |
| A-890 | I-17 | II-9 |
| A-891 | I-17 | II-10 |
| A-892 | I-17 | II-11 |
| A-893 | I-17 | II-12 |
| A-894 | I-17 | II-13 |
| A-895 | I-17 | II-14 |
| A-896 | I-17 | II-15 |
| A-897 | I-17 | II-16 |
| A-898 | I-17 | II-17 |
| A-899 | I-17 | II-18 |
| A-900 | I-17 | II-19 |
| A-901 | I-17 | II-20 |
| A-902 | I-17 | II-21 |
| A-903 | I-17 | II-22 |
| A-904 | I-17 | II-23 |
| A-905 | I-17 | II-24 |
| A-906 | I-17 | II-25 |
| A-907 | I-17 | II-26 |
| A-908 | I-17 | II-27 |
| A-909 | I-17 | II-28 |
| A-910 | I-17 | II-29 |
| A-911 | I-17 | II-30 |
| A-912 | I-17 | II-31 |
| A-913 | I-17 | II-32 |
| A-914 | I-17 | II-33 |
| A-915 | I-17 | II-34 |
| A-916 | I-17 | II-35 |
| A-917 | I-17 | II-36 |
| A-918 | I-17 | II-37 |
| A-919 | I-17 | II-38 |
| A-920 | I-17 | II-39 |
| A-921 | I-17 | II-40 |
| A-922 | I-17 | II-41 |
| A-923 | I-17 | II-42 |
| A-924 | I-17 | II-43 |
| A-925 | I-17 | II-44 |
| A-926 | I-17 | II-45 |
| A-927 | I-17 | II-46 |
| A-928 | I-17 | II-47 |
| A-929 | I-17 | II-48 |
| A-930 | I-17 | II-50 |
| A-931 | I-17 | II-51 |
| A-932 | I-17 | II-52 |
| A-933 | I-17 | II-53 |
| A-934 | I-17 | II-54 |
| A-935 | I-17 | II-55 |
| A-936 | I-18 | II-1 |
| A-937 | I-18 | II-2 |
| A-938 | I-18 | II-49 |
| A-939 | I-18 | II-3 |
| A-940 | I-18 | II-4 |
| A-941 | I-18 | II-5 |
| A-942 | I-18 | II-6 |
| A-943 | I-18 | II-7 |
| A-944 | I-18 | II-8 |
| A-945 | I-18 | II-9 |
| A-946 | I-18 | II-10 |
| A-947 | I-18 | II-11 |
| A-948 | I-18 | II-12 |
| A-949 | I-18 | II-13 |
| A-950 | I-18 | II-14 |
| A-951 | I-18 | II-15 |
| A-952 | I-18 | II-16 |
| A-953 | I-18 | II-17 |
| A-954 | I-18 | II-18 |
| A-955 | I-18 | II-19 |
| A-956 | I-18 | II-20 |
| A-957 | I-18 | II-21 |
| A-958 | I-18 | II-22 |
| A-959 | I-18 | II-23 |
| A-960 | I-18 | II-24 |
| A-961 | I-18 | II-25 |
| A-962 | I-18 | II-26 |
| A-963 | I-18 | II-27 |
| A-964 | I-18 | II-28 |
| A-965 | I-18 | II-29 |
| A-966 | I-18 | II-30 |
| A-967 | I-18 | II-31 |

TABLE A-continued

Binary Mixtures A-1 to A-990 comprising as active ingredients one compound I as defined and numbered above as component 1) (Co. 1) and one compound II as defined and numbered above as component 2) (Co. 2).

| Mixt. | Co. 1 | Co. 2 |
|---|---|---|
| A-968 | I-18 | II-32 |
| A-969 | I-18 | II-33 |
| A-970 | I-18 | II-34 |
| A-971 | I-18 | II-35 |
| A-972 | I-18 | II-36 |
| A-973 | I-18 | II-37 |
| A-974 | I-18 | II-38 |
| A-975 | I-18 | II-39 |
| A-976 | I-18 | II-40 |
| A-977 | I-18 | II-41 |
| A-978 | I-18 | II-42 |
| A-979 | I-18 | II-43 |
| A-980 | I-18 | II-44 |
| A-981 | I-18 | II-45 |
| A-982 | I-18 | II-46 |
| A-983 | I-18 | II-47 |
| A-984 | I-18 | II-48 |
| A-985 | I-18 | II-50 |
| A-986 | I-18 | II-51 |
| A-987 | I-18 | II-52 |
| A-988 | I-18 | II-53 |
| A-989 | I-18 | II-54 |
| A-990 | I-18 | II-55 |

Also particularly preferred are the following binary mixtures listed in Table A1 wherein compounds I are selected from compounds I-1 to I-18 and compounds II are selected from compounds II-56 to II-77 as defined above and listed:

TABLE A1

Binary Mixtures A1-1 to A1-396 comprising as active ingredients one compound I as defined and numbered above as component 1) (Co. 1) and one compound II as defined and numbered above as component 2) (Co. 2).

| Mixt. | Co. 1 | Co. 2 |
|---|---|---|
| A1-1 | I-1 | II-56 |
| A1-2 | I-1 | II-57 |
| A1-3 | I-1 | II-58 |
| A1-4 | I-1 | II-59 |
| A1-5 | I-1 | II-60 |
| A1-6 | I-1 | II-61 |
| A1-7 | I-1 | II-62 |
| A1-8 | I-1 | II-63 |
| A1-9 | I-1 | II-64 |
| A1-10 | I-1 | II-65 |
| A1-11 | I-1 | II-66 |
| A1-12 | I-1 | II-67 |
| A1-13 | I-1 | II-68 |
| A1-14 | I-1 | II-69 |
| A1-15 | I-1 | II-70 |
| A1-16 | I-1 | II-71 |
| A1-17 | I-1 | II-72 |
| A1-18 | I-1 | II-73 |
| A1-19 | I-1 | II-74 |
| A1-20 | I-1 | II-75 |
| A1-21 | I-1 | II-76 |
| A1-22 | I-1 | II-77 |
| A1-23 | I-2 | II-56 |
| A1-24 | I-2 | II-57 |
| A1-25 | I-2 | II-58 |
| A1-26 | I-2 | II-59 |
| A1-27 | I-2 | II-60 |
| A1-28 | I-2 | II-61 |
| A1-29 | I-2 | II-62 |
| A1-30 | I-2 | II-63 |
| A1-31 | I-2 | II-64 |
| A1-32 | I-2 | II-65 |
| A1-33 | I-2 | II-66 |
| A1-34 | I-2 | II-67 |

TABLE A1-continued

Binary Mixtures A1-1 to A1-396 comprising as active ingredients one compound I as defined and numbered above as component 1) (Co. 1) and one compound II as defined and numbered above as component 2) (Co. 2).

| Mixt. | Co. 1 | Co. 2 |
|---|---|---|
| A1-35 | I-2 | II-68 |
| A1-36 | I-2 | II-69 |
| A1-37 | I-2 | II-70 |
| A1-38 | I-2 | II-71 |
| A1-39 | I-2 | II-72 |
| A1-40 | I-2 | II-73 |
| A1-41 | I-2 | II-74 |
| A1-42 | I-2 | II-75 |
| A1-43 | I-2 | II-76 |
| A1-44 | I-2 | II-77 |
| A1-45 | I-3 | II-56 |
| A1-46 | I-3 | II-57 |
| A1-47 | I-3 | II-58 |
| A1-48 | I-3 | II-59 |
| A1-49 | I-3 | II-60 |
| A1-50 | I-3 | II-61 |
| A1-51 | I-3 | II-62 |
| A1-52 | I-3 | II-63 |
| A1-53 | I-3 | II-64 |
| A1-54 | I-3 | II-65 |
| A1-55 | I-3 | II-66 |
| A1-56 | I-3 | II-67 |
| A1-57 | I-3 | II-68 |
| A1-58 | I-3 | II-69 |
| A1-59 | I-3 | II-70 |
| A1-60 | I-3 | II-71 |
| A1-61 | I-3 | II-72 |
| A1-62 | I-3 | II-73 |
| A1-63 | I-3 | II-74 |
| A1-64 | I-3 | II-75 |
| A1-65 | I-3 | II-76 |
| A1-66 | I-3 | II-77 |
| A1-67 | I-4 | II-56 |
| A1-68 | I-4 | II-57 |
| A1-69 | I-4 | II-58 |
| A1-70 | I-4 | II-59 |
| A1-71 | I-4 | II-60 |
| A1-72 | I-4 | II-61 |
| A1-73 | I-4 | II-62 |
| A1-74 | I-4 | II-63 |
| A1-75 | I-4 | II-64 |
| A1-76 | I-4 | II-65 |
| A1-77 | I-4 | II-66 |
| A1-78 | I-4 | II-67 |
| A1-79 | I-4 | II-68 |
| A1-80 | I-4 | II-69 |
| A1-81 | I-4 | II-70 |
| A1-82 | I-4 | II-71 |
| A1-83 | I-4 | II-72 |
| A1-84 | I-4 | II-73 |
| A1-85 | I-4 | II-74 |
| A1-86 | I-4 | II-75 |
| A1-87 | I-4 | II-76 |
| A1-88 | I-4 | II-77 |
| A1-89 | I-5 | II-56 |
| A1-90 | I-5 | II-57 |
| A1-91 | I-5 | II-58 |
| A1-92 | I-5 | II-59 |
| A1-93 | I-5 | II-60 |
| A1-94 | I-5 | II-61 |
| A1-95 | I-5 | II-62 |
| A1-96 | I-5 | II-63 |
| A1-97 | I-5 | II-64 |
| A1-98 | I-5 | II-65 |
| A1-99 | I-5 | II-66 |
| A1-100 | I-5 | II-67 |
| A1-101 | I-5 | II-68 |
| A1-102 | I-5 | II-69 |
| A1-103 | I-5 | II-70 |
| A1-104 | I-5 | II-71 |
| A1-105 | I-5 | II-72 |
| A1-106 | I-5 | II-73 |
| A1-107 | I-5 | II-74 |
| A1-108 | I-5 | II-75 |

TABLE A1-continued

Binary Mixtures A1-1 to A1-396 comprising as active ingredients one compound I as defined and numbered above as component 1) (Co. 1) and one compound II as defined and numbered above as component 2) (Co. 2).

| Mixt. | Co. 1 | Co. 2 |
|---|---|---|
| A1-109 | I-5 | II-76 |
| A1-110 | I-5 | II-77 |
| A1-111 | I-6 | II-56 |
| A1-112 | I-6 | II-57 |
| A1-113 | I-6 | II-58 |
| A1-114 | I-6 | II-59 |
| A1-115 | I-6 | II-60 |
| A1-116 | I-6 | II-61 |
| A1-117 | I-6 | II-62 |
| A1-118 | I-6 | II-63 |
| A1-119 | I-6 | II-64 |
| A1-120 | I-6 | II-65 |
| A1-121 | I-6 | II-66 |
| A1-122 | I-6 | II-67 |
| A1-123 | I-6 | II-68 |
| A1-124 | I-6 | II-69 |
| A1-125 | I-6 | II-70 |
| A1-126 | I-6 | II-71 |
| A1-127 | I-6 | II-72 |
| A1-128 | I-6 | II-73 |
| A1-129 | I-6 | II-74 |
| A1-130 | I-6 | II-75 |
| A1-131 | I-6 | II-76 |
| A1-132 | I-6 | II-77 |
| A1-133 | I-7 | II-56 |
| A1-134 | I-7 | II-57 |
| A1-135 | I-7 | II-58 |
| A1-136 | I-7 | II-59 |
| A1-137 | I-7 | II-60 |
| A1-138 | I-7 | II-61 |
| A1-139 | I-7 | II-62 |
| A1-140 | I-7 | II-63 |
| A1-141 | I-7 | II-64 |
| A1-142 | I-7 | II-65 |
| A1-143 | I-7 | II-66 |
| A1-144 | I-7 | II-67 |
| A1-145 | I-7 | II-68 |
| A1-146 | I-7 | II-69 |
| A1-147 | I-7 | II-70 |
| A1-148 | I-7 | II-71 |
| A1-149 | I-7 | II-72 |
| A1-150 | I-7 | II-73 |
| A1-151 | I-7 | II-74 |
| A1-152 | I-7 | II-75 |
| A1-153 | I-7 | II-76 |
| A1-154 | I-7 | II-77 |
| A1-155 | I-8 | II-56 |
| A1-156 | I-8 | II-57 |
| A1-157 | I-8 | II-58 |
| A1-158 | I-8 | II-59 |
| A1-159 | I-8 | II-60 |
| A1-160 | I-8 | II-61 |
| A1-161 | I-8 | II-62 |
| A1-162 | I-8 | II-63 |
| A1-163 | I-8 | II-64 |
| A1-164 | I-8 | II-65 |
| A1-165 | I-8 | II-66 |
| A1-166 | I-8 | II-67 |
| A1-167 | I-8 | II-68 |
| A1-168 | I-8 | II-69 |
| A1-169 | I-8 | II-70 |
| A1-170 | I-8 | II-71 |
| A1-171 | I-8 | II-72 |
| A1-172 | I-8 | II-73 |
| A1-173 | I-8 | II-74 |
| A1-174 | I-8 | II-75 |
| A1-175 | I-8 | II-76 |
| A1-176 | I-8 | II-77 |
| A1-177 | I-9 | II-56 |
| A1-178 | I-9 | II-57 |
| A1-179 | I-9 | II-58 |
| A1-180 | I-9 | II-59 |
| A1-181 | I-9 | II-60 |
| A1-182 | I-9 | II-61 |
| A1-183 | I-9 | II-62 |
| A1-184 | I-9 | II-63 |
| A1-185 | I-9 | II-64 |
| A1-186 | I-9 | II-65 |
| A1-187 | I-9 | II-66 |
| A1-188 | I-9 | II-67 |
| A1-189 | I-9 | II-68 |
| A1-190 | I-9 | II-69 |
| A1-191 | I-9 | II-70 |
| A1-192 | I-9 | II-71 |
| A1-193 | I-9 | II-72 |
| A1-194 | I-9 | II-73 |
| A1-195 | I-9 | II-74 |
| A1-196 | I-9 | II-75 |
| A1-197 | I-9 | II-76 |
| A1-198 | I-9 | II-77 |
| A1-199 | I-10 | II-56 |
| A1-200 | I-10 | II-57 |
| A1-201 | I-10 | II-58 |
| A1-202 | I-10 | II-59 |
| A1-203 | I-10 | II-60 |
| A1-204 | I-10 | II-61 |
| A1-205 | I-10 | II-62 |
| A1-206 | I-10 | II-63 |
| A1-207 | I-10 | II-64 |
| A1-208 | I-10 | II-65 |
| A1-209 | I-10 | II-66 |
| A1-210 | I-10 | II-67 |
| A1-211 | I-10 | II-68 |
| A1-212 | I-10 | II-69 |
| A1-213 | I-10 | II-70 |
| A1-214 | I-10 | II-71 |
| A1-215 | I-10 | II-72 |
| A1-216 | I-10 | II-73 |
| A1-217 | I-10 | II-74 |
| A1-218 | I-10 | II-75 |
| A1-219 | I-10 | II-76 |
| A1-220 | I-10 | II-77 |
| A1-221 | I-11 | II-56 |
| A1-222 | I-11 | II-57 |
| A1-223 | I-11 | II-58 |
| A1-224 | I-11 | II-59 |
| A1-225 | I-11 | II-60 |
| A1-226 | I-11 | II-61 |
| A1-227 | I-11 | II-62 |
| A1-228 | I-11 | II-63 |
| A1-229 | I-11 | II-64 |
| A1-230 | I-11 | II-65 |
| A1-231 | I-11 | II-66 |
| A1-232 | I-11 | II-67 |
| A1-233 | I-11 | II-68 |
| A1-234 | I-11 | II-69 |
| A1-235 | I-11 | II-70 |
| A1-236 | I-11 | II-71 |
| A1-237 | I-11 | II-72 |
| A1-238 | I-11 | II-73 |
| A1-239 | I-11 | II-74 |
| A1-240 | I-11 | II-75 |
| A1-241 | I-11 | II-76 |
| A1-242 | I-11 | II-77 |
| A1-243 | I-12 | II-56 |
| A1-244 | I-12 | II-57 |
| A1-245 | I-12 | II-58 |
| A1-246 | I-12 | II-59 |
| A1-247 | I-12 | II-60 |
| A1-248 | I-12 | II-61 |
| A1-249 | I-12 | II-62 |
| A1-250 | I-12 | II-63 |
| A1-251 | I-12 | II-64 |
| A1-252 | I-12 | II-65 |
| A1-253 | I-12 | II-66 |
| A1-254 | I-12 | II-67 |
| A1-255 | I-12 | II-68 |
| A1-256 | I-12 | II-69 |

TABLE A1-continued

Binary Mixtures A1-1 to A1-396 comprising as active ingredients one compound I as defined and numbered above as component 1) (Co. 1) and one compound II as defined and numbered above as component 2) (Co. 2).

| Mixt. | Co. 1 | Co. 2 |
|---|---|---|
| A1-257 | I-12 | II-70 |
| A1-258 | I-12 | II-71 |
| A1-259 | I-12 | II-72 |
| A1-260 | I-12 | II-73 |
| A1-261 | I-12 | II-74 |
| A1-262 | I-12 | II-75 |
| A1-263 | I-12 | II-76 |
| A1-264 | I-12 | II-77 |
| A1-265 | I-13 | II-56 |
| A1-266 | I-13 | II-57 |
| A1-267 | I-13 | II-58 |
| A1-268 | I-13 | II-59 |
| A1-269 | I-13 | II-60 |
| A1-270 | I-13 | II-61 |
| A1-271 | I-13 | II-62 |
| A1-272 | I-13 | II-63 |
| A1-273 | I-13 | II-64 |
| A1-274 | I-13 | II-65 |
| A1-275 | I-13 | II-66 |
| A1-276 | I-13 | II-67 |
| A1-277 | I-13 | II-68 |
| A1-278 | I-13 | II-69 |
| A1-279 | I-13 | II-70 |
| A1-280 | I-13 | II-71 |
| A1-281 | I-13 | II-72 |
| A1-282 | I-13 | II-73 |
| A1-283 | I-13 | II-74 |
| A1-284 | I-13 | II-75 |
| A1-285 | I-13 | II-76 |
| A1-286 | I-13 | II-77 |
| A1-287 | I-14 | II-56 |
| A1-288 | I-14 | II-57 |
| A1-289 | I-14 | II-58 |
| A1-290 | I-14 | II-59 |
| A1-291 | I-14 | II-60 |
| A1-292 | I-14 | II-61 |
| A1-293 | I-14 | II-62 |
| A1-294 | I-14 | II-63 |
| A1-295 | I-14 | II-64 |
| A1-296 | I-14 | II-65 |
| A1-297 | I-14 | II-66 |
| A1-298 | I-14 | II-67 |
| A1-299 | I-14 | II-68 |
| A1-300 | I-14 | II-69 |
| A1-301 | I-14 | II-70 |
| A1-302 | I-14 | II-71 |
| A1-303 | I-14 | II-72 |
| A1-304 | I-14 | II-73 |
| A1-305 | I-14 | II-74 |
| A1-306 | I-14 | II-75 |
| A1-307 | I-14 | II-76 |
| A1-308 | I-14 | II-77 |
| A1-309 | I-15 | II-56 |
| A1-310 | I-15 | II-57 |
| A1-311 | I-15 | II-58 |
| A1-312 | I-15 | II-59 |
| A1-313 | I-15 | II-60 |
| A1-314 | I-15 | II-61 |
| A1-315 | I-15 | II-62 |
| A1-316 | I-15 | II-63 |
| A1-317 | I-15 | II-64 |
| A1-318 | I-15 | II-65 |
| A1-319 | I-15 | II-66 |
| A1-320 | I-15 | II-67 |
| A1-321 | I-15 | II-68 |
| A1-322 | I-15 | II-69 |
| A1-323 | I-15 | II-70 |
| A1-324 | I-15 | II-71 |
| A1-325 | I-15 | II-72 |
| A1-326 | I-15 | II-73 |
| A1-327 | I-15 | II-74 |
| A1-328 | I-15 | II-75 |
| A1-329 | I-15 | II-76 |
| A1-330 | I-15 | II-77 |
| A1-331 | I-16 | II-56 |
| A1-332 | I-16 | II-57 |
| A1-333 | I-16 | II-58 |
| A1-334 | I-16 | II-59 |
| A1-335 | I-16 | II-60 |
| A1-336 | I-16 | II-61 |
| A1-337 | I-16 | II-62 |
| A1-338 | I-16 | II-63 |
| A1-339 | I-16 | II-64 |
| A1-340 | I-16 | II-65 |
| A1-341 | I-16 | II-66 |
| A1-342 | I-16 | II-67 |
| A1-343 | I-16 | II-68 |
| A1-344 | I-16 | II-69 |
| A1-345 | I-16 | II-70 |
| A1-346 | I-16 | II-71 |
| A1-347 | I-16 | II-72 |
| A1-348 | I-16 | II-73 |
| A1-349 | I-16 | II-74 |
| A1-350 | I-16 | II-75 |
| A1-351 | I-16 | II-76 |
| A1-352 | I-16 | II-77 |
| A1-353 | I-17 | II-56 |
| A1-354 | I-17 | II-57 |
| A1-355 | I-17 | II-58 |
| A1-356 | I-17 | II-59 |
| A1-357 | I-17 | II-60 |
| A1-358 | I-17 | II-61 |
| A1-359 | I-17 | II-62 |
| A1-360 | I-17 | II-63 |
| A1-361 | I-17 | II-64 |
| A1-362 | I-17 | II-65 |
| A1-363 | I-17 | II-66 |
| A1-364 | I-17 | II-67 |
| A1-365 | I-17 | II-68 |
| A1-366 | I-17 | II-69 |
| A1-367 | I-17 | II-70 |
| A1-368 | I-17 | II-71 |
| A1-369 | I-17 | II-72 |
| A1-370 | I-17 | II-73 |
| A1-371 | I-17 | II-74 |
| A1-372 | I-17 | II-75 |
| A1-373 | I-17 | II-76 |
| A1-374 | I-17 | II-77 |
| A1-375 | I-18 | II-56 |
| A1-376 | I-18 | II-57 |
| A1-377 | I-18 | II-58 |
| A1-378 | I-18 | II-59 |
| A1-379 | I-18 | II-60 |
| A1-380 | I-18 | II-61 |
| A1-381 | I-18 | II-62 |
| A1-382 | I-18 | II-63 |
| A1-383 | I-18 | II-64 |
| A1-384 | I-18 | II-65 |
| A1-385 | I-18 | II-66 |
| A1-386 | I-18 | II-67 |
| A1-387 | I-18 | II-68 |
| A1-388 | I-18 | II-69 |
| A1-389 | I-18 | II-70 |
| A1-390 | I-18 | II-71 |
| A1-391 | I-18 | II-72 |
| A1-392 | I-18 | II-73 |
| A1-393 | I-18 | II-74 |
| A1-394 | I-18 | II-75 |
| A1-395 | I-18 | II-76 |
| A1-396 | I-18 | II-77 |

The mixtures and compositions thereof according to the invention can, in the use form as fungicides, also be present together with other active substances, e. g. with herbicides, insecticides, growth regulators, fungicides or else with fertilizers, as pre-mix or, if appropriate, not until immediately prior to use (tank mix).

Mixing the compounds I and compounds II and the compositions comprising them, respectively, in the use form as fungicides with other fungicides results in many cases in an expansion of the fungicidal spectrum of activity being obtained or in a prevention of fungicide resistance development. Furthermore, in many cases, synergistic effects are obtained.

According to the present invention, it may be preferred that the mixtures comprise besides one compound I and one compound II as component 3) a further active compound or biopesticide, preferably in a synergistically effective amount. Another embodiment relates to mixtures wherein the component 3) is an active compound or biopesticide III selected from groups A') to O'):

A') Respiration inhibitors
  Inhibitors of complex III at $Q_o$ site (e.g. strobilurins): azoxystrobin, coumethoxystrobin, coumoxystrobin, dimoxystrobin, enestroburin, fenaminstrobin, fenoxystrobin/flufenoxystrobin, fluoxastrobin, kresoxim-methyl, metominostrobin, orysastrobin, picoxystrobin, pyraclostrobin, pyrametostrobin, pyraoxystrobin, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl)-phenyl)-2-methoxyimino-N-methyl-acetamide, pyribencarb, triclopyricarb/chlorodincarb, famoxadone, fenamidone;
  inhibitors of complex III at $Q_i$ site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl]2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl]2-methylpropanoate; (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate;
  inhibitors of complex II (e. g. carboxamides): benodanil, benzovindiflupyr, bixafen, boscalid, carboxin, fenfuram, fluopyram, flutolanil, fluxapyroxad, furametpyr, isofetamid, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide, N-(7-fluoro-1,1,3-trimethyl-indan-4-yl)-1,3-dimethyl-pyrazole-4-carboxamide, N-[2-(2,4-dichlorophenyl)-2-methoxy-1-methyl-ethyl]-3-(difluoromethyl)-1-methyl-pyrazole-4-carboxamide;
  other respiration inhibitors (e.g. complex I, uncouplers): diflumetorim, (5,8-difluoroquinazolin-4-yl)-{2-[2-fluoro-4-(4-trifluoromethylpyridin-2-yloxy)-phenyl]-ethyl}-amine; nitrophenyl derivates: binapacryl, dinobuton, dinocap, fluazinam; ferimzone; organometal compounds: fentin salts, such as fentin-acetate, fentin chloride or fentin hydroxide; ametoctradin; and silthiofam;

B') Sterol biosynthesis inhibitors (SBI fungicides)
  C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-[rel-(2S;3R)-3-(2-chlorophenyl)-2-(2,4-difluorophenyl)-oxiranylmethyl]-5-thiocyanato-1H-[1,2,4]triazole, 2-[rel-(2 S;3R)-3-(2-chlorophenyl)-2-(2,4-difluorophenyl)-oxiranylmethyl]-2H-[1,2,4]triazole-3-thiol, 2-[2-chloro-4-(4-chlorophenoxy)phenyl]-1-(1,2,4-triazol-1-yl)pentan-2-ol, 1-[4-(4-chloro-phenoxy)-2-(trifluoromethyl)phenyl]-1-cyclopropyl-2-(1,2,4-triazol-1-yl)ethanol, 2-[4-(4-chloro-phenoxy)-2-(trifluoromethyl)phenyl]-1-(1,2,4-triazol-1-yl)butan-2-ol, 2-[2-chloro-4-(4-chloro-phenoxy)phenyl]-1-(1,2,4-triazol-1-yl)butan-2-ol, 2-[4-(4-chlorophenoxy)-2-(trifluoromethyl)-phenyl]-3-methyl-1-(1,2,4-triazol-1-yl)butan-2-ol, 2-[4-(4-chlorophenoxy)-2-(trifluoromethyl)-phenyl]-1-(1,2,4-triazol-1-yl)propan-2-ol, 2-[2-chloro-4-(4-chlorophenoxy)phenyl]-3-methyl-1-(1,2,4-triazol-1-yl)butan-2-ol, 2-[4-(4-chlorophenoxy)-2-(trifluoromethyl)phenyl]-1-(1,2,4-triazol-1-yl)pentan-2-ol, 2-[4-(4-fluorophenoxy)-2-(trifluoromethyl)phenyl]-1-(1,2,4-triazol-1-yl)-propan-2-ol; imidazoles: imazalil, pefurazoate, prochloraz, triflumizol; pyrimidines, pyridines and piperazines: fenarimol, nuarimol, pyrifenox, triforine, [3-(4-chloro-2-fluoro-phenyl)-5-(2,4-difluorophenyl)isoxazol-4-yl]-(3-pyridyl)methanol;
  Delta14-reductase inhibitors: aldimorph, dodemorph, dodemorph-acetate, fenpropimorph, tridemorph, fenpropidin, piperalin, spiroxamine;
  Inhibitors of 3-keto reductase: fenhexamid;

C') Nucleic acid synthesis inhibitors
  phenylamides or acyl amino acid fungicides: benalaxyl, benalaxyl-M, kiralaxyl, metalaxyl, metalaxyl-M (mefenoxam), ofurace, oxadixyl;
  others: hymexazole, octhilinone, oxolinic acid, bupirimate, 5-fluorocytosine, 5-fluoro-2-(p-tolylmethoxy)pyrimidin-4-amine, 5-fluoro-2-(4-fluorophenylmethoxy)pyrimidin-4-amine;

D') Inhibitors of cell division and cytoskeleton
  tubulin inhibitors, such as benzimidazoles, thiophanates: benomyl, carbendazim, fuberidazole, thiabendazole, thiophanate-methyl; triazolopyrimidines: 5-chloro-7-(4-methyl-piperidin-1-yl)-6-(2,4,6-trifluorophenyl)-[1,2,4]triazolo[1,5-a]pyrimidine;
  other cell division inhibitors: diethofencarb, ethaboxam, pencycuron, fluopicolide, zoxamide, metrafenone, pyriofenone;

E') Inhibitors of amino acid and protein synthesis
  methionine synthesis inhibitors (anilino-pyrimidines): cyprodinil, mepanipyrim, pyrimethanil;
  protein synthesis inhibitors: blasticidin-S, kasugamycin, kasugamycin hydrochloride-hydrate, mildiomycin, streptomycin, oxytetracyclin, polyoxine, validamycin A;

F') Signal transduction inhibitors
MAP/histidine kinase inhibitors: fluoroimid, iprodione, procymidone, vinclozolin, fenpiclonil, fludioxonil;
G protein inhibitors: quinoxyfen;

G') Lipid and membrane synthesis inhibitors
Phospholipid biosynthesis inhibitors: edifenphos, iprobenfos, pyrazophos, isoprothiolane;
lipid peroxidation: dicloran, quintozene, tecnazene, tolclofos-methyl, biphenyl, chloroneb, etridiazole;
phospholipid biosynthesis and cell wall deposition: dimethomorph, flumorph, mandipropamid, pyrimorph, benthiavalicarb, iprovalicarb, valifenalate and N-(1-(1-(4-cyano-phenyl)-ethanesulfonyl)-but-2-yl) carbamic acid-(4-fluorophenyl) ester;
compounds affecting cell membrane permeability and fatty acides: propamocarb, propamocarb-hydrochlorid
fatty acid amide hydrolase inhibitors: oxathiapiprolin, 2-{3-[2-(1-{[3,5-bis(difluoromethyl-1H-pyrazol-1-yl] acetyl}piperidin-4-yl)-1,3-thiazol-4-yl]-4,5-dihydro-1, 2-oxazol-5-yl}phenyl methanesulfonate, 2-{3-[2-(1-{[3,5-bis(difluoromethyl)-1H-pyrazol-1-yl] acetyl}piperidin-4-yl)-1,3-thiazol-4-yl]-4,5-dihydro-1, 2-oxazol-5-yl}-3-chlorophenyl methanesulfonate;

H') Inhibitors with Multi Site Action
inorganic active substances: Bordeaux mixture, copper acetate, copper hydroxide, copper oxychloride, basic copper sulfate, sulfur;
thio- and dithiocarbamates: ferbam, mancozeb, maneb, metam, metiram, propineb, thiram, zineb, ziram;
organochlorine compounds (e.g. phthalimides, sulfamides, chloronitriles): anilazine, chlorothalonil, captafol, captan, folpet, dichlofluanid, dichlorophen, hexachlorobenzene, penta-chlorphenole and its salts, phthalide, tolylfluanid, N-(4-chloro-2-nitro-phenyl)-N-ethyl-4-methyl-benzenesulfonamide;
guanidines and others: guanidine, dodine, dodine free base, guazatine, guazatine-acetate, iminoctadine, iminoctadine-triacetate, iminoctadine-tris(albesilate), dithianon, 2,6-dimethyl-1H,5H-[1,4]dithiino[2,3-c:5,6-c']dipyrrole-1,3,5,7(2H,6H)-tetraone;

I') Cell wall synthesis inhibitors
inhibitors of glucan synthesis: validamycin, polyoxin B;
melanin synthesis inhibitors: pyroquilon, tricyclazole, carpropamid, dicyclomet, fenoxanil;

J') Plant defense inducers
acibenzolar-S-methyl, probenazole, isotianil, tiadinil, prohexadione-calcium; phosphonates: fosetyl, fosetyl-aluminum, phosphorous acid and its salts;

K') Unknown mode of action
bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxathiapiprolin, tolprocarb, 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl] ethanone, 2-[3,5-bis(difluoromethyl)-1H-pyrazol-1-yl]-1-[4-(4-{5-[2-fluoro-6-(prop-2-yn-1-yloxy) phenyl]-4,5-dihydro-1,2-oxazol-3-yl}-1,3-thiazol-2-yl) piperidin-1-yl]ethanone, 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, oxin-copper, proquinazid, tebufloquin, tecloftalam, triazoxide, 2-butoxy-6-iodo-3-propylchromen-4-one, N-(cyclopropylmethoxyimino-(6-difluoromethoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, methoxy-acetic acid 6-tert-butyl-8-fluoro-2,3-dimethyl-quinolin-4-yl ester, 3-[5-(4-methylphenyl)-2,3-dimethyl-isoxazolidin-3-yl]-pyridine, 3-[5-(4-chlorophenyl)-2,3-dimethyl-isoxazolidin-3-yl]-pyridine (pyrisoxazole), N-(6-methoxy-pyridin-3-yl)cyclopropane-carboxylic acid amide, 5-chloro-1-(4,6-dimethoxy-pyrimidin-2-yl)-2-methyl-1H-benzoimida-zole, 2-(4-chloro-phenyl)-N-[4-(3,4-dimethoxy-phenyl)-isoxazol-5-yl]-2-prop-2-ynyloxy-acetamide, ethyl(Z)-3-amino-2-cyano-3-phenyl-prop-2-enoate, tert-butyl N-[6-[[(Z)-[(1-methyltetrazol-5-yl)-phenyl-methylene] amino]oxymethyl]-2-pyridyl]carbamate (picarbutrazox), pentyl N-[6-[[(Z)-[(1-methyltetrazol-5-yl)-phenyl-methylene]amino]oxymethyl]-2-pyridyl] carbamate, 2-[2-[(7,8-difluoro-2-methyl-3-quinolyl) oxy]-6-fluoro-phenyl]propan-2-ol, 2-[2-fluoro-6-[(8-fluoro-2-methyl-3-quinolyl)oxy]phenyl]propan-2-ol, 3-(5-fluoro-3,3,4,4-tetramethyl-3,4-dihydroisoquinolin-1-yl)quinoline, 3-(4,4-difluoro-3,3-dimethyl-3,4-dihydroisoquinolin-1-yl)quinoline, 3-(4,4,5-trifluoro-3,3-dimethyl-3,4-dihydroisoquinolin-1-yl)quinoline, 9-fluoro-2,2-dimethyl-5-(3-quinolyl)-3H-1,4-benzoxazepine;

L') Biopesticides
L'1) Microbial pesticides with fungicidal, bactericidal, viricidal and/or plant defense activator activity: *Ampelomyces quisqualis, Aspergillus flavus, Aureobasidium pullulans, Bacillus altitudinis, B. amyloliquefaciens, B. megaterium, B. mojavensis, B. mycoides, B. pumilus, B. simplex, B. solisalsi, B. subtilis, B. subtilis* var. *amyloliquefaciens, Candida oleophila, C. saitoana, Clavibacter michiganensis* (bacteriophages), *Coniothyrium minitans, Cryphonectria parasitica, Cryptococcus albidus, Dilophosphora alopecuri, Fusarium oxysporum, Clonostachys rosea* f. *catenulate* (also named *Gliocladium catenulatum*), *Gliocladium roseum, Lysobacter antibioticus, L. enzymogenes, Metschnikowia fructicola, Microdochium dimerum, Microsphaeropsis ochracea, Muscodor albus, Paenibacillus alvei, Paenibacillus polymyxa, P. agglomerans, Pantoea vagans, Penicillium bilaiae, Phlebiopsis gigantea, Pseudomonas* sp., *Pseudomonas chloraphis, P. fluorescens, P. putida, Pseudozyma flocculosa, Pichia anomala, Pythium oligandrum, Sphaerodes mycoparasitica, Streptomyces griseoviridis, S. lydicus, S. violaceusniger, Talaromyces flavus, Trichoderma asperellum, T. atroviride, T. fertile, T. gamsii, T. harmatum, T. harzianum, T. polysporum, T. stromaticum, T. virens, T. viride, Typhula phacorrhiza, Ulocladium oudemansii, Verticillium dahlia,* zucchini yellow mosaic virus (avirulent strain);

L'2) Biochemical pesticides with fungicidal, bactericidal, viricidal and/or plant defense activator activity: chitosan (hydrolysate), harpin protein, laminarin, Menhaden fish oil, natamycin, Plum pox virus coat protein, potassium or sodium bicarbonate, *Reynoutria sachalinensis* extract, salicylic acid, tea tree oil;

L'3) Microbial pesticides with insecticidal, acaricidal, molluscidal and/or nematicidal activity: *Agrobacterium radiobacter, Bacillus cereus, B. firmus, B. thuringiensis, B. thuringiensis* ssp. *aizawai, B. t.* ssp. *israelensis, B. t.* ssp. *galleriae, B. t.* ssp. *kurstaki, B. t.* ssp. *tenebrionis, Beauveria bassiana, B. brongniartii, Burkholderia* spp., *Chromobacterium subtsugae, Cydia pomonella* granulovirus (CpGV), *Cryptophlebia leucotreta* granulovirus (CrleGV), *Flavobacterium* spp., *Helicoverpa armigera* nucleopolyhedrovirus (HearNPV), *Heterorhabditis bacteriophora, Isaria fumosorosea, Lecanicillium longisporum, L. muscarium, Metarhizium anisopliae, Metarhizium anisopliae* var. *anisopliae, M. anisopliae* var. *acridum, Nomuraea rileyi, Paecilomyces lilacinus, Paenibacillus popilliae, Pasteuria* spp., *P. nishizawae, P. penetrans, P. ramosa, P. thornea, P. usgae, Pseudomonas fluorescens, Spodoptera littoralis* nucleopolyhedrovirus (SpliNPV), *Steinernema carpocapsae, S. feltiae, S. kraussei, Streptomyces galbus, S. microflavus;*

L'4) Biochemical pesticides with insecticidal, acaricidal, molluscidal, pheromone and/or nematicidal activity: L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, cis-jasmone, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, R-1-octen-3-ol, pentatermanone, potassium silicate, sorbitol actanoate, (E,Z,Z)-3,8,11-tetradecatrienyl acetate, (Z,E)-9,12-tetradecadien-1-yl acetate, Z-7-tetradecen-2-one, Z-9-tetradecen-1-yl acetate, Z-11-tetradecenal, Z-11-tetradecen-1-ol, Acacia negra extract, extract of grapefruit seeds and pulp, extract of *Chenopodium ambrosiodes*, Catnip oil, Neem oil, Quillay extract, Tagetes oil;

L'5) Microbial pesticides with plant stress reducing, plant growth regulator, plant growth promoting and/or yield enhancing activity: *Azospirillum amazonense, A. brasilense, A. lipoferum, A. irakense, A. halopraeferens, Bradyrhizobium* spp., *B. elkanii, B. japonicum, B. liaoningense, B. lupini, Delftia acidovorans, Glomus intraradices, Mesorhizobium* spp., *Rhizobium leguminosarum* bv. *phaseoli, R. l.* bv. *trifolii, R. l.* bv. *viciae, R. tropici, Sinorhizobium meliloti;*

L'6) Biochemical pesticides with plant stress reducing, plant growth regulator and/or plant yield enhancing activity: abscisic acid, aluminium silicate (kaolin), 3-decen-2-one, formononetin, genistein, hesperetin, homobrassinolide, humates, jasmonic acid and its salts or derivatives thereof, lysophosphatidyl ethanolamine, naringenin, polymeric polyhydroxy acid, *Ascophyllum nodosum* (Norwegian kelp, Brown kelp) extract and *Ecklonia maxima* (kelp) extract;

M') Growth regulators
abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole;

N') Herbicides
acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;
amino acid derivatives: bilanafos, glyphosate, glufosinate, sulfosate;
aryloxyphenoxypropionates: clodinafop, cyhalofop-butyl, fenoxaprop, fluazifop, haloxyfop, metamifop, propaquizafop, quizalofop, quizalofop-P-tefuryl;
Bipyridyls: diquat, paraquat;
(thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;
cyclohexanediones: butroxydim, clethodim, cycloxydim, profoxydim, sethoxydim, tepraloxydim, tralkoxydim;
dinitroanilines: benfluralin, ethalfluralin, oryzalin, pendimethalin, prodiamine, trifluralin;
diphenyl ethers: acifluorfen, aclonifen, bifenox, diclofop, ethoxyfen, fomesafen, lactofen, oxyfluorfen;
hydroxybenzonitriles: bomoxynil, dichlobenil, ioxynil;
imidazolinones: imazamethabenz, imazamox, imazapic, imazapyr, imazaquin, imazethapyr;
phenoxy acetic acids: clomeprop, 2,4-dichlorophenoxyacetic acid (2,4-D), 2,4-DB, dichlorprop, MCPA, MCPA-thioethyl, MCPB, Mecoprop;
pyrazines: chloridazon, flufenpyr-ethyl, fluthiacet, norflurazon, pyridate;
pyridines: aminopyralid, clopyralid, diflufenican, dithiopyr, fluridone, fluroxypyr, picloram, picolinafen, thiazopyr;
sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propylimidazo[1,2-b]pyridazin-3-yl)sulfonyl)-3-(4,6-dimethoxy-pyrimidin-2-yl)urea;
triazines: ametryn, atrazine, cyanazine, dimethametryn, ethiozin, hexazinone, metamitron, metribuzin, prometryn, simazine, terbuthylazine, terbutryn, triaziflam;
ureas: chlorotoluron, daimuron, diuron, fluometuron, isoproturon, linuron, metha-benzthiazuron, tebuthiuron, trifludimoxazin;
other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;
others: amicarbazone, aminotriazole, anilofos, beflubutamid, benazolin, bencarbazone, benfluresate, benzofenap, bentazone, benzobicyclon, bicyclopyrone, bromacil, bromobutide, butafenacil, butamifos, cafenstrole, carfentrazone, cinidon-ethyl, chlorthal, cinmethylin, clomazone, cumyluron, cyprosulfamide, dicamba, difenzoquat, diflufenzopyr, *Drechslera monoceras*, endothal, ethofumesate, etobenzanid, fenoxasulfone, fentrazamide, flumiclorac-pentyl, flumioxazin, flupoxam, flurochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester;

O') Insecticides organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

nicotinic receptor agonists/antagonists compounds: clothianidin, dinotefuran, flupyradifurone, imidacloprid, thiamethoxam, nitenpyram, acetamiprid, thiacloprid, 1-2-chloro-thiazol-5-yl-methyl)-2-nitrimino-3,5-dimethyl-[1,3,5]triazinane;

GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;

macrocyclic lactone insecticides: abamectin, emamectin, milbemectin, lepimectin, spinosad, spinetoram;

mitochondrial electron transport inhibitor (METI) I acaricides: fenazaquin, pyridaben, tebufenpyrad, tolfenpyrad, flufenerim;

METI II and III compounds: acequinocyl, fluacyprim, hydramethylnon;

Uncouplers: chlorfenapyr;

oxidative phosphorylation inhibitors: cyhexatin, diafenthiuron, fenbutatin oxide, propargite;

moulting disruptor compounds: cryomazine;

mixed function oxidase inhibitors: piperonyl butoxide;

sodium channel blockers: indoxacarb, metaflumizone;

ryanodine receptor inhibitors: chlorantraniliprole, cyantraniliprole, flubendiamide, N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide; N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide; N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide; N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide; N-[4,6-dichloro-2-[(diethyl-lambda-4-sulfanylidene)carbamoyl]-phenyl]-2-(3-chloro-2-pyridyl)-5-(difluoromethyl)pyrazole-3-carboxamide; N-[4,6-dibromo-2-[(di-2-propyl-lambda-4-sulfanylidene)carbamoyl]-phenyl]-2-(3-chloro-2-pyridyl)-5-(trifluoromethyl)pyrazole-3-carboxamide; N-[4-chloro-2-[(di-2-propyl-lambda-4-sulfanylidene)carbamoyl]-6-cyano-phenyl]-2-(3-chloro-2-pyridyl)-5-(trifluoromethyl)pyrazole-3-carboxamide; N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide;

others: benclothiaz, bifenazate, cartap, flonicamid, pyridalyl, pymetrozine, sulfur, thiocyclam, cyenopyrafen, flupyrazofos, cyflumetofen, amidoflumet, imicyafos, bistrifluron, pyrifluquin-azon and 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl]cyclopropaneacetic acid ester.

The compounds III, their preparation and their biological activity e.g. against harmful fungi, pests or weed is known.

It is preferred that the mixtures comprise as compounds III fungicidal compounds that are independently of each other selected from the groups A'), B'), C'), D'), E'), F'), G'), H'), I'), J'), K') and L').

The biopesticides from group L'1) and/or L'2) may also have insecticidal, acaricidal, molluscidal, pheromone, nematicidal, plant stress reducing, plant growth regulator, plant growth promoting and/or yield enhancing activity. The biopesticides from group L'3) and/or L'4) may also have fungicidal, bactericidal, viricidal, plant defense activator, plant stress reducing, plant growth regulator, plant growth promoting and/or yield enhancing activity. The biopesticides from group L'5) and/or L'6) may also have fungicidal, bactericidal, viricidal, plant defense activator, insecticidal, acaricidal, molluscidal, pheromone and/or nematicidal activity.

According to one embodiment of the inventive mixtures, the component 3) is a biopesticide III from the groups L'1) to L'6) selected from:

L'1) Microbial pesticides with fungicidal, bactericidal, viricidal and/or plant defense activator activity: *Ampelomyces quisqualis* M-10, *Aspergillus flavus* NRRL 21882 (L1.2), *Aureobasidium pullulans* DSM 14940, *A. pullulans* DSM 14941, *Bacillus altitudinis* 41KF2b, *Bacillus amyloliquefaciens* AP-136, *B. amyloliquefaciens* AP-188, *B. amyloliquefaciens* AP-218, *B. amyloliquefaciens*

AP-219, *B. amyloliquefaciens* AP-295, *B. amyloliquefaciens* IN937a, *B. amyloliquefaciens* IT-45, *B. amyloliquefaciens* ssp. *plantarum* D747, *B. amyloliquefaciens* ssp. *plantarum* FZB24, *B. amyloliquefaciens* ssp. *plantarum* FZB42, *B. amyloliquefaciens* ssp. *plantarum* GB03, *B. amyloliquefaciens* ssp. *plantarum* MBI600 (NRRL B-50595), *B. amyloliquefaciens* ssp. *plantarum* QST-713, *B. amyloliquefaciens* ssp. *plantarum* TJ1000, *B. mojavensis* AP-209, *B. mycoides* AQ726, *B. mycoides* strain J, *B. pumilus* INR-7, *B. pumilus* KFP9F, *B. pumilus* QST 2808, *B. pumilus* GHA 180, *B. simplex* ABU 288, *B. solisalsi* AP-217, *B. subtilis* CX-9060, *B. subtilis* FB17, *B. subtilis* GB07, *Candida oleophila* I-82, *C. oleophila* O, *C. saitoana*, *Clavibacter michiganensis* (bacteriophages), *Coniothyrium minitans* CON/M/91-08, *Cryphonectria parasitica*, *Cryptococcus albidus*, *Dilophosphora alopecuri*, *Fusarium oxysporum*, *Clonostachys rosea* f. *catenulata* J1446, *Gliocladium roseum* 321U, *Metschnikowia fructicola* NRRL Y-30752, *Microdochium dimerum*, *Microsphaeropsis ochracea* P130A, *Muscodor albus* QST 20799, *Muscodor albus* SA-13, *Paenibacillus alvei* NAS6G6, *Paenibacillus polymyxa* PKB1, *Pantoea agglomerans* E325, *Pantoea vagans* C9-1, *Penicillium bilaiae* ATCC 22348, *P. bilaiae* ATCC 20851, *Penicillium bilaiae* ATCC 18309, *Phlebiopsis gigantea*, *Pichia anomala* WRL-76, *Pseudomonas* sp. Proradix, *Pseudomonas chlororaphis* MA 342, *P. fluorescens* A506, *P. fluorescens* CL 145A, *P. fluorescens* NCIB 12089, *P. fluorescens* Pf-5, *P. fluorescens* WCS 374, *P. fluorescens* ATCC 13525, *P. fluorescens* CHA0, *P. putida* ATCC 202153, *Pseudozyma flocculosa* PF-A22 UL, *Pythium oligandrum* DV 74, *Sphaerodes mycoparasitica* SMCD2220, *Streptomyces griseoviridis* K61, *S. lydicus* WYEC 108, *S. violaceusniger* XL-2, *S. violaceusniger* YCED-9, *Talaromyces flavus* V117b, *Trichoderma asperellum* T34, *T. asperellum* SKT-1, *T. asperellum* ICC 012, *T. atroviride* LC52, *T. atroviride* CNCM I-1237, *T. fertile* JM41R, *T. gamsii* ICC 080, *T. harmatum* TH 382, *T. harzianum* T-35, *T. harzianum* T-22, *T. harzianum* T-39; mixture of *T. harzianum* ICC012 and *T. viride* ICC080; *T. polysporum; T. stromaticum, T. virens* G1-3, *T. virens* G-41, *T. virens* GL-21, *T. virens* G-41, *T. viride* TV1, *Typhula phacorrhiza* 94671, *Ulocladium oudemansii* HRU3, *Verticillium dahlia*, zucchini yellow mosaic virus (avirulent strain);

L'2) Biochemical pesticides with fungicidal, bactericidal, viricidal and/or plant defense activator activity: chitosan (hydrolysate), harpin protein, laminarin, Menhaden fish oil, natamycin, Plum pox virus coat protein, potassium bicarbonate, *Reynoutria sachalinensis* extract, salicylic acid, potassium or sodium bicarbonate, tea tree oil;

L'3) Microbial pesticides with insecticidal, acaricidal, molluscidal and/or nematicidal activity: *Agrobacterium radiobacter* K1026, *A. radiobacter* K84, *Bacillus firmus* I-1582; *B. thuringiensis* ssp. *aizawai* strains: ABTS-1857, SAN 401 I, ABG-6305 and ABG-6346; *B. t.* ssp. *israelensis* AM65-52, *B. t.* ssp. *israelensis* SUM-6218, *B. t.* ssp. *galleriae* SDS-502, *B. t.* ssp. *kurstaki* EG 2348, *B. t.* ssp. *kurstaki* SB4, *B. t.* ssp. *kurstaki* ABTS-351 (HD-1), *Beauveria bassiana* ATCC 74040, *B. bassiana* GHA, *B. bassiana* H123, *B. bassiana* DSM 12256, *B. bassiana* PPRI 5339, *B. brongniartii*, *Burkholderia* sp. A396, *Chromobacterium subtsugae* PRAA4-1, *Cydia pomonella* granulosis virus V22, *Cydia pomonella* granulosis virus V1, *Cryptophlebia leucotreta* granulovirus (CrleGV), *Flavobacterium* sp. H492, *Helicoverpa armigera* nucleopolyhedrovirus (HearNPV), *Isaria fumosorosea* Apopka-97, *Lecanicillium longisporum* KV42, *L. longisporum* KV71, *L. muscarium* KV01, *Metarhizium anisopliae* FI-985, *M. anisopliae* FI-1045, *M. anisopliae* F52, *M. anisopliae* ICIPE 69, *M. anisopliae* var. *acridum* IMI 330189; *Nomuraea rileyi* strains: SA86101, GU87401, SR86151, CG128 and VA9101; *Paecilomyces fumosoroseus* FE 9901, *P. lilacinus* 251, *P. lilacinus* DSM 15169, *P. lilacinus* BCP2, *Paenibacillus popilliae* Dutky-1940 (NRRL B-2309=ATCC 14706), *P. popilliae* Dutky 1, *P. popilliae* KLN 3, *Pasteuria* sp. Ph3, *Pasteuria* sp. ATCC PTA-9643, *Pasteuria* sp. ATCC SD-5832, *P. nishizawae* Pn1, *P. penetrans*, *P. ramosa*, *P.* sp. Pr-3, *P. thornea*, *P. usgae*, *Pseudomonas fluorescens* CL 145A, *Spodoptera littoralis* nucleopolyhedrovirus (SpliNPV), *Steinernema carpocapsae*, *S. feltiae*, *S. kraussei* L137;

L'4) Biochemical pesticides with insecticidal, acaricidal, molluscidal, pheromone and/or nematicidal activity: L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, cis-jasmone, lavanulyl senecioate, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, R-1-octen-3-ol, pentatermanone, potassium silicate, sorbitol actanoate, (E,Z,Z)-3,8,11-tetradecatrienyl acetate, (Z,E)-9,12-tetradecadien-1-yl acetate, Z-7-tetradecen-2-one, Z-9-tetradecen-1-yl acetate, Z-11-tetradecenal, Z-11-tetradecen-1-ol, Acacia negra extract, extract of grapefruit seeds and pulp, extract of *Chenopodium ambrosiodes*, Catnip oil, Neem oil, Quillay extract, Tagetes oil;

L'5) Microbial pesticides with plant stress reducing, plant growth regulator, plant growth promoting and/or yield enhancing activity: *Azospirillum amazonense* BR 11140 (SpY2), *A. brasilense* Ab-V5, *A. brasilense* Ab-V6, *A. brasilense* AZ39, *A. brasilense* XOH, *A. brasilense* Sp245 (BR 11005), *A. brasilense* BR 11002, *A. lipoferum* BR 11646 (Sp31), *A. irakense*, *A. halopraeferens*, *Bradyrhizobium* sp. PNL01, *B.* sp. (*Arachis*) CB1015, *B.* sp. (*Arachis*) USDA 3446, *B.* sp. (*Arachis*) SEMIA 6144, *B.* sp. (*Arachis*) SEMIA 6462, *B.* sp. (*Arachis*) SEMIA 6464, *B.* sp. (*Vigna*), *B. elkanii* SEMIA 587, *B. elkanii* SEMIA 5019, *B. elkanii* U-1301, *B. elkanii* U-1302, *B. elkanii* USDA 74, *B. elkanii* USDA 76, *B. elkanii* USDA 94, *B. elkanii* USDA 3254, *B. japonicum* 532c, *B. japonicum* CPAC 15, *B. japonicum* E-109, *B. japonicum* G49, *B. japonicum* TA-11, *B. japonicum* USDA 3, *B. japonicum* USDA 31, *B. japonicum* USDA 76, *B. japonicum* USDA 110, *B. japonicum* USDA 121, *B. japonicum* USDA 123, *B. japonicum* USDA 136, *B. japonicum* SEMIA 566, *B. japonicum* SEMIA 5079, *B. japonicum* SEMIA 5080, *B. japonicum* WB74, *B. liaoningense*, *B. lupini* LL13, *B. lupini* WU425, *B. lupini* WSM471, *B. lupini* WSM4024, *Glomus intraradices* RTI-801, *Mesorhizobium* sp. WSM1271, *M.* sp. WSM1497, *M. ciceri* CC1192, *M. huakii*, *M. loti* CC829, *M. loti* SU343, *Rhizobium leguminosarum* bv. *phaseoli* RG-B10, *R. l.* bv. *trifolii* RP113-7, *R. l.* bv. *trifolii* 095, *R. l.* bv. *trifolii* TA1, *R. l.* bv. *trifolii* CC283b, *R. l.* bv. *trifolii* CC275e, *R. l.* bv. *trifolii* CB782, *R. l.* bv. *trifolii* CC1099, *R. l.* bv. *trifolii* WSM1325, *R. l.* bv. *viciae* SU303, *R. l.* bv. *viciae* WSM1455, *R. l.* bv. *viciae* P1NP3Cst, *R. l.* bv. *viciae* RG-P2, *R. tropici* PRF 81, *R. tropici* SEMIA 4077, *R. tropici* CC511(L.5.70), *Sinorhizobium meliloti* RCR2011, *S. meliloti* NRG185, *S. meliloti* RRl128;

L'6) Biochemical pesticides with plant stress reducing, plant growth regulator and/or plant yield enhancing activity: abscisic acid, aluminium silicate (kaolin), 3-decen-2-one, formononectin, genistein, hesperetin, homobrassinolide, humates, methyl jasmonate, cis-jasmone, lysophosphatidyl ethanlamine, naringenin, polymeric polyhydroxy acid, salicylic acid, *Ascophyllum nodosum* (Norwegian kelp, Brown kelp) extract and *Ecklonia maxima* (kelp) extract.

According to another embodiment of the invention, mixtures comprise as compound III a herbicidal compound that is selected from the group N').

According to a further embodiment, mixtures comprise as compound III an insecticidal compound that is selected from the group O').

Preference is also given to mixtures comprise as compound III (component 3) at least one active substance selected from group A') and particularly selected from azoxystrobin, dimoxystrobin, fluoxastrobin, kresoxim-methyl, orysastrobin, picoxystrobin, pyraclostrobin, trifloxystrobin; famoxadone, fenamidone; benzovindiflupyr, bixafen, boscalid, fluopyram, fluxapyroxad, isopyrazam, penflufen, penthiopyrad, sedaxane; ametoctradin, cyazofamid, fluazinam, fentin salts, such as fentin acetate.

Preference is also given to mixtures comprise as compound III (component 3) at least one active substance selected from group B') and particularly selected from cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole, prochloraz, fenarimol, triforine; dodemorph, fenpropimorph, tridemorph, fenpropidin, spiroxamine; fenhexamid.

Preference is also given to mixtures comprise as compound III (component 3) at least one active substance selected from group C') and particularly selected from metalaxyl, (metalaxyl-M) mefenoxam, ofurace.

Preference is also given to mixtures comprise as compound III (component 3) at least one active substance selected from group D') and particularly selected from benomyl, carbendazim, thiophanate-methyl, ethaboxam, fluopicolide, zoxamide, metrafenone, pyriofenone.

Preference is also given to mixtures comprise as compound III (component 3) at least one active substance selected from group E') and particularly selected from cyprodinil, mepanipyrim, pyrimethanil.

Preference is also given to mixtures comprise as compound III (component 3) at least one active substance selected from group F') and particularly selected from iprodione, fludioxonil, vinclozolin, quinoxyfen.

Preference is also given to mixtures comprise as compound III (component 3) at least one active substance selected from group G') and particularly selected from dimethomorph, flumorph, iprovalicarb, benthiavalicarb, mandipropamid, propamocarb.

Preference is also given to mixtures comprise as compound III (component 3) at least one active substance selected from group H') and particularly selected from copper acetate, copper hydroxide, copper oxychloride, copper sulfate, sulfur, mancozeb, metiram, propineb, thiram, captafol, folpet, chlorothalonil, dichlofluanid, dithianon.

Preference is also given to mixtures comprise as compound III (component 3) at least one active substance selected from group I') and particularly selected from carpropamid and fenoxanil.

Preference is also given to mixtures comprise as compound III (component 3) at least one active substance selected from group J') and particularly selected from acibenzolar-S-methyl, probenazole, tiadinil, fosetyl, fosetyl-aluminium, $H_3PO_3$ and salts thereof.

Preference is also given to mixtures comprise as compound III (component 3) at least one active substance selected from group K') and particularly selected from cymoxanil, proquinazid and N-methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide.

Preference is also given to mixtures comprise as compound III (component 3) at least one antifungal biopesticide selected from group L') and particularly selected from *Bacillus subtilis* strain NRRL No. B-21661, *Bacillus pumilus* strain NRRL No. B-30087 and *Ulocladium oudemansii*.

The present invention also relates to mixtures comprising, as active components:

1) at least one fungicidally active compound selected from:

1-[4-(4-chlorophenoxy)-2-(trifluoromethyl)phenyl]-1-cyclopropyl-2-(1,2,4-triazol-1-yl)ethanol (II-2), 2-[4-(4-chlorophenoxy)-2-(trifluoromethyl)phenyl]-3-methyl-1-(1,2,4-triazol-1-yl)butan-2-ol (II-5), 2-[4-(4-chlorophenoxy)-2-(trifluoromethyl)phenyl]-1-(1,2,4-triazol-1-yl)propan-2-ol (II-6) and 1-[2-chloro-4-(4-chlorophenoxy)phenyl]-1-cyclopropyl-2-(1,2,4-triazol-1-yl)ethanol (II-57);

and 2) at least one fungicidally active compound III selected from:

procymidone and isofetamid.

The present invention also relates to mixtures consisting of, as pesticidally active components:

3) one fungicidally active compound II selected from:

1-[4-(4-chlorophenoxy)-2-(trifluoromethyl)phenyl]-1-cyclopropyl-2-(1,2,4-triazol-1-yl)ethanol (II-2), 2-[4-(4-chlorophenoxy)-2-(trifluoromethyl)phenyl]-3-methyl-1-(1,2,4-triazol-1-yl)butan-2-ol (II-5), 2-[4-(4-chlorophenoxy)-2-(trifluoromethyl)phenyl]-1-(1,2,4-triazol-1-yl)propan-2-ol (II-6) and 1-[2-chloro-4-(4-chlorophenoxy)phenyl]-1-cyclopropyl-2-(1,2,4-triazol-1-yl)ethanol (II-57);

and 4) one fungicidally active compound III selected from:

procymidone (III-44) and isofetamid (III-21). These mixtures are useful as fungicides.

TABLE A2

Binary Mixtures A2-1 to A2-8 comprising as active ingredients one compound II as defined and numbered above as component 1) (Co. 1) and one compound III as defined and numbered above as component 2) (Co. 2).

| Mixt. | Co. 1 | Co. 2 |
| --- | --- | --- |
| A2-1 | II-2 | III-44 |
| A2-2 | II-5 | III-44 |
| A2-3 | II-6 | III-44 |
| A2-4 | II-57 | III-44 |
| A2-5 | II-2 | III-21 |
| A2-6 | II-5 | III-21 |
| A2-7 | II-6 | III-21 |
| A2-8 | II-57 | III-21 |

With respect to their use as component 3) (Co. 3) in the inventive ternary mixtures, preference is given to the compounds III which are compiled in the Table B below.

TABLE B

Preferred compounds III for use as component 3) (Co. 3).

| No. | Co. 3 (compound III) |
|---|---|
| III-1 | Fluxapyroxad |
| III-2 | Pyraclostrobin |
| III-3 | Bixafen |
| III-4 | Boscalid |
| III-5 | Isopyrazam |
| III-6 | Fluopyram |
| III-7 | Penflufen |
| III-8 | Sedaxane |
| III-9 | Difenoconazole |
| III-10 | Epoxiconazole |
| III-11 | Metconazole |
| III-12 | Prothioconazole |
| III-13 | Dimethomorph |
| III-14 | Ametoctradin |
| III-15 | Mancozeb |
| III-16 | Metiram |
| III-17 | Chlorothalonil |
| III-18 | Phosphorous acid and its salts |
| III-19 | Benzovindiflupyr |
| III-20 | Penthiopyrad |
| III-21 | Isofetamid |
| III-22 | Dimoxystrobin |
| III-23 | Azoxystrobin |
| III-24 | Fluoxastrobin |
| III-25 | Trifloxystrobin |
| III-26 | Picoxystrobin |
| III-27 | Tebuconazole |
| III-28 | Cyproconazole |
| III-29 | Flusilazole |
| III-30 | Propiconazole |
| III-31 | Prochloraz |
| III-32 | Flutriafol |
| III-33 | Tetraconazole |
| III-34 | Fenpropimorph |
| III-35 | Metrafenone |
| III-36 | Spiroxamine |
| III-37 | Metiram |
| III-38 | Dithianon |
| III-39 | Folpet |
| III-40 | Cyprodinil |
| III-41 | Carbendazim |
| III-42 | Thiophanate-methyl |
| III-43 | Fluazinam |
| III-44 | Procymidone |
| III-45 | Copper hydroxide |
| III-46 | Captan |
| III-47 | Pyrimethanil |
| III-48 | Iprodione |
| III-49 | Cymoxanil |
| III-50 | Prohexadione-Calcium |
| III-51 | Trinexapac-ethyl |
| III-52 | Mepiquat chloride |
| III-53 | Chlormequat chloride |
| III-54 | Ethephon |

The present invention also relates to ternary mixtures comprising, as active components, the active compound II and two active compounds III as defined in each row of Table A3.

TABLE A3

Ternary Mixtures A3-1 to A3-8 comprising as active ingredients one compound II as defined and numbered above as component 1) (Co. 1) and one compound III as defined and numbered above as component 2) (Co. 2) and one further compound III as defined and numbered above as component 3) (Co. 3).

| Mixt. | Co. 1 | Co. 2 | Co. 3 |
|---|---|---|---|
| A3-1 | II-2 | III-15 | III-49 |
| A3-2 | II-5 | III-15 | III-49 |
| A3-3 | II-6 | III-15 | III-49 |
| A3-4 | II-57 | III-15 | III-49 |
| A3-5 | II-2 | III-4 | III-22 |
| A3-6 | II-5 | III-4 | III-22 |
| A3-7 | II-6 | III-4 | III-22 |
| A3-8 | II-57 | III-4 | III-22 |
| A3-9 | II-2 | III-23 | III-32 |
| A3-10 | II-5 | III-23 | III-32 |
| A3-11 | II-6 | III-23 | III-32 |
| A3-12 | II-57 | III-23 | III-32 |
| A3-13 | II-2 | III-23 | III-33 |
| A3-14 | II-5 | III-23 | III-33 |
| A3-15 | II-6 | III-23 | III-33 |
| A3-16 | II-57 | III-23 | III-33 |
| A3-17 | II-2 | III-23 | III-28 |
| A3-18 | II-5 | III-23 | III-28 |
| A3-19 | II-6 | III-23 | III-28 |
| A3-20 | II-57 | III-23 | III-28 |
| A3-21 | II-2 | III-26 | III-28 |
| A3-22 | II-5 | III-26 | III-28 |
| A3-23 | II-6 | III-26 | III-28 |
| A3-24 | II-57 | III-26 | III-28 |
| A3-25 | II-2 | III-24 | III-32 |
| A3-26 | II-5 | III-24 | III-32 |
| A3-27 | II-6 | III-24 | III-32 |
| A3-28 | II-57 | III-24 | III-32 |

Accordingly, the present invention furthermore to the mixtures as defined in Tables B1 to B18, where a row corresponds in each case to a fungicidal composition comprising as component 1) one of the compounds I as defined and numbered above (Co. 1), and as component 2) one of the compounds or biopesticides II as defined and numbered above (Co. 2), and as component 3) the respective compound III from groups A) to K) as defined in table B (Co. 3) stated in the row in question. Preferably, the compositions described comprise the active substances in synergistically effective amounts.

TABLE B1

Ternary mixtures T-1 to T-660 comprising one compound I as defined and numbered above as component 1) (Co. 1) and one compound or biopesticide II as defined and numbered above as component 2) (Co. 2) and one compound III from groups A) to K) as defined and numbered in Table B as component 3) (Co. 3).

| Mixt. | Co. 1 | Co. 2 | Co. 3 |
|---|---|---|---|
| T-1 | I-1 | II-1 | III-1 |
| T-2 | I-1 | II-2 | III-1 |
| T-3 | I-1 | II-2 | III-1 |
| T-4 | I-1 | II-3 | III-1 |
| T-5 | I-1 | II-4 | III-1 |
| T-6 | I-1 | II-5 | III-1 |
| T-7 | I-1 | II-6 | III-1 |
| T-8 | I-1 | II-7 | III-1 |
| T-9 | I-1 | II-8 | III-1 |
| T-10 | I-1 | II-9 | III-1 |
| T-11 | I-1 | II-10 | III-1 |
| T-12 | I-1 | II-11 | III-1 |
| T-13 | I-1 | II-12 | III-1 |
| T-14 | I-1 | II-13 | III-1 |
| T-15 | I-1 | II-14 | III-1 |
| T-16 | I-1 | II-15 | III-1 |
| T-17 | I-1 | II-16 | III-1 |
| T-18 | I-1 | II-17 | III-1 |
| T-19 | I-1 | II-18 | III-1 |
| T-20 | I-1 | II-19 | III-1 |
| T-21 | I-1 | II-20 | III-1 |

TABLE B1-continued

Ternary mixtures T-1 to T-660 comprising one compound I as defined and numbered above as component 1) (Co. 1) and one compound or biopesticide II as defined and numbered above as component 2) (Co. 2) and one compound III from groups A) to K) as defined and numbered in Table B as component 3) (Co. 3).

| Mixt. | Co. 1 | Co. 2 | Co. 3 |
|---|---|---|---|
| T-22 | I-1 | II-21 | III-1 |
| T-23 | I-1 | II-22 | III-1 |
| T-24 | I-1 | II-23 | III-1 |
| T-25 | I-1 | II-24 | III-1 |
| T-26 | I-1 | II-25 | III-1 |
| T-27 | I-1 | II-26 | III-1 |
| T-28 | I-1 | II-27 | III-1 |
| T-29 | I-1 | II-28 | III-1 |
| T-30 | I-1 | II-29 | III-1 |
| T-31 | I-1 | II-30 | III-1 |
| T-32 | I-1 | II-31 | III-1 |
| T-33 | I-1 | II-32 | III-1 |
| T-34 | I-2 | II-1 | III-1 |
| T-35 | I-2 | II-2 | III-1 |
| T-36 | I-2 | II-2 | III-1 |
| T-37 | I-2 | II-3 | III-1 |
| T-38 | I-2 | II-4 | III-1 |
| T-39 | I-2 | II-5 | III-1 |
| T-40 | I-2 | II-6 | III-1 |
| T-41 | I-2 | II-7 | III-1 |
| T-42 | I-2 | II-8 | III-1 |
| T-43 | I-2 | II-9 | III-1 |
| T-44 | I-2 | II-10 | III-1 |
| T-45 | I-2 | II-11 | III-1 |
| T-46 | I-2 | II-12 | III-1 |
| T-47 | I-2 | II-13 | III-1 |
| T-48 | I-2 | II-14 | III-1 |
| T-49 | I-2 | II-15 | III-1 |
| T-50 | I-2 | II-16 | III-1 |
| T-51 | I-2 | II-17 | III-1 |
| T-52 | I-2 | II-18 | III-1 |
| T-53 | I-2 | II-19 | III-1 |
| T-54 | I-2 | II-20 | III-1 |
| T-55 | I-2 | II-21 | III-1 |
| T-56 | I-2 | II-22 | III-1 |
| T-57 | I-2 | II-23 | III-1 |
| T-58 | I-2 | II-24 | III-1 |
| T-59 | I-2 | II-25 | III-1 |
| T-60 | I-2 | II-26 | III-1 |
| T-61 | I-2 | II-27 | III-1 |
| T-62 | I-2 | II-28 | III-1 |
| T-63 | I-2 | II-29 | III-1 |
| T-64 | I-2 | II-30 | III-1 |
| T-65 | I-2 | II-31 | III-1 |
| T-66 | I-2 | II-32 | III-1 |
| T-67 | I-3 | II-1 | III-1 |
| T-68 | I-3 | II-2 | III-1 |
| T-69 | I-3 | II-2 | III-1 |
| T-70 | I-3 | II-3 | III-1 |
| T-71 | I-3 | II-4 | III-1 |
| T-72 | I-3 | II-5 | III-1 |
| T-73 | I-3 | II-6 | III-1 |
| T-74 | I-3 | II-7 | III-1 |
| T-75 | I-3 | II-8 | III-1 |
| T-76 | I-3 | II-9 | III-1 |
| T-77 | I-3 | II-10 | III-1 |
| T-78 | I-3 | II-11 | III-1 |
| T-79 | I-3 | II-12 | III-1 |
| T-80 | I-3 | II-13 | III-1 |
| T-81 | I-3 | II-14 | III-1 |
| T-82 | I-3 | II-15 | III-1 |
| T-83 | I-3 | II-16 | III-1 |
| T-84 | I-3 | II-17 | III-1 |
| T-85 | I-3 | II-18 | III-1 |
| T-86 | I-3 | II-19 | III-1 |
| T-87 | I-3 | II-20 | III-1 |
| T-88 | I-3 | II-21 | III-1 |
| T-89 | I-3 | II-22 | III-1 |
| T-90 | I-3 | II-23 | III-1 |
| T-91 | I-3 | II-24 | III-1 |
| T-92 | I-3 | II-25 | III-1 |
| T-93 | I-3 | II-26 | III-1 |
| T-94 | I-3 | II-27 | III-1 |
| T-95 | I-3 | II-28 | III-1 |
| T-96 | I-3 | II-29 | III-1 |
| T-97 | I-3 | II-30 | III-1 |
| T-98 | I-3 | II-31 | III-1 |
| T-99 | I-3 | II-32 | III-1 |
| T-100 | I-4 | II-1 | III-1 |
| T-101 | I-4 | II-2 | III-1 |
| T-102 | I-4 | II-2 | III-1 |
| T-103 | I-4 | II-3 | III-1 |
| T-104 | I-4 | II-4 | III-1 |
| T-105 | I-4 | II-5 | III-1 |
| T-106 | I-4 | II-6 | III-1 |
| T-107 | I-4 | II-7 | III-1 |
| T-108 | I-4 | II-8 | III-1 |
| T-109 | I-4 | II-9 | III-1 |
| T-110 | I-4 | II-10 | III-1 |
| T-111 | I-4 | II-11 | III-1 |
| T-112 | I-4 | II-12 | III-1 |
| T-113 | I-4 | II-13 | III-1 |
| T-114 | I-4 | II-14 | III-1 |
| T-115 | I-4 | II-15 | III-1 |
| T-116 | I-4 | II-16 | III-1 |
| T-117 | I-4 | II-17 | III-1 |
| T-118 | I-4 | II-18 | III-1 |
| T-119 | I-4 | II-19 | III-1 |
| T-120 | I-4 | II-20 | III-1 |
| T-121 | I-4 | II-21 | III-1 |
| T-122 | I-4 | II-22 | III-1 |
| T-123 | I-4 | II-23 | III-1 |
| T-124 | I-4 | II-24 | III-1 |
| T-125 | I-4 | II-25 | III-1 |
| T-126 | I-4 | II-26 | III-1 |
| T-127 | I-4 | II-27 | III-1 |
| T-128 | I-4 | II-28 | III-1 |
| T-129 | I-4 | II-29 | III-1 |
| T-130 | I-4 | II-30 | III-1 |
| T-131 | I-4 | II-31 | III-1 |
| T-132 | I-4 | II-32 | III-1 |
| T-133 | I-5 | II-1 | III-1 |
| T-134 | I-5 | II-2 | III-1 |
| T-135 | I-5 | II-2 | III-1 |
| T-136 | I-5 | II-3 | III-1 |
| T-137 | I-5 | II-4 | III-1 |
| T-138 | I-5 | II-5 | III-1 |
| T-139 | I-5 | II-6 | III-1 |
| T-140 | I-5 | II-7 | III-1 |
| T-141 | I-5 | II-8 | III-1 |
| T-142 | I-5 | II-9 | III-1 |
| T-143 | I-5 | II-10 | III-1 |
| T-144 | I-5 | II-11 | III-1 |
| T-145 | I-5 | II-12 | III-1 |
| T-146 | I-5 | II-13 | III-1 |
| T-147 | I-5 | II-14 | III-1 |
| T-148 | I-5 | II-15 | III-1 |
| T-149 | I-5 | II-16 | III-1 |
| T-150 | I-5 | II-17 | III-1 |
| T-151 | I-5 | II-18 | III-1 |
| T-152 | I-5 | II-19 | III-1 |
| T-153 | I-5 | II-20 | III-1 |
| T-154 | I-5 | II-21 | III-1 |
| T-155 | I-5 | II-22 | III-1 |
| T-156 | I-5 | II-23 | III-1 |
| T-157 | I-5 | II-24 | III-1 |
| T-158 | I-5 | II-25 | III-1 |
| T-159 | I-5 | II-26 | III-1 |
| T-160 | I-5 | II-27 | III-1 |
| T-161 | I-5 | II-28 | III-1 |
| T-162 | I-5 | II-29 | III-1 |
| T-163 | I-5 | II-30 | III-1 |
| T-164 | I-5 | II-31 | III-1 |
| T-165 | I-5 | II-32 | III-1 |

TABLE B1-continued

Ternary mixtures T-1 to T-660 comprising one compound I as defined and numbered above as component 1) (Co. 1) and one compound or biopesticide II as defined and numbered above as component 2) (Co. 2) and one compound III from groups A) to K) as defined and numbered in Table B as component 3) (Co. 3).

| Mixt. | Co. 1 | Co. 2 | Co. 3 |
|---|---|---|---|
| T-166 | I-6 | II-1 | III-1 |
| T-167 | I-6 | II-2 | III-1 |
| T-168 | I-6 | II-2 | III-1 |
| T-169 | I-6 | II-3 | III-1 |
| T-170 | I-6 | II-4 | III-1 |
| T-171 | I-6 | II-5 | III-1 |
| T-172 | I-6 | II-6 | III-1 |
| T-173 | I-6 | II-7 | III-1 |
| T-174 | I-6 | II-8 | III-1 |
| T-175 | I-6 | II-9 | III-1 |
| T-176 | I-6 | II-10 | III-1 |
| T-177 | I-6 | II-11 | III-1 |
| T-178 | I-6 | II-12 | III-1 |
| T-179 | I-6 | II-13 | III-1 |
| T-180 | I-6 | II-14 | III-1 |
| T-181 | I-6 | II-15 | III-1 |
| T-182 | I-6 | II-16 | III-1 |
| T-183 | I-6 | II-17 | III-1 |
| T-184 | I-6 | II-18 | III-1 |
| T-185 | I-6 | II-19 | III-1 |
| T-186 | I-6 | II-20 | III-1 |
| T-187 | I-6 | II-21 | III-1 |
| T-188 | I-6 | II-22 | III-1 |
| T-189 | I-6 | II-23 | III-1 |
| T-190 | I-6 | II-24 | III-1 |
| T-191 | I-6 | II-25 | III-1 |
| T-192 | I-6 | II-26 | III-1 |
| T-193 | I-6 | II-27 | III-1 |
| T-194 | I-6 | II-28 | III-1 |
| T-195 | I-6 | II-29 | III-1 |
| T-196 | I-6 | II-30 | III-1 |
| T-197 | I-6 | II-31 | III-1 |
| T-198 | I-6 | II-32 | III-1 |
| T-199 | I-7 | II-1 | III-1 |
| T-200 | I-7 | II-2 | III-1 |
| T-201 | I-7 | II-2 | III-1 |
| T-202 | I-7 | II-3 | III-1 |
| T-203 | I-7 | II-4 | III-1 |
| T-204 | I-7 | II-5 | III-1 |
| T-205 | I-7 | II-6 | III-1 |
| T-206 | I-7 | II-7 | III-1 |
| T-207 | I-7 | II-8 | III-1 |
| T-208 | I-7 | II-9 | III-1 |
| T-209 | I-7 | II-10 | III-1 |
| T-210 | I-7 | II-11 | III-1 |
| T-211 | I-7 | II-12 | III-1 |
| T-212 | I-7 | II-13 | III-1 |
| T-213 | I-7 | II-14 | III-1 |
| T-214 | I-7 | II-15 | III-1 |
| T-215 | I-7 | II-16 | III-1 |
| T-216 | I-7 | II-17 | III-1 |
| T-217 | I-7 | II-18 | III-1 |
| T-218 | I-7 | II-19 | III-1 |
| T-219 | I-7 | II-20 | III-1 |
| T-220 | I-7 | II-21 | III-1 |
| T-221 | I-7 | II-22 | III-1 |
| T-222 | I-7 | II-23 | III-1 |
| T-223 | I-7 | II-24 | III-1 |
| T-224 | I-7 | II-25 | III-1 |
| T-225 | I-7 | II-26 | III-1 |
| T-226 | I-7 | II-27 | III-1 |
| T-227 | I-7 | II-28 | III-1 |
| T-228 | I-7 | II-29 | III-1 |
| T-229 | I-7 | II-30 | III-1 |
| T-230 | I-7 | II-31 | III-1 |
| T-231 | I-7 | II-32 | III-1 |
| T-232 | I-8 | II-1 | III-1 |
| T-233 | I-8 | II-2 | III-1 |
| T-234 | I-8 | II-2 | III-1 |
| T-235 | I-8 | II-3 | III-1 |
| T-236 | I-8 | II-4 | III-1 |
| T-237 | I-8 | II-5 | III-1 |
| T-238 | I-8 | II-6 | III-1 |
| T-239 | I-8 | II-7 | III-1 |
| T-240 | I-8 | II-8 | III-1 |
| T-241 | I-8 | II-9 | III-1 |
| T-242 | I-8 | II-10 | III-1 |
| T-243 | I-8 | II-11 | III-1 |
| T-244 | I-8 | II-12 | III-1 |
| T-245 | I-8 | II-13 | III-1 |
| T-246 | I-8 | II-14 | III-1 |
| T-247 | I-8 | II-15 | III-1 |
| T-248 | I-8 | II-16 | III-1 |
| T-249 | I-8 | II-17 | III-1 |
| T-250 | I-8 | II-18 | III-1 |
| T-251 | I-8 | II-19 | III-1 |
| T-252 | I-8 | II-20 | III-1 |
| T-253 | I-8 | II-21 | III-1 |
| T-254 | I-8 | II-22 | III-1 |
| T-255 | I-8 | II-23 | III-1 |
| T-256 | I-8 | II-24 | III-1 |
| T-257 | I-8 | II-25 | III-1 |
| T-258 | I-8 | II-26 | III-1 |
| T-259 | I-8 | II-27 | III-1 |
| T-260 | I-8 | II-28 | III-1 |
| T-261 | I-8 | II-29 | III-1 |
| T-262 | I-8 | II-30 | III-1 |
| T-263 | I-8 | II-31 | III-1 |
| T-264 | I-8 | II-32 | III-1 |
| T-265 | I-9 | II-1 | III-1 |
| T-266 | I-9 | II-2 | III-1 |
| T-267 | I-9 | II-2 | III-1 |
| T-268 | I-9 | II-3 | III-1 |
| T-269 | I-9 | II-4 | III-1 |
| T-270 | I-9 | II-5 | III-1 |
| T-271 | I-9 | II-6 | III-1 |
| T-272 | I-9 | II-7 | III-1 |
| T-273 | I-9 | II-8 | III-1 |
| T-274 | I-9 | II-9 | III-1 |
| T-275 | I-9 | II-10 | III-1 |
| T-276 | I-9 | II-11 | III-1 |
| T-277 | I-9 | II-12 | III-1 |
| T-278 | I-9 | II-13 | III-1 |
| T-279 | I-9 | II-14 | III-1 |
| T-280 | I-9 | II-15 | III-1 |
| T-281 | I-9 | II-16 | III-1 |
| T-282 | I-9 | II-17 | III-1 |
| T-283 | I-9 | II-18 | III-1 |
| T-284 | I-9 | II-19 | III-1 |
| T-285 | I-9 | II-20 | III-1 |
| T-286 | I-9 | II-21 | III-1 |
| T-287 | I-9 | II-22 | III-1 |
| T-288 | I-9 | II-23 | III-1 |
| T-289 | I-9 | II-24 | III-1 |
| T-290 | I-9 | II-25 | III-1 |
| T-291 | I-9 | II-26 | III-1 |
| T-292 | I-9 | II-27 | III-1 |
| T-293 | I-9 | II-28 | III-1 |
| T-294 | I-9 | II-29 | III-1 |
| T-295 | I-9 | II-30 | III-1 |
| T-296 | I-9 | II-31 | III-1 |
| T-297 | I-9 | II-32 | III-1 |
| T-298 | I-10 | II-1 | III-1 |
| T-299 | I-10 | II-2 | III-1 |
| T-300 | I-10 | II-2 | III-1 |
| T-301 | I-10 | II-3 | III-1 |
| T-302 | I-10 | II-4 | III-1 |
| T-303 | I-10 | II-5 | III-1 |
| T-304 | I-10 | II-6 | III-1 |
| T-305 | I-10 | II-7 | III-1 |
| T-306 | I-10 | II-8 | III-1 |
| T-307 | I-10 | II-9 | III-1 |
| T-308 | I-10 | II-10 | III-1 |
| T-309 | I-10 | II-11 | III-1 |

TABLE B1-continued

Ternary mixtures T-1 to T-660 comprising one compound I as defined and numbered above as component 1) (Co. 1) and one compound or biopesticide II as defined and numbered above as component 2) (Co. 2) and one compound III from groups A) to K) as defined and numbered in Table B as component 3) (Co. 3).

| Mixt. | Co. 1 | Co. 2 | Co. 3 |
|---|---|---|---|
| T-310 | I-10 | II-12 | III-1 |
| T-311 | I-10 | II-13 | III-1 |
| T-312 | I-10 | II-14 | III-1 |
| T-313 | I-10 | II-15 | III-1 |
| T-314 | I-10 | II-16 | III-1 |
| T-315 | I-10 | II-17 | III-1 |
| T-316 | I-10 | II-18 | III-1 |
| T-317 | I-10 | II-19 | III-1 |
| T-318 | I-10 | II-20 | III-1 |
| T-319 | I-10 | II-21 | III-1 |
| T-320 | I-10 | II-22 | III-1 |
| T-321 | I-10 | II-23 | III-1 |
| T-322 | I-10 | II-24 | III-1 |
| T-323 | I-10 | II-25 | III-1 |
| T-324 | I-10 | II-26 | III-1 |
| T-325 | I-10 | II-27 | III-1 |
| T-326 | I-10 | II-28 | III-1 |
| T-327 | I-10 | II-29 | III-1 |
| T-328 | I-10 | II-30 | III-1 |
| T-329 | I-10 | II-31 | III-1 |
| T-330 | I-10 | II-32 | III-1 |
| T-331 | I-11 | II-1 | III-1 |
| T-332 | I-11 | II-2 | III-1 |
| T-333 | I-11 | II-2 | III-1 |
| T-334 | I-11 | II-3 | III-1 |
| T-335 | I-11 | II-4 | III-1 |
| T-336 | I-11 | II-5 | III-1 |
| T-337 | I-11 | II-6 | III-1 |
| T-338 | I-11 | II-7 | III-1 |
| T-339 | I-11 | II-8 | III-1 |
| T-340 | I-11 | II-9 | III-1 |
| T-341 | I-11 | II-10 | III-1 |
| T-342 | I-11 | II-11 | III-1 |
| T-343 | I-11 | II-12 | III-1 |
| T-344 | I-11 | II-13 | III-1 |
| T-345 | I-11 | II-14 | III-1 |
| T-346 | I-11 | II-15 | III-1 |
| T-347 | I-11 | II-16 | III-1 |
| T-348 | I-11 | II-17 | III-1 |
| T-349 | I-11 | II-18 | III-1 |
| T-350 | I-11 | II-19 | III-1 |
| T-351 | I-11 | II-20 | III-1 |
| T-352 | I-11 | II-21 | III-1 |
| T-353 | I-11 | II-22 | III-1 |
| T-354 | I-11 | II-23 | III-1 |
| T-355 | I-11 | II-24 | III-1 |
| T-356 | I-11 | II-25 | III-1 |
| T-357 | I-11 | II-26 | III-1 |
| T-358 | I-11 | II-27 | III-1 |
| T-359 | I-11 | II-28 | III-1 |
| T-360 | I-11 | II-29 | III-1 |
| T-361 | I-11 | II-30 | III-1 |
| T-362 | I-11 | II-31 | III-1 |
| T-363 | I-11 | II-32 | III-1 |
| T-364 | I-12 | II-1 | III-1 |
| T-365 | I-12 | II-2 | III-1 |
| T-366 | I-12 | II-2 | III-1 |
| T-367 | I-12 | II-3 | III-1 |
| T-368 | I-12 | II-4 | III-1 |
| T-369 | I-12 | II-5 | III-1 |
| T-370 | I-12 | II-6 | III-1 |
| T-371 | I-12 | II-7 | III-1 |
| T-372 | I-12 | II-8 | III-1 |
| T-373 | I-12 | II-9 | III-1 |
| T-374 | I-12 | II-10 | III-1 |
| T-375 | I-12 | II-11 | III-1 |
| T-376 | I-12 | II-12 | III-1 |
| T-377 | I-12 | II-13 | III-1 |
| T-378 | I-12 | II-14 | III-1 |
| T-379 | I-12 | II-15 | III-1 |
| T-380 | I-12 | II-16 | III-1 |
| T-381 | I-12 | II-17 | III-1 |
| T-382 | I-12 | II-18 | III-1 |
| T-383 | I-12 | II-19 | III-1 |
| T-384 | I-12 | II-20 | III-1 |
| T-385 | I-12 | II-21 | III-1 |
| T-386 | I-12 | II-22 | III-1 |
| T-387 | I-12 | II-23 | III-1 |
| T-388 | I-12 | II-24 | III-1 |
| T-389 | I-12 | II-25 | III-1 |
| T-390 | I-12 | II-26 | III-1 |
| T-391 | I-12 | II-27 | III-1 |
| T-392 | I-12 | II-28 | III-1 |
| T-393 | I-12 | II-29 | III-1 |
| T-394 | I-12 | II-30 | III-1 |
| T-395 | I-12 | II-31 | III-1 |
| T-396 | I-12 | II-32 | III-1 |
| T-397 | I-1 | II-56 | III-1 |
| T-398 | I-1 | II-57 | III-1 |
| T-399 | I-1 | II-58 | III-1 |
| T-400 | I-1 | II-59 | III-1 |
| T-401 | I-1 | II-60 | III-1 |
| T-402 | I-1 | II-61 | III-1 |
| T-403 | I-1 | II-62 | III-1 |
| T-404 | I-1 | II-63 | III-1 |
| T-405 | I-1 | II-64 | III-1 |
| T-406 | I-1 | II-65 | III-1 |
| T-407 | I-1 | II-66 | III-1 |
| T-408 | I-1 | II-67 | III-1 |
| T-409 | I-1 | II-68 | III-1 |
| T-410 | I-1 | II-69 | III-1 |
| T-411 | I-1 | II-70 | III-1 |
| T-412 | I-1 | II-71 | III-1 |
| T-413 | I-1 | II-72 | III-1 |
| T-414 | I-1 | II-73 | III-1 |
| T-415 | I-1 | II-74 | III-1 |
| T-416 | I-1 | II-75 | III-1 |
| T-417 | I-1 | II-76 | III-1 |
| T-418 | I-1 | II-77 | III-1 |
| T-419 | I-2 | II-56 | III-1 |
| T-420 | I-2 | II-57 | III-1 |
| T-421 | I-2 | II-58 | III-1 |
| T-422 | I-2 | II-59 | III-1 |
| T-423 | I-2 | II-60 | III-1 |
| T-424 | I-2 | II-61 | III-1 |
| T-425 | I-2 | II-62 | III-1 |
| T-426 | I-2 | II-63 | III-1 |
| T-427 | I-2 | II-64 | III-1 |
| T-428 | I-2 | II-65 | III-1 |
| T-429 | I-2 | II-66 | III-1 |
| T-430 | I-2 | II-67 | III-1 |
| T-431 | I-2 | II-68 | III-1 |
| T-432 | I-2 | II-69 | III-1 |
| T-433 | I-2 | II-70 | III-1 |
| T-434 | I-2 | II-71 | III-1 |
| T-435 | I-2 | II-72 | III-1 |
| T-436 | I-2 | II-73 | III-1 |
| T-437 | I-2 | II-74 | III-1 |
| T-438 | I-2 | II-75 | III-1 |
| T-439 | I-2 | II-76 | III-1 |
| T-440 | I-2 | II-77 | III-1 |
| T-441 | I-3 | II-56 | III-1 |
| T-442 | I-3 | II-57 | III-1 |
| T-443 | I-3 | II-58 | III-1 |
| T-444 | I-3 | II-59 | III-1 |
| T-445 | I-3 | II-60 | III-1 |
| T-446 | I-3 | II-61 | III-1 |
| T-447 | I-3 | II-62 | III-1 |
| T-448 | I-3 | II-63 | III-1 |
| T-449 | I-3 | II-64 | III-1 |
| T-450 | I-3 | II-65 | III-1 |
| T-451 | I-3 | II-66 | III-1 |
| T-452 | I-3 | II-67 | III-1 |
| T-453 | I-3 | II-68 | III-1 |

TABLE B1-continued

Ternary mixtures T-1 to T-660 comprising one compound I as defined and numbered above as component 1) (Co. 1) and one compound or biopesticide II as defined and numbered above as component 2) (Co. 2) and one compound III from groups A) to K) as defined and numbered in Table B as component 3) (Co. 3).

| Mixt. | Co. 1 | Co. 2 | Co. 3 |
|---|---|---|---|
| T-454 | I-3 | II-69 | III-1 |
| T-455 | I-3 | II-70 | III-1 |
| T-456 | I-3 | II-71 | III-1 |
| T-457 | I-3 | II-72 | III-1 |
| T-458 | I-3 | II-73 | III-1 |
| T-459 | I-3 | II-74 | III-1 |
| T-460 | I-3 | II-75 | III-1 |
| T-461 | I-3 | II-76 | III-1 |
| T-462 | I-3 | II-77 | III-1 |
| T-463 | I-4 | II-56 | III-1 |
| T-464 | I-4 | II-57 | III-1 |
| T-465 | I-4 | II-58 | III-1 |
| T-466 | I-4 | II-59 | III-1 |
| T-467 | I-4 | II-60 | III-1 |
| T-468 | I-4 | II-61 | III-1 |
| T-469 | I-4 | II-62 | III-1 |
| T-470 | I-4 | II-63 | III-1 |
| T-471 | I-4 | II-64 | III-1 |
| T-472 | I-4 | II-65 | III-1 |
| T-473 | I-4 | II-66 | III-1 |
| T-474 | I-4 | II-67 | III-1 |
| T-475 | I-4 | II-68 | III-1 |
| T-476 | I-4 | II-69 | III-1 |
| T-477 | I-4 | II-70 | III-1 |
| T-478 | I-4 | II-71 | III-1 |
| T-479 | I-4 | II-72 | III-1 |
| T-480 | I-4 | II-73 | III-1 |
| T-481 | I-4 | II-74 | III-1 |
| T-482 | I-4 | II-75 | III-1 |
| T-483 | I-4 | II-76 | III-1 |
| T-484 | I-4 | II-77 | III-1 |
| T-485 | I-5 | II-56 | III-1 |
| T-486 | I-5 | II-57 | III-1 |
| T-487 | I-5 | II-58 | III-1 |
| T-488 | I-5 | II-59 | III-1 |
| T-489 | I-5 | II-60 | III-1 |
| T-490 | I-5 | II-61 | III-1 |
| T-491 | I-5 | II-62 | III-1 |
| T-492 | I-5 | II-63 | III-1 |
| T-493 | I-5 | II-64 | III-1 |
| T-494 | I-5 | II-65 | III-1 |
| T-495 | I-5 | II-66 | III-1 |
| T-496 | I-5 | II-67 | III-1 |
| T-497 | I-5 | II-68 | III-1 |
| T-498 | I-5 | II-69 | III-1 |
| T-499 | I-5 | II-70 | III-1 |
| T-500 | I-5 | II-71 | III-1 |
| T-501 | I-5 | II-72 | III-1 |
| T-502 | I-5 | II-73 | III-1 |
| T-503 | I-5 | II-74 | III-1 |
| T-504 | I-5 | II-75 | III-1 |
| T-505 | I-5 | II-76 | III-1 |
| T-506 | I-5 | II-77 | III-1 |
| T-507 | I-6 | II-56 | III-1 |
| T-508 | I-6 | II-57 | III-1 |
| T-509 | I-6 | II-58 | III-1 |
| T-510 | I-6 | II-59 | III-1 |
| T-511 | I-6 | II-60 | III-1 |
| T-512 | I-6 | II-61 | III-1 |
| T-513 | I-6 | II-62 | III-1 |
| T-514 | I-6 | II-63 | III-1 |
| T-515 | I-6 | II-64 | III-1 |
| T-516 | I-6 | II-65 | III-1 |
| T-517 | I-6 | II-66 | III-1 |
| T-518 | I-6 | II-67 | III-1 |
| T-519 | I-6 | II-68 | III-1 |
| T-520 | I-6 | II-69 | III-1 |
| T-521 | I-6 | II-70 | III-1 |
| T-522 | I-6 | II-71 | III-1 |
| T-523 | I-6 | II-72 | III-1 |
| T-524 | I-6 | II-73 | III-1 |
| T-525 | I-6 | II-74 | III-1 |
| T-526 | I-6 | II-75 | III-1 |
| T-527 | I-6 | II-76 | III-1 |
| T-528 | I-6 | II-77 | III-1 |
| T-529 | I-7 | II-56 | III-1 |
| T-530 | I-7 | II-57 | III-1 |
| T-531 | I-7 | II-58 | III-1 |
| T-532 | I-7 | II-59 | III-1 |
| T-533 | I-7 | II-60 | III-1 |
| T-534 | I-7 | II-61 | III-1 |
| T-535 | I-7 | II-62 | III-1 |
| T-536 | I-7 | II-63 | III-1 |
| T-537 | I-7 | II-64 | III-1 |
| T-538 | I-7 | II-65 | III-1 |
| T-539 | I-7 | II-66 | III-1 |
| T-540 | I-7 | II-67 | III-1 |
| T-541 | I-7 | II-68 | III-1 |
| T-542 | I-7 | II-69 | III-1 |
| T-543 | I-7 | II-70 | III-1 |
| T-544 | I-7 | II-71 | III-1 |
| T-545 | I-7 | II-72 | III-1 |
| T-546 | I-7 | II-73 | III-1 |
| T-547 | I-7 | II-74 | III-1 |
| T-548 | I-7 | II-75 | III-1 |
| T-549 | I-7 | II-76 | III-1 |
| T-550 | I-7 | II-77 | III-1 |
| T-551 | I-8 | II-56 | III-1 |
| T-552 | I-8 | II-57 | III-1 |
| T-553 | I-8 | II-58 | III-1 |
| T-554 | I-8 | II-59 | III-1 |
| T-555 | I-8 | II-60 | III-1 |
| T-556 | I-8 | II-61 | III-1 |
| T-557 | I-8 | II-62 | III-1 |
| T-558 | I-8 | II-63 | III-1 |
| T-559 | I-8 | II-64 | III-1 |
| T-560 | I-8 | II-65 | III-1 |
| T-561 | I-8 | II-66 | III-1 |
| T-562 | I-8 | II-67 | III-1 |
| T-563 | I-8 | II-68 | III-1 |
| T-564 | I-8 | II-69 | III-1 |
| T-565 | I-8 | II-70 | III-1 |
| T-566 | I-8 | II-71 | III-1 |
| T-567 | I-8 | II-72 | III-1 |
| T-568 | I-8 | II-73 | III-1 |
| T-569 | I-8 | II-74 | III-1 |
| T-570 | I-8 | II-75 | III-1 |
| T-571 | I-8 | II-76 | III-1 |
| T-572 | I-8 | II-77 | III-1 |
| T-573 | I-9 | II-56 | III-1 |
| T-574 | I-9 | II-57 | III-1 |
| T-575 | I-9 | II-58 | III-1 |
| T-576 | I-9 | II-59 | III-1 |
| T-577 | I-9 | II-60 | III-1 |
| T-578 | I-9 | II-61 | III-1 |
| T-579 | I-9 | II-62 | III-1 |
| T-580 | I-9 | II-63 | III-1 |
| T-581 | I-9 | II-64 | III-1 |
| T-582 | I-9 | II-65 | III-1 |
| T-583 | I-9 | II-66 | III-1 |
| T-584 | I-9 | II-67 | III-1 |
| T-585 | I-9 | II-68 | III-1 |
| T-586 | I-9 | II-69 | III-1 |
| T-587 | I-9 | II-70 | III-1 |
| T-588 | I-9 | II-71 | III-1 |
| T-589 | I-9 | II-72 | III-1 |
| T-590 | I-9 | II-73 | III-1 |
| T-591 | I-9 | II-74 | III-1 |
| T-592 | I-9 | II-75 | III-1 |
| T-593 | I-9 | II-76 | III-1 |
| T-594 | I-9 | II-77 | III-1 |
| T-595 | I-10 | II-56 | III-1 |
| T-596 | I-10 | II-57 | III-1 |
| T-597 | I-10 | II-58 | III-1 |

TABLE B1-continued

Ternary mixtures T-1 to T-660 comprising one compound I as defined and numbered above as component 1) (Co. 1) and one compound or biopesticide II as defined and numbered above as component 2) (Co. 2) and one compound III from groups A) to K) as defined and numbered in Table B as component 3) (Co. 3).

| Mixt. | Co. 1 | Co. 2 | Co. 3 |
|---|---|---|---|
| T-598 | I-10 | II-59 | III-1 |
| T-599 | I-10 | II-60 | III-1 |
| T-600 | I-10 | II-61 | III-1 |
| T-601 | I-10 | II-62 | III-1 |
| T-602 | I-10 | II-63 | III-1 |
| T-603 | I-10 | II-64 | III-1 |
| T-604 | I-10 | II-65 | III-1 |
| T-605 | I-10 | II-66 | III-1 |
| T-606 | I-10 | II-67 | III-1 |
| T-607 | I-10 | II-68 | III-1 |
| T-608 | I-10 | II-69 | III-1 |
| T-609 | I-10 | II-70 | III-1 |
| T-610 | I-10 | II-71 | III-1 |
| T-611 | I-10 | II-72 | III-1 |
| T-612 | I-10 | II-73 | III-1 |
| T-613 | I-10 | II-74 | III-1 |
| T-614 | I-10 | II-75 | III-1 |
| T-615 | I-10 | II-76 | III-1 |
| T-616 | I-10 | II-77 | III-1 |
| T-617 | I-11 | II-56 | III-1 |
| T-618 | I-11 | II-57 | III-1 |
| T-619 | I-11 | II-58 | III-1 |
| T-620 | I-11 | II-59 | III-1 |
| T-621 | I-11 | II-60 | III-1 |
| T-622 | I-11 | II-61 | III-1 |
| T-623 | I-11 | II-62 | III-1 |
| T-624 | I-11 | II-63 | III-1 |
| T-625 | I-11 | II-64 | III-1 |
| T-626 | I-11 | II-65 | III-1 |
| T-627 | I-11 | II-66 | III-1 |
| T-628 | I-11 | II-67 | III-1 |
| T-629 | I-11 | II-68 | III-1 |
| T-630 | I-11 | II-69 | III-1 |
| T-631 | I-11 | II-70 | III-1 |
| T-632 | I-11 | II-71 | III-1 |
| T-633 | I-11 | II-72 | III-1 |
| T-634 | I-11 | II-73 | III-1 |
| T-635 | I-11 | II-74 | III-1 |
| T-636 | I-11 | II-75 | III-1 |
| T-637 | I-11 | II-76 | III-1 |
| T-638 | I-11 | II-77 | III-1 |
| T-639 | I-12 | II-56 | III-1 |
| T-640 | I-12 | II-57 | III-1 |
| T-641 | I-12 | II-58 | III-1 |
| T-642 | I-12 | II-59 | III-1 |
| T-643 | I-12 | II-60 | III-1 |
| T-644 | I-12 | II-61 | III-1 |
| T-645 | I-12 | II-62 | III-1 |
| T-646 | I-12 | II-63 | III-1 |
| T-647 | I-12 | II-64 | III-1 |
| T-648 | I-12 | II-65 | III-1 |
| T-649 | I-12 | II-66 | III-1 |
| T-650 | I-12 | II-67 | III-1 |
| T-651 | I-12 | II-68 | III-1 |
| T-652 | I-12 | II-69 | III-1 |
| T-653 | I-12 | II-70 | III-1 |
| T-654 | I-12 | II-71 | III-1 |
| T-655 | I-12 | II-72 | III-1 |
| T-656 | I-12 | II-73 | III-1 |
| T-657 | I-12 | II-74 | III-1 |
| T-658 | I-12 | II-75 | III-1 |
| T-659 | I-12 | II-76 | III-1 |
| T-660 | I-12 | II-77 | III-1 |

Table B2: Mixtures as defined in each row of Table B1 wherein component 3 (Co. 3) is compound III-2 instead of III-1.

Table B3: Mixtures as defined in each row of Table B1 wherein component 3 (Co. 3) is compound III-4 instead of III-1.

Table B4: Mixtures as defined in each row of Table B1 wherein component 3 (Co. 3) is compound III-4 instead of III-1.

Table B5: Mixtures as defined in each row of Table B1 wherein component 3 (Co. 3) is compound III-5 instead of III-1.

Table B6: Mixtures as defined in each row of Table B1 wherein component 3 (Co. 3) is compound III-6 instead of III-1.

Table B7: Mixtures as defined in each row of Table B1 wherein component 3 (Co. 3) is compound III-7 instead of III-1.

Table B8: Mixtures as defined in each row of Table B1 wherein component 3 (Co. 3) is compound III-8 instead of III-1.

Table B9: Mixtures as defined in each row of Table B1 wherein component 3 (Co. 3) is compound III-9 instead of III-1.

Table B10: Mixtures as defined in each row of Table B1 wherein component 3 (Co. 3) is compound III-10 instead of III-1.

Table B11: Mixtures as defined in each row of Table B1 wherein component 3 (Co. 3) is compound III-11 instead of III-1.

Table B12: Mixtures as defined in each row of Table B1 wherein component 3 (Co. 3) is compound III-12 instead of III-1.

Table B13: Mixtures as defined in each row of Table B1 wherein component 3 (Co. 3) is compound III-13 instead of III-1.

Table B14: Mixtures as defined in each row of Table B1 wherein component 3 (Co. 3) is compound III-14 instead of III-1.

Table B15: Mixtures as defined in each row of Table B1 wherein component 3 (Co. 3) is compound III-15 instead of III-1.

Table B16: Mixtures as defined in each row of Table B1 wherein component 3 (Co. 3) is compound III-16 instead of III-1.

Table B17: Mixtures as defined in each row of Table B1 wherein component 3 (Co. 3) is compound III-17 instead of III-1.

Table B18: Mixtures as defined in each row of Table B1 wherein component 3 (Co. 3) is compound III-18 instead of III-1.

Accordingly, the present invention furthermore relates to the mixtures as defined in Table X, where a row corresponds in each case to a fungicidal composition comprising as component 1) one of the compounds I as defined and numbered above (Co. 1), and as component 2) one of the compounds II as defined and numbered above (Co. 2), and as component 3) the respective compound III as defined in table B (Co. 3) stated in the row in question. Preferably, the compositions described comprise the active substances in synergistically effective amounts.

TABLE X

Ternary mixtures X-1 to X-648 comprising one compound I as defined and numbered above as component 1) (Co. 1) and one compound II as defined and numbered above as component 2) (Co. 2) and one compound III as defined and numbered in Table B as component 3) (Co. 3).

| Mixt. | Co. 1 | Co. 2 | Co. 3 |
|---|---|---|---|
| X-1 | I-2 | II-1 | III-1 |
| X-2 | I-5 | II-1 | III-1 |
| X-3 | I-6 | II-1 | III-1 |

TABLE X-continued

Ternary mixtures X-1 to X-648 comprising one compound I as defined and numbered above as component 1) (Co. 1) and one compound II as defined and numbered above as component 2) (Co. 2) and one compound III as defined and numbered in Table B as component 3) (Co. 3).

| Mixt. | Co. 1 | Co. 2 | Co. 3 |
|---|---|---|---|
| X-4 | I-57 | II-1 | III-1 |
| X-5 | I-2 | II-3 | III-1 |
| X-6 | I-5 | II-3 | III-1 |
| X-7 | I-6 | II-3 | III-1 |
| X-8 | I-57 | II-3 | III-1 |
| X-9 | I-2 | II-13 | III-1 |
| X-10 | I-5 | II-13 | III-1 |
| X-11 | I-6 | II-13 | III-1 |
| X-12 | I-57 | II-13 | III-1 |
| X-13 | I-2 | II-1 | III-2 |
| X-14 | I-5 | II-1 | III-2 |
| X-15 | I-6 | II-1 | III-2 |
| X-16 | I-57 | II-1 | III-2 |
| X-17 | I-2 | II-3 | III-2 |
| X-18 | I-5 | II-3 | III-2 |
| X-19 | I-6 | II-3 | III-2 |
| X-20 | I-57 | II-3 | III-2 |
| X-21 | I-2 | II-13 | III-2 |
| X-22 | I-5 | II-13 | III-2 |
| X-23 | I-6 | II-13 | III-2 |
| X-24 | I-57 | II-13 | III-2 |
| X-25 | I-2 | II-1 | III-3 |
| X-26 | I-5 | II-1 | III-3 |
| X-27 | I-6 | II-1 | III-3 |
| X-28 | I-57 | II-1 | III-3 |
| X-29 | I-2 | II-3 | III-3 |
| X-30 | I-5 | II-3 | III-3 |
| X-31 | I-6 | II-3 | III-3 |
| X-32 | I-57 | II-3 | III-3 |
| X-33 | I-2 | II-13 | III-3 |
| X-34 | I-5 | II-13 | III-3 |
| X-35 | I-6 | II-13 | III-3 |
| X-36 | I-57 | II-13 | III-3 |
| X-37 | I-2 | II-1 | III-4 |
| X-38 | I-5 | II-1 | III-4 |
| X-39 | I-6 | II-1 | III-4 |
| X-40 | I-57 | II-1 | III-4 |
| X-41 | I-2 | II-3 | III-4 |
| X-42 | I-5 | II-3 | III-4 |
| X-43 | I-6 | II-3 | III-4 |
| X-44 | I-57 | II-3 | III-4 |
| X-45 | I-2 | II-13 | III-4 |
| X-46 | I-5 | II-13 | III-4 |
| X-47 | I-6 | II-13 | III-4 |
| X-48 | I-57 | II-13 | III-4 |
| X-49 | I-2 | II-1 | III-5 |
| X-50 | I-5 | II-1 | III-5 |
| X-51 | I-6 | II-1 | III-5 |
| X-52 | I-57 | II-1 | III-5 |
| X-53 | I-2 | II-3 | III-5 |
| X-54 | I-5 | II-3 | III-5 |
| X-55 | I-6 | II-3 | III-5 |
| X-56 | I-57 | II-3 | III-5 |
| X-57 | I-2 | II-13 | III-5 |
| X-58 | I-5 | II-13 | III-5 |
| X-59 | I-6 | II-13 | III-5 |
| X-60 | I-57 | II-13 | III-5 |
| X-61 | I-2 | II-1 | III-6 |
| X-62 | I-5 | II-1 | III-6 |
| X-63 | I-6 | II-1 | III-6 |
| X-64 | I-57 | II-1 | III-6 |
| X-65 | I-2 | II-3 | III-6 |
| X-66 | I-5 | II-3 | III-6 |
| X-67 | I-6 | II-3 | III-6 |
| X-68 | I-57 | II-3 | III-6 |
| X-69 | I-2 | II-13 | III-6 |
| X-70 | I-5 | II-13 | III-6 |
| X-71 | I-6 | II-13 | III-6 |
| X-72 | I-57 | II-13 | III-6 |
| X-73 | I-2 | II-1 | III-7 |
| X-74 | I-5 | II-1 | III-7 |
| X-75 | I-6 | II-1 | III-7 |
| X-76 | I-57 | II-1 | III-7 |
| X-77 | I-2 | II-3 | III-7 |
| X-78 | I-5 | II-3 | III-7 |
| X-79 | I-6 | II-3 | III-7 |
| X-80 | I-57 | II-3 | III-7 |
| X-81 | I-2 | II-13 | III-7 |
| X-82 | I-5 | II-13 | III-7 |
| X-83 | I-6 | II-13 | III-7 |
| X-84 | I-57 | II-13 | III-7 |
| X-85 | I-2 | II-1 | III-8 |
| X-86 | I-5 | II-1 | III-8 |
| X-87 | I-6 | II-1 | III-8 |
| X-88 | I-57 | II-1 | III-8 |
| X-89 | I-2 | II-3 | III-8 |
| X-90 | I-5 | II-3 | III-8 |
| X-91 | I-6 | II-3 | III-8 |
| X-92 | I-57 | II-3 | III-8 |
| X-93 | I-2 | II-13 | III-8 |
| X-94 | I-5 | II-13 | III-8 |
| X-95 | I-6 | II-13 | III-8 |
| X-96 | I-57 | II-13 | III-8 |
| X-97 | I-2 | II-1 | III-9 |
| X-98 | I-5 | II-1 | III-9 |
| X-99 | I-6 | II-1 | III-9 |
| X-100 | I-57 | II-1 | III-9 |
| X-101 | I-2 | II-3 | III-9 |
| X-102 | I-5 | II-3 | III-9 |
| X-103 | I-6 | II-3 | III-9 |
| X-104 | I-57 | II-3 | III-9 |
| X-105 | I-2 | II-13 | III-9 |
| X-106 | I-5 | II-13 | III-9 |
| X-107 | I-6 | II-13 | III-9 |
| X-108 | I-57 | II-13 | III-9 |
| X-109 | I-2 | II-1 | III-10 |
| X-110 | I-5 | II-1 | III-10 |
| X-111 | II-6 | II-1 | III-10 |
| X-112 | I-57 | II-1 | III-10 |
| X-113 | I-2 | II-3 | III-10 |
| X-114 | I-5 | II-3 | III-10 |
| X-115 | I-6 | II-3 | III-10 |
| X-116 | I-57 | II-3 | III-10 |
| X-117 | I-2 | II-13 | III-10 |
| X-118 | I-5 | II-13 | III-10 |
| X-119 | I-6 | II-13 | III-10 |
| X-120 | I-57 | II-13 | III-10 |
| X-121 | I-2 | II-1 | III-11 |
| X-122 | I-5 | II-1 | III-11 |
| X-123 | I-6 | II-1 | III-11 |
| X-124 | I-57 | II-1 | III-11 |
| X-125 | I-2 | II-3 | III-11 |
| X-126 | I-5 | II-3 | III-11 |
| X-127 | I-6 | II-3 | III-11 |
| X-128 | I-57 | II-3 | III-11 |
| X-129 | I-2 | II-13 | III-11 |
| X-130 | I-5 | II-13 | III-11 |
| X-131 | I-6 | II-13 | III-11 |
| X-132 | I-57 | II-13 | III-11 |
| X-133 | I-2 | II-1 | III-12 |
| X-134 | I-5 | II-1 | III-12 |
| X-135 | I-6 | II-1 | III-12 |
| X-136 | I-57 | II-1 | III-12 |
| X-137 | I-2 | II-3 | III-12 |
| X-138 | I-5 | II-3 | III-12 |
| X-139 | I-6 | II-3 | III-12 |
| X-140 | I-57 | II-3 | III-12 |
| X-141 | I-2 | II-13 | III-12 |
| X-142 | I-5 | II-13 | III-12 |
| X-143 | I-6 | II-13 | III-12 |
| X-144 | I-57 | II-13 | III-12 |
| X-145 | I-2 | II-1 | III-13 |
| X-146 | I-5 | II-1 | III-13 |
| X-147 | I-6 | II-1 | III-13 |
| X-148 | I-57 | II-1 | III-13 |
| X-149 | I-2 | II-3 | III-13 |

TABLE X-continued

Ternary mixtures X-1 to X-648 comprising one compound I as defined and numbered above as component 1) (Co. 1) and one compound II as defined and numbered above as component 2) (Co. 2) and one compound III as defined and numbered in Table B as component 3) (Co. 3).

| Mixt. | Co. 1 | Co. 2 | Co. 3 |
|---|---|---|---|
| X-150 | I-5 | II-3 | III-13 |
| X-151 | I-6 | II-3 | III-13 |
| X-152 | I-57 | II-3 | III-13 |
| X-153 | I-2 | II-13 | III-13 |
| X-154 | I-5 | II-13 | III-13 |
| X-155 | I-6 | II-13 | III-13 |
| X-156 | I-57 | II-13 | III-13 |
| X-157 | I-2 | II-1 | III-14 |
| X-158 | I-5 | II-1 | III-14 |
| X-159 | I-6 | II-1 | III-14 |
| X-160 | I-57 | II-1 | III-14 |
| X-161 | I-2 | II-3 | III-14 |
| X-162 | I-5 | II-3 | III-14 |
| X-163 | I-6 | II-3 | III-14 |
| X-164 | I-57 | II-3 | III-14 |
| X-165 | I-2 | II-13 | III-14 |
| X-166 | I-5 | II-13 | III-14 |
| X-167 | I-6 | II-13 | III-14 |
| X-168 | I-57 | II-13 | III-14 |
| X-169 | I-2 | II-1 | III-15 |
| X-170 | I-5 | II-1 | III-15 |
| X-171 | I-6 | II-1 | III-15 |
| X-172 | I-57 | II-1 | III-15 |
| X-173 | I-2 | II-3 | III-15 |
| X-174 | I-5 | II-3 | III-15 |
| X-175 | I-6 | II-3 | III-15 |
| X-176 | I-57 | II-3 | III-15 |
| X-177 | I-2 | II-13 | III-15 |
| X-178 | I-5 | II-13 | III-15 |
| X-179 | I-6 | II-13 | III-15 |
| X-180 | I-57 | II-13 | III-15 |
| X-181 | I-2 | II-1 | III-16 |
| X-182 | I-5 | II-1 | III-16 |
| X-183 | I-6 | II-1 | III-16 |
| X-184 | I-57 | II-1 | III-16 |
| X-185 | I-2 | II-3 | III-16 |
| X-186 | I-5 | II-3 | III-16 |
| X-187 | I-6 | II-3 | III-16 |
| X-188 | I-57 | II-3 | III-16 |
| X-189 | I-2 | II-13 | III-16 |
| X-190 | I-5 | II-13 | III-16 |
| X-191 | I-6 | II-13 | III-16 |
| X-192 | I-57 | II-13 | III-16 |
| X-193 | I-2 | II-1 | III-17 |
| X-194 | I-5 | II-1 | III-17 |
| X-195 | I-6 | II-1 | III-17 |
| X-196 | I-57 | II-1 | III-17 |
| X-197 | I-2 | II-3 | III-17 |
| X-198 | I-5 | II-3 | III-17 |
| X-199 | I-6 | II-3 | III-17 |
| X-200 | I-57 | II-3 | III-17 |
| X-201 | I-2 | II-13 | III-17 |
| X-202 | I-5 | II-13 | III-17 |
| X-203 | I-6 | II-13 | III-17 |
| X-204 | I-57 | II-13 | III-17 |
| X-205 | I-2 | II-1 | III-18 |
| X-206 | I-5 | II-1 | III-18 |
| X-207 | I-6 | II-1 | III-18 |
| X-208 | I-57 | II-1 | III-18 |
| X-209 | I-2 | II-3 | III-18 |
| X-210 | I-5 | II-3 | III-18 |
| X-211 | I-6 | II-3 | III-18 |
| X-212 | I-57 | II-3 | III-18 |
| X-213 | I-2 | II-13 | III-18 |
| X-214 | I-5 | II-13 | III-18 |
| X-215 | I-6 | II-13 | III-18 |
| X-216 | I-57 | II-13 | III-18 |
| X-217 | I-2 | II-1 | III-19 |
| X-218 | I-5 | II-1 | III-19 |
| X-219 | I-6 | II-1 | III-19 |
| X-220 | I-57 | II-1 | III-19 |
| X-221 | I-2 | II-3 | III-19 |
| X-222 | I-5 | II-3 | III-19 |
| X-223 | I-6 | II-3 | III-19 |
| X-224 | I-57 | II-3 | III-19 |
| X-225 | I-2 | II-13 | III-19 |
| X-226 | I-5 | II-13 | III-19 |
| X-227 | I-6 | II-13 | III-19 |
| X-228 | I-57 | II-13 | III-19 |
| X-229 | I-2 | II-1 | III-20 |
| X-230 | I-5 | II-1 | III-20 |
| X-231 | I-6 | II-1 | III-20 |
| X-232 | I-57 | II-1 | III-20 |
| X-233 | I-2 | II-3 | III-20 |
| X-234 | I-5 | II-3 | III-20 |
| X-235 | I-6 | II-3 | III-20 |
| X-236 | I-57 | II-3 | III-20 |
| X-237 | I-2 | II-13 | III-20 |
| X-238 | I-5 | II-13 | III-20 |
| X-239 | I-6 | II-13 | III-20 |
| X-240 | I-57 | II-13 | III-20 |
| X-241 | I-2 | II-1 | III-21 |
| X-242 | I-5 | II-1 | III-21 |
| X-243 | I-6 | II-1 | III-21 |
| X-244 | I-57 | II-1 | III-21 |
| X-245 | I-2 | II-3 | III-21 |
| X-246 | I-5 | II-3 | III-21 |
| X-247 | I-6 | II-3 | III-21 |
| X-248 | I-57 | II-3 | III-21 |
| X-249 | I-2 | II-13 | III-21 |
| X-250 | I-5 | II-13 | III-21 |
| X-251 | I-6 | II-13 | III-21 |
| X-252 | I-57 | II-13 | III-21 |
| X-253 | I-2 | II-1 | III-22 |
| X-254 | I-5 | II-1 | III-22 |
| X-255 | I-6 | II-1 | III-22 |
| X-256 | I-57 | II-1 | III-22 |
| X-257 | I-2 | II-3 | III-22 |
| X-258 | I-5 | II-3 | III-22 |
| X-259 | I-6 | II-3 | III-22 |
| X-260 | I-57 | II-3 | III-22 |
| X-261 | I-2 | II-13 | III-22 |
| X-262 | I-5 | II-13 | III-22 |
| X-263 | I-6 | II-13 | III-22 |
| X-264 | I-57 | II-13 | III-22 |
| X-265 | I-2 | II-1 | III-23 |
| X-266 | I-5 | II-1 | III-23 |
| X-267 | I-6 | II-1 | III-23 |
| X-268 | I-57 | II-1 | III-23 |
| X-269 | I-2 | II-3 | III-23 |
| X-270 | I-5 | II-3 | III-23 |
| X-271 | I-6 | II-3 | III-23 |
| X-272 | I-57 | II-3 | III-23 |
| X-273 | I-2 | II-13 | III-23 |
| X-274 | I-5 | II-13 | III-23 |
| X-275 | I-6 | II-13 | III-23 |
| X-276 | I-57 | II-13 | III-23 |
| X-277 | I-2 | II-1 | III-24 |
| X-278 | I-5 | II-1 | III-24 |
| X-279 | I-6 | II-1 | III-24 |
| X-280 | I-57 | II-1 | III-24 |
| X-281 | I-2 | II-3 | III-24 |
| X-282 | I-5 | II-3 | III-24 |
| X-283 | I-6 | II-3 | III-24 |
| X-284 | I-57 | II-3 | III-24 |
| X-285 | I-2 | II-13 | III-24 |
| X-286 | I-5 | II-13 | III-24 |
| X-287 | I-6 | II-13 | III-24 |
| X-288 | I-57 | II-13 | III-24 |
| X-289 | I-2 | II-1 | III-25 |
| X-290 | I-5 | II-1 | III-25 |
| X-291 | I-6 | II-1 | III-25 |
| X-292 | I-57 | II-1 | III-25 |
| X-293 | I-2 | II-3 | III-25 |
| X-294 | I-5 | II-3 | III-25 |
| X-295 | I-6 | II-3 | III-25 |

TABLE X-continued

Ternary mixtures X-1 to X-648 comprising one compound I as defined and numbered above as component 1) (Co. 1) and one compound II as defined and numbered above as component 2) (Co. 2) and one compound III as defined and numbered in Table B as component 3) (Co. 3).

| Mixt. | Co. 1 | Co. 2 | Co. 3 |
|---|---|---|---|
| X-296 | I-57 | II-3 | III-25 |
| X-297 | I-2 | II-13 | III-25 |
| X-298 | I-5 | II-13 | III-25 |
| X-299 | I-6 | II-13 | III-25 |
| X-300 | I-57 | II-13 | III-25 |
| X-301 | I-2 | II-1 | III-26 |
| X-302 | I-5 | II-1 | III-26 |
| X-303 | I-6 | II-1 | III-26 |
| X-304 | I-57 | II-1 | III-26 |
| X-305 | I-2 | II-3 | III-26 |
| X-306 | I-5 | II-3 | III-26 |
| X-307 | I-6 | II-3 | III-26 |
| X-308 | I-57 | II-3 | III-26 |
| X-309 | I-2 | II-13 | III-26 |
| X-310 | I-5 | II-13 | III-26 |
| X-311 | I-6 | II-13 | III-26 |
| X-312 | I-57 | II-13 | III-26 |
| X-313 | I-2 | II-1 | III-27 |
| X-314 | I-5 | II-1 | III-27 |
| X-315 | I-6 | II-1 | III-27 |
| X-316 | I-57 | II-1 | III-27 |
| X-317 | I-2 | II-3 | III-27 |
| X-318 | I-5 | II-3 | III-27 |
| X-319 | I-6 | II-3 | III-27 |
| X-320 | I-57 | II-3 | III-27 |
| X-321 | I-2 | II-13 | III-27 |
| X-322 | I-5 | II-13 | III-27 |
| X-323 | I-6 | II-13 | III-27 |
| X-324 | I-57 | II-13 | III-27 |
| X-325 | I-2 | II-1 | III-28 |
| X-326 | I-5 | II-1 | III-28 |
| X-327 | I-6 | II-1 | III-28 |
| X-328 | I-57 | II-1 | III-28 |
| X-329 | I-2 | II-3 | III-28 |
| X-330 | I-5 | II-3 | III-28 |
| X-331 | I-6 | II-3 | III-28 |
| X-332 | I-57 | II-3 | III-28 |
| X-333 | I-2 | II-13 | III-28 |
| X-334 | I-5 | II-13 | III-28 |
| X-335 | I-6 | II-13 | III-28 |
| X-336 | I-57 | II-13 | III-28 |
| X-337 | I-2 | II-1 | III-29 |
| X-338 | I-5 | II-1 | III-29 |
| X-339 | I-6 | II-1 | III-29 |
| X-340 | I-57 | II-1 | III-29 |
| X-341 | I-2 | II-3 | III-29 |
| X-342 | I-5 | II-3 | III-29 |
| X-343 | I-6 | II-3 | III-29 |
| X-344 | I-57 | II-3 | III-29 |
| X-345 | I-2 | II-13 | III-29 |
| X-346 | I-5 | II-13 | III-29 |
| X-347 | I-6 | II-13 | III-29 |
| X-348 | I-57 | II-13 | III-29 |
| X-349 | I-2 | II-1 | III-30 |
| X-350 | I-5 | II-1 | III-30 |
| X-351 | I-6 | II-1 | III-30 |
| X-352 | I-57 | II-1 | III-30 |
| X-353 | I-2 | II-3 | III-30 |
| X-354 | I-5 | II-3 | III-30 |
| X-355 | I-6 | II-3 | III-30 |
| X-356 | I-57 | II-3 | III-30 |
| X-357 | I-2 | II-13 | III-30 |
| X-358 | I-5 | II-13 | III-30 |
| X-359 | I-6 | II-13 | III-30 |
| X-360 | I-57 | II-13 | III-30 |
| X-361 | I-2 | II-1 | III-31 |
| X-362 | I-5 | II-1 | III-31 |
| X-363 | I-6 | II-1 | III-31 |
| X-364 | I-57 | II-1 | III-31 |
| X-365 | I-2 | II-3 | III-31 |
| X-366 | I-5 | II-3 | III-31 |
| X-367 | I-6 | II-3 | III-31 |
| X-368 | I-57 | II-3 | III-31 |
| X-369 | I-2 | II-13 | III-31 |
| X-370 | I-5 | II-13 | III-31 |
| X-371 | I-6 | II-13 | III-31 |
| X-372 | I-57 | II-13 | III-31 |
| X-373 | I-2 | II-1 | III-32 |
| X-374 | I-5 | II-1 | III-32 |
| X-375 | I-6 | II-1 | III-32 |
| X-376 | I-57 | II-1 | III-32 |
| X-377 | I-2 | II-3 | III-32 |
| X-378 | I-5 | II-3 | III-32 |
| X-379 | I-6 | II-3 | III-32 |
| X-380 | I-57 | II-3 | III-32 |
| X-381 | I-2 | II-13 | III-32 |
| X-382 | I-5 | II-13 | III-32 |
| X-383 | I-6 | II-13 | III-32 |
| X-384 | I-57 | II-13 | III-32 |
| X-385 | I-2 | II-1 | III-33 |
| X-386 | I-5 | II-1 | III-33 |
| X-387 | I-6 | II-1 | III-33 |
| X-388 | I-57 | II-1 | III-33 |
| X-389 | I-2 | II-3 | III-33 |
| X-390 | I-5 | II-3 | III-33 |
| X-391 | I-6 | II-3 | III-33 |
| X-392 | I-57 | II-3 | III-33 |
| X-393 | I-2 | II-13 | III-33 |
| X-394 | I-5 | II-13 | III-33 |
| X-395 | I-6 | II-13 | III-33 |
| X-396 | I-57 | II-13 | III-33 |
| X-397 | I-2 | II-1 | III-34 |
| X-398 | I-5 | II-1 | III-34 |
| X-399 | I-6 | II-1 | III-34 |
| X-400 | I-57 | II-1 | III-34 |
| X-401 | I-2 | II-3 | III-34 |
| X-402 | I-5 | II-3 | III-34 |
| X-403 | I-6 | II-3 | III-34 |
| X-404 | I-57 | II-3 | III-34 |
| X-405 | I-2 | II-13 | III-34 |
| X-406 | I-5 | II-13 | III-34 |
| X-407 | I-6 | II-13 | III-34 |
| X-408 | I-57 | II-13 | III-34 |
| X-409 | I-2 | II-1 | III-35 |
| X-410 | I-5 | II-1 | III-35 |
| X-411 | I-6 | II-1 | III-35 |
| X-412 | I-57 | II-1 | III-35 |
| X-413 | I-2 | II-3 | III-35 |
| X-414 | I-5 | II-3 | III-35 |
| X-415 | I-6 | II-3 | III-35 |
| X-416 | I-57 | II-3 | III-35 |
| X-417 | I-2 | II-13 | III-35 |
| X-418 | I-5 | II-13 | III-35 |
| X-419 | I-6 | II-13 | III-35 |
| X-420 | I-57 | II-13 | III-35 |
| X-421 | I-2 | II-1 | III-36 |
| X-422 | I-5 | II-1 | III-36 |
| X-423 | I-6 | II-1 | III-36 |
| X-424 | I-57 | II-1 | III-36 |
| X-425 | I-2 | II-3 | III-36 |
| X-426 | I-5 | II-3 | III-36 |
| X-427 | I-6 | II-3 | III-36 |
| X-428 | I-57 | II-3 | III-36 |
| X-429 | I-2 | II-13 | III-36 |
| X-430 | I-5 | II-13 | III-36 |
| X-431 | I-6 | II-13 | III-36 |
| X-432 | I-57 | II-13 | III-36 |
| X-433 | I-2 | II-1 | III-37 |
| X-434 | I-5 | II-1 | III-37 |
| X-435 | I-6 | II-1 | III-37 |
| X-436 | I-57 | II-1 | III-37 |
| X-437 | I-2 | II-3 | III-37 |
| X-438 | I-5 | II-3 | III-37 |
| X-439 | I-6 | II-3 | III-37 |
| X-440 | I-57 | II-3 | III-37 |
| X-441 | I-2 | II-13 | III-37 |

TABLE X-continued

Ternary mixtures X-1 to X-648 comprising one compound I as defined and numbered above as component 1) (Co. 1) and one compound II as defined and numbered above as component 2) (Co. 2) and one compound III as defined and numbered in Table B as component 3) (Co. 3).

| Mixt. | Co. 1 | Co. 2 | Co. 3 |
|---|---|---|---|
| X-442 | I-5 | II-13 | III-37 |
| X-443 | I-6 | II-13 | III-37 |
| X-444 | I-57 | II-13 | III-37 |
| X-445 | I-2 | II-1 | III-38 |
| X-446 | I-5 | II-1 | III-38 |
| X-447 | I-6 | II-1 | III-38 |
| X-448 | I-57 | II-1 | III-38 |
| X-449 | I-2 | II-3 | III-38 |
| X-450 | I-5 | II-3 | III-38 |
| X-451 | I-6 | II-3 | III-38 |
| X-452 | I-57 | II-3 | III-38 |
| X-453 | I-2 | II-13 | III-38 |
| X-454 | I-5 | II-13 | III-38 |
| X-455 | I-6 | II-13 | III-38 |
| X-456 | I-57 | II-13 | III-38 |
| X-457 | I-2 | II-1 | III-39 |
| X-458 | I-5 | II-1 | III-39 |
| X-459 | I-6 | II-1 | III-39 |
| X-460 | I-57 | II-1 | III-39 |
| X-461 | I-2 | II-3 | III-39 |
| X-462 | I-5 | II-3 | III-39 |
| X-463 | I-6 | II-3 | III-39 |
| X-464 | I-57 | II-3 | III-39 |
| X-465 | I-2 | II-13 | III-39 |
| X-466 | I-5 | II-13 | III-39 |
| X-467 | I-6 | II-13 | III-39 |
| X-468 | I-57 | II-13 | III-39 |
| X-469 | I-2 | II-1 | III-40 |
| X-470 | I-5 | II-1 | III-40 |
| X-471 | I-6 | II-1 | III-40 |
| X-472 | I-57 | II-1 | III-40 |
| X-473 | I-2 | II-3 | III-40 |
| X-474 | I-5 | II-3 | III-40 |
| X-475 | I-6 | II-3 | III-40 |
| X-476 | I-57 | II-3 | III-40 |
| X-477 | I-2 | II-13 | III-40 |
| X-478 | I-5 | II-13 | III-40 |
| X-479 | I-6 | II-13 | III-40 |
| X-480 | I-57 | II-13 | III-40 |
| X-481 | I-2 | II-1 | III-41 |
| X-482 | I-5 | II-1 | III-41 |
| X-483 | I-6 | II-1 | III-41 |
| X-484 | I-57 | II-1 | III-41 |
| X-485 | I-2 | II-3 | III-41 |
| X-486 | I-5 | II-3 | III-41 |
| X-487 | I-6 | II-3 | III-41 |
| X-488 | I-57 | II-3 | III-41 |
| X-489 | I-2 | II-13 | III-41 |
| X-490 | I-5 | II-13 | III-41 |
| X-491 | I-6 | II-13 | III-41 |
| X-492 | I-57 | II-13 | III-41 |
| X-493 | I-2 | II-1 | III-42 |
| X-494 | I-5 | II-1 | III-42 |
| X-495 | I-6 | II-1 | III-42 |
| X-496 | I-57 | II-1 | III-42 |
| X-497 | I-2 | II-3 | III-42 |
| X-498 | I-5 | II-3 | III-42 |
| X-499 | I-6 | II-3 | III-42 |
| X-500 | I-57 | II-3 | III-42 |
| X-501 | I-2 | II-13 | III-42 |
| X-502 | I-5 | II-13 | III-42 |
| X-503 | I-6 | II-13 | III-42 |
| X-504 | I-57 | II-13 | III-42 |
| X-505 | I-2 | II-1 | III-43 |
| X-506 | I-5 | II-1 | III-43 |
| X-507 | I-6 | II-1 | III-43 |
| X-508 | I-57 | II-1 | III-43 |
| X-509 | I-2 | II-3 | III-43 |
| X-510 | I-5 | II-3 | III-43 |
| X-511 | I-6 | II-3 | III-43 |
| X-512 | I-57 | II-3 | III-43 |
| X-513 | I-2 | II-13 | III-43 |
| X-514 | I-5 | II-13 | III-43 |
| X-515 | I-6 | II-13 | III-43 |
| X-516 | I-57 | II-13 | III-43 |
| X-517 | I-2 | II-1 | III-44 |
| X-518 | I-5 | II-1 | III-44 |
| X-519 | I-6 | II-1 | III-44 |
| X-520 | I-57 | II-1 | III-44 |
| X-521 | I-2 | II-3 | III-44 |
| X-522 | I-5 | II-3 | III-44 |
| X-523 | I-6 | II-3 | III-44 |
| X-524 | I-57 | II-3 | III-44 |
| X-525 | I-2 | II-13 | III-44 |
| X-526 | I-5 | II-13 | III-44 |
| X-527 | I-6 | II-13 | III-44 |
| X-528 | I-57 | II-13 | III-44 |
| X-529 | I-2 | II-1 | III-45 |
| X-530 | I-5 | II-1 | III-45 |
| X-531 | I-6 | II-1 | III-45 |
| X-532 | I-57 | II-1 | III-45 |
| X-533 | I-2 | II-3 | III-45 |
| X-534 | I-5 | II-3 | III-45 |
| X-535 | I-6 | II-3 | III-45 |
| X-536 | I-57 | II-3 | III-45 |
| X-537 | I-2 | II-13 | III-45 |
| X-538 | I-5 | II-13 | III-45 |
| X-539 | I-6 | II-13 | III-45 |
| X-540 | I-57 | II-13 | III-45 |
| X-541 | I-2 | II-1 | III-46 |
| X-542 | I-5 | II-1 | III-46 |
| X-543 | I-6 | II-1 | III-46 |
| X-544 | I-57 | II-1 | III-46 |
| X-545 | I-2 | II-3 | III-46 |
| X-546 | I-5 | II-3 | III-46 |
| X-547 | I-6 | II-3 | III-46 |
| X-548 | I-57 | II-3 | III-46 |
| X-549 | I-2 | II-13 | III-46 |
| X-550 | I-5 | II-13 | III-46 |
| X-551 | I-6 | II-13 | III-46 |
| X-552 | I-57 | II-13 | III-46 |
| X-553 | I-2 | II-1 | III-47 |
| X-554 | I-5 | II-1 | III-47 |
| X-555 | I-6 | II-1 | III-47 |
| X-556 | I-57 | II-1 | III-47 |
| X-557 | I-2 | II-3 | III-47 |
| X-558 | I-5 | II-3 | III-47 |
| X-559 | I-6 | II-3 | III-47 |
| X-560 | I-57 | II-3 | III-47 |
| X-561 | I-2 | II-13 | III-47 |
| X-562 | I-5 | II-13 | III-47 |
| X-563 | I-6 | II-13 | III-47 |
| X-564 | I-57 | II-13 | III-47 |
| X-565 | I-2 | II-1 | III-48 |
| X-566 | I-5 | II-1 | III-48 |
| X-567 | I-6 | II-1 | III-48 |
| X-568 | I-57 | II-1 | III-48 |
| X-569 | I-2 | II-3 | III-48 |
| X-570 | I-5 | II-3 | III-48 |
| X-571 | I-6 | II-3 | III-48 |
| X-572 | I-57 | II-3 | III-48 |
| X-573 | I-2 | II-13 | III-48 |
| X-574 | I-5 | II-13 | III-48 |
| X-575 | I-6 | II-13 | III-48 |
| X-576 | I-57 | II-13 | III-48 |
| X-577 | I-2 | II-1 | III-49 |
| X-578 | I-5 | II-1 | III-49 |
| X-579 | I-6 | II-1 | III-49 |
| X-580 | I-57 | II-1 | III-49 |
| X-581 | I-2 | II-3 | III-49 |
| X-582 | I-5 | II-3 | III-49 |
| X-583 | I-6 | II-3 | III-49 |
| X-584 | I-57 | II-3 | III-49 |
| X-585 | I-2 | II-13 | III-49 |
| X-586 | I-5 | II-13 | III-49 |
| X-587 | I-6 | II-13 | III-49 |

TABLE X-continued

Ternary mixtures X-1 to X-648 comprising one compound I as defined and numbered above as component 1) (Co. 1) and one compound II as defined and numbered above as component 2) (Co. 2) and one compound III as defined and numbered in Table B as component 3) (Co. 3).

| Mixt. | Co. 1 | Co. 2 | Co. 3 |
|---|---|---|---|
| X-588 | I-57 | II-13 | III-49 |
| X-589 | I-2 | II-1 | III-50 |
| X-590 | I-5 | II-1 | III-50 |
| X-591 | I-6 | II-1 | III-50 |
| X-592 | I-57 | II-1 | III-50 |
| X-593 | I-2 | II-3 | III-50 |
| X-594 | I-5 | II-3 | III-50 |
| X-595 | I-6 | II-3 | III-50 |
| X-596 | I-57 | II-3 | III-50 |
| X-597 | I-2 | II-13 | III-50 |
| X-598 | I-5 | II-13 | III-50 |
| X-599 | I-6 | II-13 | III-50 |
| X-600 | I-57 | II-13 | III-50 |
| X-601 | I-2 | II-1 | III-51 |
| X-602 | I-5 | II-1 | III-51 |
| X-603 | I-6 | II-1 | III-51 |
| X-604 | I-57 | II-1 | III-51 |
| X-605 | I-2 | II-3 | III-51 |
| X-606 | I-5 | II-3 | III-51 |
| X-607 | I-6 | II-3 | III-51 |
| X-608 | I-57 | II-3 | III-51 |
| X-609 | I-2 | II-13 | III-51 |
| X-610 | I-5 | II-13 | III-51 |
| X-611 | I-6 | II-13 | III-51 |
| X-612 | I-57 | II-13 | III-51 |
| X-613 | I-2 | II-1 | III-52 |
| X-614 | I-5 | II-1 | III-52 |
| X-615 | I-6 | II-1 | III-52 |
| X-616 | I-57 | II-1 | III-52 |
| X-617 | I-2 | II-3 | III-52 |
| X-618 | I-5 | II-3 | III-52 |
| X-619 | I-6 | II-3 | III-52 |
| X-620 | I-57 | II-3 | III-52 |
| X-621 | I-2 | II-13 | III-52 |
| X-622 | I-5 | II-13 | III-52 |
| X-623 | I-6 | II-13 | III-52 |
| X-624 | I-57 | II-13 | III-52 |
| X-625 | I-2 | II-1 | III-53 |
| X-626 | I-5 | II-1 | III-53 |
| X-627 | I-6 | II-1 | III-53 |
| X-628 | I-57 | II-1 | III-53 |
| X-629 | I-2 | II-3 | III-53 |
| X-630 | I-5 | II-3 | III-53 |
| X-631 | I-6 | II-3 | III-53 |
| X-632 | I-57 | II-3 | III-53 |
| X-633 | I-2 | II-13 | III-53 |
| X-634 | I-5 | II-13 | III-53 |
| X-635 | I-6 | II-13 | III-53 |
| X-636 | I-57 | II-13 | III-53 |
| X-637 | I-2 | II-1 | III-54 |
| X-638 | I-5 | II-1 | III-54 |
| X-639 | I-6 | II-1 | III-54 |
| X-640 | I-57 | II-1 | III-54 |
| X-641 | I-2 | II-3 | III-54 |
| X-642 | I-5 | II-3 | III-54 |
| X-643 | I-6 | II-3 | III-54 |
| X-644 | I-57 | II-3 | III-54 |
| X-645 | I-2 | II-13 | III-54 |
| X-646 | I-5 | II-13 | III-54 |
| X-647 | I-6 | II-13 | III-54 |
| X-648 | I-57 | II-13 | III-54 |

Accordingly, the present invention furthermore to the quaternary mixtures as defined in Table Y, where a row corresponds in each case to a fungicidal composition comprising as component 1) one of the compounds I as defined and numbered above (Co. 1), and as component 2) one of the compounds II as defined and numbered above (Co. 2), and as component 3) the respective compound III as defined in table B (Co. 3) and as component 4) a further compound III as defined in table B (Co. 3), stated in the row in question.

Preferably, the compositions described comprise the active substances in synergistically effective amounts.

TABLE Y

Quarternary mixtures Y-1 to Y-432 comprising one compound I as defined and numbered above as component 1) (Co. 1) and one compound or biopesticide II as defined and numbered above as component 2) (Co. 2) and one compound III from groups A) to M) as defined and numbered in Table B as component 3) (Co. 3).

| Mixt. | Co. 1 | Co. 2 | Co. 3 | Co. 4 |
|---|---|---|---|---|
| Y-1 | I-2 | II-1 | III-1 | III-2 |
| Y-2 | I-5 | II-1 | III-1 | III-2 |
| Y-3 | I-6 | II-1 | III-1 | III-2 |
| Y-4 | I-57 | II-1 | III-1 | III-2 |
| Y-5 | I-2 | II-3 | III-1 | III-2 |
| Y-6 | I-5 | II-3 | III-1 | III-2 |
| Y-7 | I-6 | II-3 | III-1 | III-2 |
| Y-8 | I-57 | II-3 | III-1 | III-2 |
| Y-9 | I-2 | II-13 | III-1 | III-2 |
| Y-10 | I-5 | II-13 | III-1 | III-2 |
| Y-11 | I-6 | II-13 | III-1 | III-2 |
| Y-12 | I-57 | II-13 | III-1 | III-2 |
| Y-13 | I-2 | II-1 | III-1 | III-10 |
| Y-14 | I-5 | II-1 | III-1 | III-10 |
| Y-15 | I-6 | II-1 | III-1 | III-10 |
| Y-16 | I-57 | II-1 | III-1 | III-10 |
| Y-17 | I-2 | II-3 | III-1 | III-10 |
| Y-18 | I-5 | II-3 | III-1 | III-10 |
| Y-19 | I-6 | II-3 | III-1 | III-10 |
| Y-20 | I-57 | II-3 | III-1 | III-10 |
| Y-21 | I-2 | II-13 | III-1 | III-10 |
| Y-22 | I-5 | II-13 | III-1 | III-10 |
| Y-23 | I-6 | II-13 | III-1 | III-10 |
| Y-24 | I-57 | II-13 | III-1 | III-10 |
| Y-25 | I-2 | II-1 | III-1 | III-17 |
| Y-26 | I-5 | II-1 | III-1 | III-17 |
| Y-27 | I-6 | II-1 | III-1 | III-17 |
| Y-28 | I-57 | II-1 | III-1 | III-17 |
| Y-29 | I-2 | II-3 | III-1 | III-17 |
| Y-30 | I-5 | II-3 | III-1 | III-17 |
| Y-31 | I-6 | II-3 | III-1 | III-17 |
| Y-32 | I-57 | II-3 | III-1 | III-17 |
| Y-33 | I-2 | II-13 | III-1 | III-17 |
| Y-34 | I-5 | II-13 | III-1 | III-17 |
| Y-35 | I-6 | II-13 | III-1 | III-17 |
| Y-36 | I-57 | II-13 | III-1 | III-17 |
| Y-37 | I-2 | II-1 | III-2 | III-10 |
| Y-38 | I-5 | II-1 | III-2 | III-10 |
| Y-39 | I-6 | II-1 | III-2 | III-10 |
| Y-40 | I-57 | II-1 | III-2 | III-10 |
| Y-41 | I-2 | II-3 | III-2 | III-10 |
| Y-42 | I-5 | II-3 | III-2 | III-10 |
| Y-43 | I-6 | II-3 | III-2 | III-10 |
| Y-44 | I-57 | II-3 | III-2 | III-10 |
| Y-45 | I-2 | II-13 | III-2 | III-10 |
| Y-46 | I-5 | II-13 | III-2 | III-10 |
| Y-47 | I-6 | II-13 | III-2 | III-10 |
| Y-48 | I-57 | II-13 | III-2 | III-10 |
| Y-49 | I-2 | II-1 | III-2 | III-12 |
| Y-50 | I-5 | II-1 | III-2 | III-12 |
| Y-51 | I-6 | II-1 | III-2 | III-12 |
| Y-52 | I-57 | II-1 | III-2 | III-12 |
| Y-53 | I-2 | II-3 | III-2 | III-12 |
| Y-54 | I-5 | II-3 | III-2 | III-12 |
| Y-55 | I-6 | II-3 | III-2 | III-12 |
| Y-56 | I-57 | II-3 | III-2 | III-12 |
| Y-57 | I-2 | II-13 | III-2 | III-12 |
| Y-58 | I-5 | II-13 | III-2 | III-12 |
| Y-59 | I-6 | II-13 | III-2 | III-12 |
| Y-60 | I-57 | II-13 | III-2 | III-12 |
| Y-61 | I-2 | II-1 | III-2 | III-17 |
| Y-62 | I-5 | II-1 | III-2 | III-17 |
| Y-63 | I-6 | II-1 | III-2 | III-17 |
| Y-64 | I-57 | II-1 | III-2 | III-17 |
| Y-65 | I-2 | II-3 | III-2 | III-17 |
| Y-66 | I-5 | II-3 | III-2 | III-17 |
| Y-67 | I-6 | II-3 | III-2 | III-17 |
| Y-68 | I-57 | II-3 | III-2 | III-17 |

TABLE Y-continued

Quarternary mixtures Y-1 to Y-432 comprising one compound I as defined and numbered above as component 1) (Co. 1) and one compound or biopesticide II as defined and numbered above as component 2) (Co. 2) and one compound III from groups A) to M) as defined and numbered in Table B as component 3) (Co. 3).

| Mixt. | Co. 1 | Co. 2 | Co. 3 | Co. 4 |
|---|---|---|---|---|
| Y-69 | I-2 | II-13 | III-2 | III-17 |
| Y-70 | I-5 | II-13 | III-2 | III-17 |
| Y-71 | I-6 | II-13 | III-2 | III-17 |
| Y-72 | I-57 | II-13 | III-2 | III-17 |
| Y-73 | I-2 | II-1 | III-3 | III-12 |
| Y-74 | I-5 | II-1 | III-3 | III-12 |
| Y-75 | I-6 | II-1 | III-3 | III-12 |
| Y-76 | I-57 | II-1 | III-3 | III-12 |
| Y-77 | I-2 | II-3 | III-3 | III-12 |
| Y-78 | I-5 | II-3 | III-3 | III-12 |
| Y-79 | I-6 | II-3 | III-3 | III-12 |
| Y-80 | I-57 | II-3 | III-3 | III-12 |
| Y-81 | I-2 | II-13 | III-3 | III-12 |
| Y-82 | I-5 | II-13 | III-3 | III-12 |
| Y-83 | I-6 | II-13 | III-3 | III-12 |
| Y-84 | I-57 | II-13 | III-3 | III-12 |
| Y-85 | I-2 | II-1 | III-3 | III-27 |
| Y-86 | I-5 | II-1 | III-3 | III-27 |
| Y-87 | I-6 | II-1 | III-3 | III-27 |
| Y-88 | I-57 | II-1 | III-3 | III-27 |
| Y-89 | I-2 | II-3 | III-3 | III-27 |
| Y-90 | I-5 | II-3 | III-3 | III-27 |
| Y-91 | I-6 | II-3 | III-3 | III-27 |
| Y-92 | I-57 | II-3 | III-3 | III-27 |
| Y-93 | I-2 | II-13 | III-3 | III-27 |
| Y-94 | I-5 | II-13 | III-3 | III-27 |
| Y-95 | I-6 | II-13 | III-3 | III-27 |
| Y-96 | I-57 | II-13 | III-3 | III-27 |
| Y-97 | I-2 | II-1 | III-4 | III-22 |
| Y-98 | I-5 | II-1 | III-4 | III-22 |
| Y-99 | I-6 | II-1 | III-4 | III-22 |
| Y-100 | I-57 | II-1 | III-4 | III-22 |
| Y-101 | I-2 | II-3 | III-4 | III-22 |
| Y-102 | I-5 | II-3 | III-4 | III-22 |
| Y-103 | I-6 | II-3 | III-4 | III-22 |
| Y-104 | I-57 | II-3 | III-4 | III-22 |
| Y-105 | I-2 | II-13 | III-4 | III-22 |
| Y-106 | I-5 | II-13 | III-4 | III-22 |
| Y-107 | I-6 | II-13 | III-4 | III-22 |
| Y-108 | I-57 | II-13 | III-4 | III-22 |
| Y-109 | I-2 | II-1 | III-5 | III-5 |
| Y-110 | I-5 | II-1 | III-5 | III-10 |
| Y-111 | I-6 | II-1 | III-5 | III-10 |
| Y-112 | I-57 | II-1 | III-5 | III-10 |
| Y-113 | I-2 | II-3 | III-5 | III-10 |
| Y-114 | I-5 | II-3 | III-5 | III-10 |
| Y-115 | I-6 | II-3 | III-5 | III-10 |
| Y-116 | I-57 | II-3 | III-5 | III-10 |
| Y-117 | I-2 | II-13 | III-5 | III-10 |
| Y-118 | I-5 | II-13 | III-5 | III-10 |
| Y-119 | I-6 | II-13 | III-5 | III-10 |
| Y-120 | I-57 | II-13 | III-5 | III-10 |
| Y-121 | I-2 | II-1 | III-5 | III-40 |
| Y-122 | I-5 | II-1 | III-5 | III-40 |
| Y-123 | I-6 | II-1 | III-5 | III-40 |
| Y-124 | I-57 | II-1 | III-5 | III-40 |
| Y-125 | I-2 | II-3 | III-5 | III-40 |
| Y-126 | I-5 | II-3 | III-5 | III-40 |
| Y-127 | I-6 | II-3 | III-5 | III-40 |
| Y-128 | I-57 | II-3 | III-5 | III-40 |
| Y-129 | I-2 | II-13 | III-5 | III-40 |
| Y-130 | I-5 | II-13 | III-5 | III-40 |
| Y-131 | I-6 | II-13 | III-5 | III-40 |
| Y-132 | I-57 | II-13 | III-5 | III-40 |
| Y-133 | I-2 | II-1 | III-9 | III-23 |
| Y-134 | I-5 | II-1 | III-9 | III-23 |
| Y-135 | I-6 | II-1 | III-9 | III-23 |
| Y-136 | I-57 | II-1 | III-9 | III-23 |
| Y-137 | I-2 | II-3 | III-9 | III-23 |
| Y-138 | I-5 | II-3 | III-9 | III-23 |
| Y-139 | I-6 | II-3 | III-9 | III-23 |
| Y-140 | I-57 | II-3 | III-9 | III-23 |
| Y-141 | I-2 | II-13 | III-9 | III-23 |
| Y-142 | I-5 | II-13 | III-9 | III-23 |
| Y-143 | I-6 | II-13 | III-9 | III-23 |
| Y-144 | I-57 | II-13 | III-9 | III-23 |
| Y-145 | I-2 | II-1 | III-9 | III-30 |
| Y-146 | I-5 | II-1 | III-9 | III-30 |
| Y-147 | I-6 | II-1 | III-9 | III-30 |
| Y-148 | I-57 | II-1 | III-9 | III-30 |
| Y-149 | I-2 | II-3 | III-9 | III-30 |
| Y-150 | I-5 | II-3 | III-9 | III-30 |
| Y-151 | I-6 | II-3 | III-9 | III-30 |
| Y-152 | I-57 | II-3 | III-9 | III-30 |
| Y-153 | I-2 | II-13 | III-9 | III-30 |
| Y-154 | I-5 | II-13 | III-9 | III-30 |
| Y-155 | I-6 | II-13 | III-9 | III-30 |
| Y-156 | I-57 | II-13 | III-9 | III-30 |
| Y-157 | I-2 | II-1 | III-10 | III-11 |
| Y-158 | I-5 | II-1 | III-10 | III-11 |
| Y-159 | I-6 | II-1 | III-10 | III-11 |
| Y-160 | I-57 | II-1 | III-10 | III-11 |
| Y-161 | I-2 | II-3 | III-10 | III-11 |
| Y-162 | I-5 | II-3 | III-10 | III-11 |
| Y-163 | I-6 | II-3 | III-10 | III-11 |
| Y-164 | I-57 | II-3 | III-10 | III-11 |
| Y-165 | I-2 | II-13 | III-10 | III-11 |
| Y-166 | I-5 | II-13 | III-10 | III-11 |
| Y-167 | I-6 | II-13 | III-10 | III-11 |
| Y-168 | I-57 | II-13 | III-10 | III-11 |
| Y-169 | I-2 | II-1 | III-10 | III-31 |
| Y-170 | I-5 | II-1 | III-10 | III-31 |
| Y-171 | I-6 | II-1 | III-10 | III-31 |
| Y-172 | I-57 | II-1 | III-10 | III-31 |
| Y-173 | I-2 | II-3 | III-10 | III-31 |
| Y-174 | I-5 | II-3 | III-10 | III-31 |
| Y-175 | I-6 | II-3 | III-10 | III-31 |
| Y-176 | I-57 | II-3 | III-10 | III-31 |
| Y-177 | I-2 | II-13 | III-10 | III-31 |
| Y-178 | I-5 | II-13 | III-10 | III-31 |
| Y-179 | I-6 | II-13 | III-10 | III-31 |
| Y-180 | I-57 | II-13 | III-10 | III-31 |
| Y-181 | I-2 | II-1 | III-12 | III-23 |
| Y-182 | I-5 | II-1 | III-12 | III-23 |
| Y-183 | I-6 | II-1 | III-12 | III-23 |
| Y-184 | I-57 | II-1 | III-12 | III-23 |
| Y-185 | I-2 | II-3 | III-12 | III-23 |
| Y-186 | I-5 | II-3 | III-12 | III-23 |
| Y-187 | I-6 | II-3 | III-12 | III-23 |
| Y-188 | I-57 | II-3 | III-12 | III-23 |
| Y-189 | I-2 | II-13 | III-12 | III-23 |
| Y-190 | I-5 | II-13 | III-12 | III-23 |
| Y-191 | I-6 | II-13 | III-12 | III-23 |
| Y-192 | I-57 | II-13 | III-12 | III-23 |
| Y-193 | I-2 | II-1 | III-12 | III-24 |
| Y-194 | I-5 | II-1 | III-12 | III-24 |
| Y-195 | I-6 | II-1 | III-12 | III-24 |
| Y-196 | I-57 | II-1 | III-12 | III-24 |
| Y-197 | I-2 | II-3 | III-12 | III-24 |
| Y-198 | I-5 | II-3 | III-12 | III-24 |
| Y-199 | I-6 | II-3 | III-12 | III-24 |
| Y-200 | I-57 | II-3 | III-12 | III-24 |
| Y-201 | I-2 | II-13 | III-12 | III-24 |
| Y-202 | I-5 | II-13 | III-12 | III-24 |
| Y-203 | I-6 | II-13 | III-12 | III-24 |
| Y-204 | I-57 | II-13 | III-12 | III-24 |
| Y-205 | I-2 | II-1 | III-12 | III-25 |
| Y-206 | I-5 | II-1 | III-12 | III-25 |
| Y-207 | I-6 | II-1 | III-12 | III-25 |
| Y-208 | I-57 | II-1 | III-12 | III-25 |
| Y-209 | I-2 | II-3 | III-12 | III-25 |
| Y-210 | I-5 | II-3 | III-12 | III-25 |
| Y-211 | I-6 | II-3 | III-12 | III-25 |
| Y-212 | I-57 | II-3 | III-12 | III-25 |

TABLE Y-continued

Quarternary mixtures Y-1 to Y-432 comprising one compound I as defined and numbered above as component 1) (Co. 1) and one compound or biopesticide II as defined and numbered above as component 2) (Co. 2) and one compound III from groups A) to M) as defined and numbered in Table B as component 3) (Co. 3).

| Mixt. | Co. 1 | Co. 2 | Co. 3 | Co. 4 |
|---|---|---|---|---|
| Y-213 | I-2 | II-13 | III-12 | III-25 |
| Y-214 | I-5 | II-13 | III-12 | III-25 |
| Y-215 | I-6 | II-13 | III-12 | III-25 |
| Y-216 | I-57 | II-13 | III-12 | III-25 |
| Y-217 | I-2 | II-1 | III-12 | III-27 |
| Y-218 | I-5 | II-1 | III-12 | III-27 |
| Y-219 | I-6 | II-1 | III-12 | III-27 |
| Y-220 | I-57 | II-1 | III-12 | III-27 |
| Y-221 | I-2 | II-3 | III-12 | III-27 |
| Y-222 | I-5 | II-3 | III-12 | III-27 |
| Y-223 | I-6 | II-3 | III-12 | III-27 |
| Y-224 | I-57 | II-3 | III-12 | III-27 |
| Y-225 | I-2 | II-13 | III-12 | III-27 |
| Y-226 | I-5 | II-13 | III-12 | III-27 |
| Y-227 | I-6 | II-13 | III-12 | III-27 |
| Y-228 | I-57 | II-13 | III-12 | III-27 |
| Y-229 | I-2 | II-1 | III-12 | III-36 |
| Y-230 | I-5 | II-1 | III-12 | III-36 |
| Y-231 | I-6 | II-1 | III-12 | III-36 |
| Y-232 | I-57 | II-1 | III-12 | III-36 |
| Y-233 | I-2 | II-3 | III-12 | III-36 |
| Y-234 | I-5 | II-3 | III-12 | III-36 |
| Y-235 | I-6 | II-3 | III-12 | III-36 |
| Y-236 | I-57 | II-3 | III-12 | III-36 |
| Y-237 | I-2 | II-13 | III-12 | III-36 |
| Y-238 | I-5 | II-13 | III-12 | III-36 |
| Y-239 | I-6 | II-13 | III-12 | III-36 |
| Y-240 | I-57 | II-13 | III-12 | III-36 |
| Y-241 | I-2 | II-1 | III-15 | III-49 |
| Y-242 | I-5 | II-1 | III-15 | III-49 |
| Y-243 | I-6 | II-1 | III-15 | III-49 |
| Y-244 | I-57 | II-1 | III-15 | III-49 |
| Y-245 | I-2 | II-3 | III-15 | III-49 |
| Y-246 | I-5 | II-3 | III-15 | III-49 |
| Y-247 | I-6 | II-3 | III-15 | III-49 |
| Y-248 | I-57 | II-3 | III-15 | III-49 |
| Y-249 | I-2 | II-13 | III-15 | III-49 |
| Y-250 | I-5 | II-13 | III-15 | III-49 |
| Y-251 | I-6 | II-13 | III-15 | III-49 |
| Y-252 | I-57 | II-13 | III-15 | III-49 |
| Y-253 | I-2 | II-1 | III-17 | III-23 |
| Y-254 | I-5 | II-1 | III-17 | III-23 |
| Y-255 | I-6 | II-1 | III-17 | III-23 |
| Y-256 | I-57 | II-1 | III-17 | III-23 |
| Y-257 | I-2 | II-3 | III-17 | III-23 |
| Y-258 | I-5 | II-3 | III-17 | III-23 |
| Y-259 | I-6 | II-3 | III-17 | III-23 |
| Y-260 | I-57 | II-3 | III-17 | III-23 |
| Y-261 | I-2 | II-13 | III-17 | III-23 |
| Y-262 | I-5 | II-13 | III-17 | III-23 |
| Y-263 | I-6 | II-13 | III-17 | III-23 |
| Y-264 | I-57 | II-13 | III-17 | III-23 |
| Y-265 | I-2 | II-1 | III-19 | III-23 |
| Y-266 | I-5 | II-1 | III-19 | III-23 |
| Y-267 | I-6 | II-1 | III-19 | III-23 |
| Y-268 | I-57 | II-1 | III-19 | III-23 |
| Y-269 | I-2 | II-3 | III-19 | III-23 |
| Y-270 | I-5 | II-3 | III-19 | III-23 |
| Y-271 | I-6 | II-3 | III-19 | III-23 |
| Y-272 | I-57 | II-3 | III-19 | III-23 |
| Y-273 | I-2 | II-13 | III-19 | III-23 |
| Y-274 | I-5 | II-13 | III-19 | III-23 |
| Y-275 | I-6 | II-13 | III-19 | III-23 |
| Y-276 | I-57 | II-13 | III-19 | III-23 |
| Y-277 | I-2 | II-1 | III-23 | III-27 |
| Y-278 | I-5 | II-1 | III-23 | III-27 |
| Y-279 | I-6 | II-1 | III-23 | III-27 |
| Y-280 | I-57 | II-1 | III-23 | III-27 |
| Y-281 | I-2 | II-3 | III-23 | III-27 |
| Y-282 | I-5 | II-3 | III-23 | III-27 |
| Y-283 | I-6 | II-3 | III-23 | III-27 |
| Y-284 | I-57 | II-3 | III-23 | III-27 |
| Y-285 | I-2 | II-13 | III-23 | III-27 |
| Y-286 | I-5 | II-13 | III-23 | III-27 |
| Y-287 | I-6 | II-13 | III-23 | III-27 |
| Y-288 | I-57 | II-13 | III-23 | III-27 |
| Y-289 | I-2 | II-1 | III-23 | III-28 |
| Y-290 | I-5 | II-1 | III-23 | III-28 |
| Y-291 | I-6 | II-1 | III-23 | III-28 |
| Y-292 | I-57 | II-1 | III-23 | III-28 |
| Y-293 | I-2 | II-3 | III-23 | III-28 |
| Y-294 | I-5 | II-3 | III-23 | III-28 |
| Y-295 | I-6 | II-3 | III-23 | III-28 |
| Y-296 | I-57 | II-3 | III-23 | III-28 |
| Y-297 | I-2 | II-13 | III-23 | III-28 |
| Y-298 | I-5 | II-13 | III-23 | III-28 |
| Y-299 | I-6 | II-13 | III-23 | III-28 |
| Y-300 | I-57 | II-13 | III-23 | III-28 |
| Y-301 | I-2 | II-1 | III-23 | III-30 |
| Y-302 | I-5 | II-1 | III-23 | III-30 |
| Y-303 | I-6 | II-1 | III-23 | III-30 |
| Y-304 | I-57 | II-1 | III-23 | III-30 |
| Y-305 | I-2 | II-3 | III-23 | III-30 |
| Y-306 | I-5 | II-3 | III-23 | III-30 |
| Y-307 | I-6 | II-3 | III-23 | III-30 |
| Y-308 | I-57 | II-3 | III-23 | III-30 |
| Y-309 | I-2 | II-13 | III-23 | III-30 |
| Y-310 | I-5 | II-13 | III-23 | III-30 |
| Y-311 | I-6 | II-13 | III-23 | III-30 |
| Y-312 | I-57 | II-13 | III-23 | III-30 |
| Y-313 | I-2 | II-1 | III-23 | III-32 |
| Y-314 | I-5 | II-1 | III-23 | III-32 |
| Y-315 | I-6 | II-1 | III-23 | III-32 |
| Y-316 | I-57 | II-1 | III-23 | III-32 |
| Y-317 | I-2 | II-3 | III-23 | III-32 |
| Y-318 | I-5 | II-3 | III-23 | III-32 |
| Y-319 | I-6 | II-3 | III-23 | III-32 |
| Y-320 | I-57 | II-3 | III-23 | III-32 |
| Y-321 | I-2 | II-13 | III-23 | III-32 |
| Y-322 | I-5 | II-13 | III-23 | III-32 |
| Y-323 | I-6 | II-13 | III-23 | III-32 |
| Y-324 | I-57 | II-13 | III-23 | III-32 |
| Y-325 | I-2 | II-1 | III-23 | III-33 |
| Y-326 | I-5 | II-1 | III-23 | III-33 |
| Y-327 | I-6 | II-1 | III-23 | III-33 |
| Y-328 | I-57 | II-1 | III-23 | III-33 |
| Y-329 | I-2 | II-3 | III-23 | III-33 |
| Y-330 | I-5 | II-3 | III-23 | III-33 |
| Y-331 | I-6 | II-3 | III-23 | III-33 |
| Y-332 | I-57 | II-3 | III-23 | III-33 |
| Y-333 | I-2 | II-13 | III-23 | III-33 |
| Y-334 | I-5 | II-13 | III-23 | III-33 |
| Y-335 | I-6 | II-13 | III-23 | III-33 |
| Y-336 | I-57 | II-13 | III-23 | III-33 |
| Y-337 | I-2 | II-1 | III-24 | III-32 |
| Y-338 | I-5 | II-1 | III-24 | III-32 |
| Y-339 | I-6 | II-1 | III-24 | III-32 |
| Y-340 | I-57 | II-1 | III-24 | III-32 |
| Y-341 | I-2 | II-3 | III-24 | III-32 |
| Y-342 | I-5 | II-3 | III-24 | III-32 |
| Y-343 | I-6 | II-3 | III-24 | III-32 |
| Y-344 | I-57 | II-3 | III-24 | III-32 |
| Y-345 | I-2 | II-13 | III-24 | III-32 |
| Y-346 | I-5 | II-13 | III-24 | III-32 |
| Y-347 | I-6 | II-13 | III-24 | III-32 |
| Y-348 | I-57 | II-13 | III-24 | III-32 |
| Y-349 | I-2 | II-1 | III-25 | III-30 |
| Y-350 | I-5 | II-1 | III-25 | III-30 |
| Y-351 | I-6 | II-1 | III-25 | III-30 |
| Y-352 | I-57 | II-1 | III-25 | III-30 |
| Y-353 | I-2 | II-3 | III-25 | III-30 |
| Y-354 | I-5 | II-3 | III-25 | III-30 |
| Y-355 | I-6 | II-3 | III-25 | III-30 |
| Y-356 | I-57 | II-3 | III-25 | III-30 |

TABLE Y-continued

Quarternary mixtures Y-1 to Y-432 comprising one compound I as defined and numbered above as component 1) (Co. 1) and one compound or biopesticide II as defined and numbered above as component 2) (Co. 2) and one compound III from groups A) to M) as defined and numbered in Table B as component 3) (Co. 3).

| Mixt. | Co. 1 | Co. 2 | Co. 3 | Co. 4 |
|---|---|---|---|---|
| Y-357 | I-2 | II-13 | III-25 | III-30 |
| Y-358 | I-5 | II-13 | III-25 | III-30 |
| Y-359 | I-6 | II-13 | III-25 | III-30 |
| Y-360 | I-57 | II-13 | III-25 | III-30 |
| Y-361 | I-2 | II-1 | III-26 | III-28 |
| Y-362 | I-5 | II-1 | III-26 | III-28 |
| Y-363 | I-6 | II-1 | III-26 | III-28 |
| Y-364 | I-57 | II-1 | III-26 | III-28 |
| Y-365 | I-2 | II-3 | III-26 | III-28 |
| Y-366 | I-5 | II-3 | III-26 | III-28 |
| Y-367 | I-6 | II-3 | III-26 | III-28 |
| Y-368 | I-57 | II-3 | III-26 | III-28 |
| Y-369 | I-2 | II-13 | III-26 | III-28 |
| Y-370 | I-5 | II-13 | III-26 | III-28 |
| Y-371 | I-6 | II-13 | III-26 | III-28 |
| Y-372 | I-57 | II-13 | III-26 | III-28 |
| Y-373 | I-2 | II-1 | III-29 | III-41 |
| Y-374 | I-5 | II-1 | III-29 | III-41 |
| Y-375 | I-6 | II-1 | III-29 | III-41 |
| Y-376 | I-57 | II-1 | III-29 | III-41 |
| Y-377 | I-2 | II-3 | III-29 | III-41 |
| Y-378 | I-5 | II-3 | III-29 | III-41 |
| Y-379 | I-6 | II-3 | III-29 | III-41 |
| Y-380 | I-57 | II-3 | III-29 | III-41 |
| Y-381 | I-2 | II-13 | III-29 | III-41 |
| Y-382 | I-5 | II-13 | III-29 | III-41 |
| Y-383 | I-6 | II-13 | III-29 | III-41 |
| Y-384 | I-57 | II-13 | III-29 | III-41 |
| Y-385 | I-2 | II-1 | III-50 | III-51 |
| Y-386 | I-5 | II-1 | III-50 | III-51 |
| Y-387 | I-6 | II-1 | III-50 | III-51 |
| Y-388 | I-57 | II-1 | III-50 | III-51 |
| Y-389 | I-2 | II-3 | III-50 | III-51 |
| Y-390 | I-5 | II-3 | III-50 | III-51 |
| Y-391 | I-6 | II-3 | III-50 | III-51 |
| Y-392 | I-57 | II-3 | III-50 | III-51 |
| Y-393 | I-2 | II-13 | III-50 | III-51 |
| Y-394 | I-5 | II-13 | III-50 | III-51 |
| Y-395 | I-6 | II-13 | III-50 | III-51 |
| Y-396 | I-57 | II-13 | III-50 | III-51 |
| Y-397 | I-2 | II-1 | III-50 | III-52 |
| Y-398 | I-5 | II-1 | III-50 | III-52 |
| Y-399 | I-6 | II-1 | III-50 | III-52 |
| Y-400 | I-57 | II-1 | III-50 | III-52 |
| Y-401 | I-2 | II-3 | III-50 | III-52 |
| Y-402 | I-5 | II-3 | III-50 | III-52 |
| Y-403 | I-6 | II-3 | III-50 | III-52 |
| Y-404 | I-57 | II-3 | III-50 | III-52 |
| Y-405 | I-2 | II-13 | III-50 | III-52 |
| Y-406 | I-5 | II-13 | III-50 | III-52 |
| Y-407 | I-6 | II-13 | III-50 | III-52 |
| Y-408 | I-57 | II-13 | III-50 | III-52 |
| Y-409 | I-2 | II-1 | III-51 | III-53 |
| Y-410 | I-5 | II-1 | III-51 | III-53 |
| Y-411 | I-6 | II-1 | III-51 | III-53 |
| Y-412 | I-57 | II-1 | III-51 | III-53 |
| Y-413 | I-2 | II-3 | III-51 | III-53 |
| Y-414 | I-5 | II-3 | III-51 | III-53 |
| Y-415 | I-6 | II-3 | III-51 | III-53 |
| Y-416 | I-57 | II-3 | III-51 | III-53 |
| Y-417 | I-2 | II-13 | III-51 | III-53 |
| Y-418 | I-5 | II-13 | III-51 | III-53 |
| Y-419 | I-6 | II-13 | III-51 | III-53 |
| Y-420 | I-57 | II-13 | III-51 | III-53 |
| Y-421 | I-2 | II-1 | III-52 | III-54 |
| Y-422 | I-5 | II-1 | III-52 | III-54 |
| Y-423 | I-6 | II-1 | III-52 | III-54 |
| Y-424 | I-57 | II-1 | III-52 | III-54 |
| Y-425 | I-2 | II-3 | III-52 | III-54 |
| Y-426 | I-5 | II-3 | III-52 | III-54 |
| Y-427 | I-6 | II-3 | III-52 | III-54 |
| Y-428 | I-57 | II-3 | III-52 | III-54 |
| Y-429 | I-2 | II-13 | III-52 | III-54 |
| Y-430 | I-5 | II-13 | III-52 | III-54 |
| Y-431 | I-6 | II-13 | III-52 | III-54 |
| Y-432 | I-57 | II-13 | III-52 | III-54 |

The mixtures and compositions according to the invention are suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

The mixtures and compositions according to the invention are particularly important in the control of a multitude of phytopathogenic fungi on various cultivated plants, such as cereals, e. g. wheat, rye, barley, triticale, oats or rice; beet, e. g. sugar beet or fodder beet; fruits, such as pomes, stone fruits or soft fruits, e. g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; natural rubber plants or ornamental and forestry plants, such as flowers, shrubs, broad-leaved trees or evergreens, e. g. conifers; and on the plant propagation material, such as seeds, and the crop material of these plants.

Preferably the inventive mixtures and compositions are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with the inventive combination of compound I and compounds II and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://cera-gmc.org/, see GM crop database therein). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transitional modification of protein(s), oligo- or polypeptides e. g. by glycosylation or polymer additions such as prenylated, acetylated or farnesylated moieties or PEG moieties.

Plants that have been modified by breeding, mutagenesis or genetic engineering, e. g. have been rendered tolerant to applications of specific classes of herbicides, such as hydroxyphenylpyruvate dioxygenase (HPPD) inhibitors; acetolactate synthase (ALS) inhibitors, such as sulfonyl ureas (see e. g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e. g. U.S. Pat. No. 6,222,100, WO 01/82685, WO 00/026390, WO 97/41218, WO 98/002526, WO 98/02527, WO 04/106529, WO 05/20673, WO 03/014357, WO 03/13225, WO 03/14356, WO 04/16073); enolpyruvylshikimate-3-phosphate synthase (EPSPS) inhibitors, such as glyphosate (see e. g. WO 92/00377); glutamine synthetase (GS) inhibitors, such as glufosinate (see e.g. EP-A 242 236, EP-A 242 246) or oxynil herbicides (see e. g. U.S. Pat. No. 5,559,024) as a result of conventional methods of breeding or genetic engineering. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phytophthora infestans* derived from the mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany).

The inventive mixtures and compositions are particularly suitable for controlling the following plant diseases:

*Albugo* spp. (white rust) on ornamentals, vegetables (e. g. *A. candida*) and sunflowers (e. g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e. g. *A. solani* or *A. alternata*), tomatoes (e. g. *A. solani* or *A. alternata*) and wheat; *Aphanomyces* spp. on sugar beets and vegetables; *Ascochyta* spp. on cereals and vegetables, e. g. *A. tritici*(anthracnose) on wheat and A. horde/on barley; *Bipolaris* and *Drechslera* spp. (teleomorph: *Cochliobolus* spp.) on corn (e. g. *D. maydis*), cereals (e. g. *B. sorokiniana*: spot blotch), rice (e. g. *B. oryzae*) and turfs; *Blumeria* (formerly *Erysiphe*) *graminis* (powdery mildew) on cereals (e. g. on wheat or barley); *Botrytis cinerea* (teleomorph: *Botryotinia fuckeliana*: grey mold) on fruits and berries (e. g. strawberries), vegetables (e. g. lettuce, carrots, celery and cabbages), rape, flowers, vines, forestry plants and wheat; *Bremia lactucae* (downy mildew) on lettuce;

*Ceratocystis* (syn. *Ophiostoma*) spp. (rot or wilt) on broad-leaved trees and evergreens, e. g. *C. ulmi* (Dutch elm disease) on elms; *Cercospora* spp. (*Cercospora* leaf spots) on corn, rice, sugar beets (e. g. *C. beticola*), sugar cane, vegetables, coffee, soybeans (e. g. *C. sojina* or *C. kikuchii*) and rice; *Cladosporium* spp. on tomatoes (e. g. *C. fulvurr*: leaf mold) and cereals, e. g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e. g. *C. sativus*, anamorph: *B. sorokiniana*) and rice (e. g. *C. miyabeanus*, anamorph: *H. oryzae*); *Colletotrichum* (teleomorph: *Glomerella*) spp. (anthracnose) on cotton (e. g. *C. gossypii*), corn (e. g. *C. graminicola*), soft fruits, potatoes (e. g. *C. coccodes*, black dot), beans (e. g. *C. lindemuthianum*) and soybeans (e. g. *C. truncatum* or *C. gloeosporioides*); *Corticium* spp., e. g. *C. sasakii* (sheath blight) on rice; *Corynespora cassiicola* (leaf spots) on soybeans and ornamentals; *Cycloconium* spp., e. g. *C. oleaginum* on olive trees; *Cylindrocarpon* spp. (e. g. fruit tree canker or young vine decline, teleomorph: *Nectria* or *Neonectria* spp.) on fruit trees, vines (e. g. *C. liriodendri*, teleomorph: *Neonectria liriodendri* Black Foot Disease) and ornamentals; *Dematophora* (teleomorph: *Rosellinia*) *necatrix* (root and stem rot) on soybeans; *Diaporthe* spp., e. g. *D. phaseolorum* (damping off) on soybeans; *Drechslera* (syn. *Helminthosporium*, teleomorph: *Pyrenophora*) spp. on corn, cereals, such as barley (e. g. *D. teres*, net blotch) and wheat (e. g. *D. tritici-repentis*, tan spot), rice and turf; *Esca* (dieback, apoplexy) on vines, caused by *Formtiporia* (syn. *Phellinus*) *punctata, F. mediterranea, Phaeomoniella chlamydospora* (earlier *Phaeoacremonium chlamydosporum*), *Phaeoacremonium aleophilum* and/or *Botryosphaeria obtusa*; *Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e. g. *E. pisi*), such as cucurbits (e. g. *E. cichoracearum*), cabbages, rape (e. g. *E. cruciferarum*); *Eutypa lata* (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e. g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e. g. wheat or barley), *F. oxysporum* on tomatoes, *F. solani* (f. sp. *glycines* now syn. *F. virguliforme*) and *F. tucumaniae* and *F. brasiliense* each causing sudden death syndrome on soybeans, and *F. verticillioides* on corn; *Gaeumannomyces graminis* (take-all) on cereals (e. g. wheat or barley) and corn; *Gibberella* spp. on cereals (e. g. *G. zeae*) and rice (e. g. *G. fujikuroi* Bakanae disease); *Glomerella cingulata* on vines, pome fruits and other plants and *G. gossypiion* cotton; Grainstaining complex on rice; *Guignardia bidwellii* (black rot) on vines; *Gymnosporangium* spp. on rosaceous plants and junipers, e. g. *G. sabinae* (rust) on pears; *Helminthosporium* spp. (syn. *Drechslera*, teleomorph: *Cochliobolus*) on corn, cereals and rice; *Hemileia* spp., e. g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e. g. wheat or barley); *Microsphaera diffusa* (powdery mildew) on soybeans; *Monilinia* spp., e. g. *M. laxa, M. fructicola* and *M. fructigena* (bloom and twig blight, brown rot) on stone fruits and other rosaceous plants; *Mycosphaerella* spp. on cereals, bananas, soft fruits and ground nuts, such as e. g. *M. graminicola* (anamorph: *Septoria tritici, Septoria* blotch) on wheat or *M. fijiensis* (black Sigatoka disease) on bananas; *Peronospora* spp. (downy mildew) on cabbage (e. g. *P. brassicae*), rape (e. g. *P. parasitica*), onions (e. g. P. destructor), tobacco (*P. tabacina*) and soybeans (e. g. *P. manshurica*); *Phakopsora pachyrhizi* and *P. meibomiae* (soybean rust) on soybeans; *Phialophora* spp. e. g. on vines (e. g. *P. tracheiphila* and *P. tetraspora*) and soybeans (e. g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e. g. *P. viticola*: can and leaf spot) and soybeans (e. g. stem rot: *P. phaseoli* teleomorph: *Diaporthe phaseolorum*); *Physoderma maydis* (brown spots) on corn; *Phytophthora* spp. (wilt, root, leaf, fruit and stem root) on various plants, such as paprika and cucurbits (e. g. *P. capsici*), soybeans (e. g. *P. megasperma*, syn. *P. sojae*), potatoes and tomatoes (e. g. *P. infestans*, late blight) and broad-leaved trees (e. g. *P. ramorum*: sudden oak death); *Plasmodiophora brassicae* (club root) on cabbage, rape, radish and other plants; *Plasmopara* spp., e. g. *P. viticola* (grapevine downy mildew) on vines and *P. halstedii* on sunflowers; *Podosphaera* spp. (powdery mildew) on rosaceous plants, hop, pome and soft fruits, e. g. *P. leucotricha* on apples; *Polymyxa* spp., e. g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e. g. wheat or barley; *Pseudoperonospora* (downy mildew) on various plants, e. g. *P. cubensis* on cucurbits or P. hum/lion hop; *Pseudopezicula tracheiphila* (red fire disease or, rotbrenner', anamorph: *Phialophora*) on vines; *Puccinia* spp. (rusts) on various plants, e. g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye, and asparagus (e. g. *P. asparagi*); *Pyrenophora* (anamorph: *Drechslera*) *tritici-repentis* (tan spot) on wheat or *P. teres* (net blotch) on barley; *Pyricularia* spp., e. g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e. g. *P. ultimum* or *P. aphanidermatum*); *Ramularia* spp., e. g. *R. collo-cygni* (*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e. g. *R. solani* (root and stem rot) on soybeans, *R. solani* (sheath blight) on rice or *R. cerealis* (*Rhizoctonia* spring blight) on wheat or barley; *Rhizopus stolonifer*(black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e. g. *S. scerotiorum*) and soybeans (e. g. *S. rolfsii* or *S. scerotiorum*); *Septoria* spp. on various plants, e. g. *S. glycines* (brown spot) on soybeans, *S. tritici*(*Septoria* blotch) on wheat and *S.* (syn. *Stagonospora*) *nodorum* (*Stagonospora* blotch) on cereals; *Uncinula* (syn. *Erysiphe*) *necator* (powdery mildew, anamorph: *Oidium tuckeri*) on vines; *Setospaeria* spp. (leaf blight) on corn (e. g. *S. turcicum*, syn. *Helminthosporium turcicum*) and turf; *Sphacelotheca* spp. (smut) on corn, (e. g. *S. reiliana*: head smut), sorghum und sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e. g. *S. nodorum* (*Stagonospora* blotch, teleomorph: *Leptosphaeria* [syn. *Phaeosphaeria]nodorum*) on wheat; *Synchytrium endobioticum* on potatoes (potato wart disease); *Taphrina* spp., e. g. *T. deformans* (leaf curl disease) on peaches and *T. pruni* (plum pocket) on plums; *Thielaviopsis* spp. (black root rot) on tobacco, pome fruits, vegetables, soybeans and cotton, e. g. *T. basicola* (syn. *Chalara elegans*); *Tilletia* spp. (common bunt or stinking smut) on cereals, such as e. g. *T. tritici* (syn. *T. caries*, wheat bunt) and *T. controversa* (dwarf bunt) on wheat; *Typhula incarnata* (grey snow mold) on barley or wheat; *Urocystis* spp., e. g. *U. occulta* (stem smut) on rye; *Uromyces* spp. (rust) on vegetables, such as beans (e. g. *U. appendiculatus*, syn. *U. phaseoli*) and sugar beets (e. g. *U. betae*); *Ustilago* spp. (loose smut) on cereals (e. g. *U. nuda* and *U. avaenae*), corn (e. g. *U. maydis*: corn smut) and sugar cane; *Venturia* spp. (scab) on apples (e. g. *V. inaequalis*) and pears; and *Verticillium* spp. (wilt) on various plants, such as fruits and ornamentals, vines, soft fruits, vegetables and field crops, e. g. *V. dahilae* on strawberries, rape, potatoes and tomatoes.

The inventive mixtures and compositions are also suitable for controlling harmful fungi in the protection of stored products or harvest and in the protection of materials. The term "protection of materials" is to be understood to denote the protection of technical and non-living materials, such as adhesives, glues, wood, paper and paperboard, textiles, leather, paint dispersions, plastics, coiling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pullulans, Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicllium* spp., *Trichorma* spp., *Alternaria* spp., *Paecilomyces* spp. and Zygomycetes such as *Mucor* spp., and in addition in the protection of stored products and harvest the following yeast fungi are worthy of note: *Candida* spp. and *Saccharomyces cerevisae*.

In particular, the mixtures and compositions of the present invention are effective against plant pathogens in specialty crops such as vine, fruits, hop, vegetables and tobacco—see the above list.

Plant propagation materials may be treated with the mixtures and compositions of the invention prophylactically either at or before planting or transplanting.

The invention also relates to agrochemical compositions comprising an auxiliary and at least one compound I and at least one compound II according to the invention.

An agrochemical composition comprises a fungicidally effective amount of a compound I and a compound II. The term "effective amount" denotes an amount of the composition or of the compounds I, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound I used.

The compounds I and II, their N-oxides and salts can be converted into customary types of agrochemical compositions, e. g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, $6^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkyliso-thiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are (wherein active substances denote at least one compound I and one compound II):

i) Water-soluble concentrates (SL, LS)

10-60 wt % active substances and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible concentrates (DC)

5-25 wt % active substances and 1-10 wt % dispersant (e.g. polyvinylpyrrolidone) are dissolved in organic solvent (e.g. cyclohexanone) ad 100 wt %. Dilution with water gives a dispersion.

iii) Emulsifiable concentrates (EC)

15-70 wt % active substances and 5-10 wt % emulsifiers (e.g. calcium dodecylben-zenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % active substances and 1-10 wt % emulsifiers (e.g. calcium dodecylben-zenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % active substances are comminuted with addition of 2-10 wt % dispersants and wetting agents (e.g. sodium lignosulfonate and alcohol ethoxylate), 0.1-2 wt % thickener (e.g. xanthan gum) and ad water ad 100 wt % to give a fine active substance suspension. Dilution with water gives a stable suspension of the active substance. For FS type composition up to 40 wt % binder (e.g. polyvinylalcohol) is added.

vi) Water-dispersible granules and water-soluble granules (WG, SG)

50-80 wt % active substances are ground finely with addition of dispersants and wetting agents (e.g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-dispersible powders and water-soluble powders (WP, SP, WS)

50-80 wt % active substances are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % active substances are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

iv) Microemulsion (ME)

5-20 wt % active substances are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100 wt %. This mixture is stirred for 1 h to produce spontaneously a thermodynamically stable microemulsion.

iv) Microcapsules (CS)

An oil phase comprising 5-50 wt % active substances, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

ix) Dustable powders (DP, DS)

1-10 wt % active substances are ground finely and mixed intimately with solid carrier (e.g. finely divided kaolin) ad 100 wt %.

x) Granules (GR, FG)

0.5-30 wt % active substances are ground finely and associated with solid carrier (e.g. silicate) ad 100 wt %. Granulation is achieved by extrusion, spray-drying or fluidized bed.

xi) Ultra-low volume liquids (UL)

1-50 wt % active substances are dissolved in organic solvent (e.g. aromatic hydrocarbon) ad 100 wt %.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active substances. The active substances are employed in a purity of from 90% to 100%, preferably from 95% to 100% (according to NMR spectrum).

Solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40%, in the ready-to-use preparations. Application can be carried out before or during sowing. Methods for applying or treating compound I and compound II and compositions thereof, respectively, on to plant propagation material, especially seeds include dressing, coating, pelleting, dusting, soaking and in-furrow application methods of the propagation material. Preferably, compound I and compound or biopesticide II or the compositions thereof, respectively, are applied on to the plant propagation material by a method such that germination is not induced, e. g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha.

In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

In the binary mixtures and compositions according to the invention, the weight ratio of compound I and compound or biopesticide II generally depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1, even more preferably in the range of from 1:4 to 4:1 and in particular in the range of from 1:2 to 2:1.

According to further embodiments of the binary mixtures and compositions according to the invention, the weight ratio of compound I versus compound II usually is in the range of from 100:1 to 1:1, regularly in the range of from 50:1 to 1:1, preferably in the range of from 20:1 to 1:1, more preferably in the range of from 10:1 to 1:1, even more preferably in the range of from 4:1 to 1:1 and in particular in the range of from 2:1 to 1:1.

According to further embodiments of the binary mixtures and compositions according to the invention, the weight ratio of compound I versus compound II usually is in the range of from 1:1 to 1:100, regularly in the range of from 1:1 to 1:50, preferably in the range of from 1:1 to 1:20, more preferably in the range of from 1:1 to 1:10, even more preferably in the range of from 1:1 to 1:4 and in particular in the range of from 1:1 to 1:2.

In the ternary mixtures, i.e. compositions according to the invention comprising one compound I (component 1) and a compound II (component 2) and a compound III (component 3), the weight ratio of component 1) and component 2) depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1, and the weight ratio of component 1) and component 3) usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1.

Any further active components are, if desired, added in a ratio of from 20:1 to 1:20 to the compound I.

In the mixtures and compositions, the compound ratios (e.g. compound I/compound II/compound III ratio) are advantageously chosen so as to produce a synergistic effect.

The term "synergistic effect" is understood to refer in particular to that defined by Colby's formula (Colby, S. R., "Calculating synergistic and antagonistic responses of herbicide combinations", Weeds, 15, pp. 20-22, 1967).

The term "synergistic effect" is also understood to refer to that defined by application of the Tammes method, (Tammes, P. M. L., "Isoboles, a graphic representation of synergism in pesticides", Netherl. J. Plant Pathol. 70, 1964).

The components can be used individually or already partially or completely mixed with one another to prepare the composition according to the invention. It is also possible for them to be packaged and used as combination such as a kit of parts.

Microbial pesticides comprising (entomopathogenic) nematodes can be mass prepared as for use as biopesticides using in vivo or in vitro methods (Shapiro-Ilan and Gaugler 2002). In vivo production (culture in live insect hosts) requires a low level of technology, has low startup costs, and resulting nematode quality is generally high, yet cost efficiency is low. The approach can be considered ideal for small markets. In vivo production may be improved through innovations in mechanization and streamlining. A novel alternative approach to in vivo methodology is production and application of nematodes in infected host cadavers; the cadavers (with nematodes developing inside) are distributed directly to the target site and pest suppression is subsequently achieved by the infective juveniles that emerge. In vitro solid culture, i.e., growing the nematodes on crumbled polyurethane foam, offers an intermediate level of technology and costs. In vitro liquid culture is the most cost-efficient production method but requires the largest startup capital. Liquid culture may be improved through progress in media development, nematode recovery, and bioreactor design. A variety of formulations have been developed to facilitate nematode storage and application including activated charcoal, alginate and polyacrylamide gels, baits, clay, paste, peat, polyurethane sponge, vermiculite, and water-dispersible granules. Depending on the formulation and nematode species, successful storage under refrigeration ranges from one to seven months. Optimum storage temperature for formulated nematodes varies according to species; generally, steinernematids tend to store best at 4-8° C. whereas heterorhabditids persist better at 10-15° C. Nematodes are formulated and applied as infective juveniles, the only free-living and therefore environmentally tolerant stage. Infective juveniles range from 0.4 to 1.5 mm in length and can be observed with a hand lens or microscope after separation from formulation materials. Disturbed nematodes move actively, however sedentary ambusher species (e.g. *Steinernema carpocapsae, S. scapterisci*) in water soon revert to a characteristic "J"-shaped resting position. Low temperature or oxygen levels will inhibit movement of even active cruiser species (e.g., *S. glaseri, Heterorhabditis bacteriophora*). In short, lack of movement is not always a sign of mortality; nematodes may have to be stimulated (e.g., probes, acetic acid, gentle heat) to move before assessing viability. Good quality nematodes tend to possess high lipid levels that provide a dense appearance, whereas nearly transparent nematodes are often active but possess low powers of infection. Infective juveniles are compatible with most but not all agricultural chemicals under field conditions. Compatibility has been tested with well over 100 different chemical pesticides. Entomopathogenic nematodes are compatible (e.g., may be tank-mixed) with most chemical herbicides and fungicides as well as many insecticides (such as bacterial or fungal products) (Koppenhöfer and Grewal, 2005).

According to the invention, the solid material (dry matter) of the biopesticides II are considered as active components (e.g. to be obtained after drying or evaporation of the extraction medium or the suspension medium in case of liquid formulations of the microbial pesticides).

In accordance with the present invention, the weight ratios and percentages used herein for biological extracts such as Quillay extract are based on the total weight of the dry content (solid material) of the respective extract(s).

For microbial pesticides II selected from groups D), F) and H), weight ratios and/or percentages refer to the total weight of a preparation of the respective biopesticide II with at least $1\times10^6$ CFU/g ("colony forming units per gram total weight"), preferably with at least $1\times10^8$ CFU/g, even more preferably from $1\times10^8$ to $1\times10^{12}$ CFU/g dry matter. Colony forming unit is measure of viable microbial cells, in particular fungal and bacterial cells. In addition, here CFU may also be understood as number of (juvenile) individual nematodes in case of (entomopathogenic) nematode biopesticides, such as *Steinernema feltiae*.

In the mixtures and compositions according to the invention the weight ratio of the component 1) and the component 2) generally depends from the properties of the active components used, usually it is in the range of from 1:10,000 to 10,000:1, regularly in the range of from 100:1 to 1:10,000, preferably in the range of from 100:1 to 1:5,000, more preferably in the range of from 1:1 to 1:1,000, even more preferably in the range of from 1:1 to 1:500 and in particular in the range of from 1:10 to 1:300.

According to further embodiments of the mixtures and compositions, the weight ratio of the component 1) and component 2) usually is in the range of from 20,000:1 to 1:10, often in the range of from 10,000:1 to 1:1, regularly in the range of from 5,000:1 to 5:1, preferably in the range of from 5,000:1 to 10:1, more preferably in the range of from 2,000:1 to 30:1, even more preferably in the range of from 2,000:1 to 100:1 and in particular in the range of from 1,000:1 to 100:1.

According to further embodiments of the mixtures and compositions, the weight ratio of the component 1) and the component 2) usually is in the range of from 1:1 to 1:1000, often in the range of from 1:1 to 1:100, regularly in the range of from 1:1 to 1:50, preferably in the range of from 1:1 to 1:20, more preferably in the range of from 1:1 to 1:10, even more preferably in the range of from 1:1 to 1:4 and in particular in the range of from 1:1 to 1:2.

These ratios are suitable for inventive mixtures applied by seed treatment.

Herein, microbial pesticides II selected from groups D), F) and H) may be supplied in any physiological state such as active or dormant. Such dormant active component may be supplied for example frozen, dried, or lyophilized or partly desiccated (procedures to produce these partly desiccated organisms are given in WO2008/002371) or in form of spores.

Microbial pesticides II selected from groups D), F) and H) used as organism in an active state can be delivered in a growth medium without any additional additives or materials or in combination with suitable nutrient mixtures. According to one embodiment, the compositions comprise between 0.01 and 90% (w/w) of component 1) and from $1\times10^5$ CFU to $1\times10^{12}$ CFU of component 2) per gram total weight of the composition. According to another embodiment, the compositions comprise between 5 and 70% (w/w) of component 1) and from $1\times10^6$ CFU to $1\times10^{10}$ CFU of component 2) per gram total weight of the composition. According to another embodiment, the compositions comprise between 25 and 70% (w/w) of component 1) and from $1\times10^7$ CFU to $1\times10^9$ CFU of component 2) per gram total weight of the composition.

In the ternary mixtures, i.e. compositions according to the invention comprising the component 1) and component 2) and a compound III (component 3), the weight ratio of component 1) and component 2) depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1, and the weight ratio of component 1) and component 3) usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1.

In the mixtures and compositions, the compound ratios are advantageously chosen so as to produce a synergistic effect.

The total weight ratios of compositions wherein component 2) is selected from groups D), F) or H) can be determined based on the weight of component 1) using the amount of CFU of component 2) to calculate the total weight of component 2) with the following equation that $1\times10^{10}$ CFU equals one gram of total weight of component 2).

The agrochemical compositions generally are characterized in that they contain an effective quantity of the active components as defined above. Generally, they contain between 0.01 and 95%, preferably between 0.1 and 90%, and in particular between 0.5 and 75%, by weight of active components.

The fungicidal action of the compositions according to the invention can be shown by the tests described below.

The active compounds, separately or jointly, are prepared as a stock solution comprising 25 mg of active compound which is made up to 10 ml using a mixture of acetone and/or DMSO and the emulsifier Uniperol® EL (wetting agent having an emulsifying and dispersing action based on ethoxylated alkylphenols) in a ratio by volume of solvent/emulsifier of 99:1. The mixture is then made up to 100 ml with water. This stock solution is diluted with the solvent/emulsifier/water mixture described to give the concentration of active compound stated below.

The visually determined percentages of infected leaf areas are converted into efficacies in % of the untreated control. The efficacy (E) is calculated as follows using Abbot's formula:

$$E=(1-\alpha/\beta)\cdot 100$$

α corresponds to the fungicidal infection of the treated plants in % and
β corresponds to the fungicidal infection of the untreated (control) plants in %

An efficacy of 0 means that the infection level of the treated plants corresponds to that of the untreated control plants; an efficacy of 100 means that the treated plants were not infected.

The expected efficacies of active compound combinations were determined using Colby's formula (Colby, S. R. "Calculating synergistic and antagonistic responses of herbicide combinations", Weeds, 15, pp. 20-22, 1967) and compared with the observed efficacies.

$$E=x+y-x\cdot y/100 \qquad \text{Colby's formula:}$$

E expected efficacy, expressed in % of the untreated control, when using the mixture of the active compounds A and B at the concentrations a and b
x efficacy, expressed in % of the untreated control, when using the active compound A at the concentration a
y efficacy, expressed in % of the untreated control, when using the active compound B at the concentration b.

Microtests

The active compounds were formulated separately as a stock solution having a concentration of 10000 ppm in dimethyl sulfoxide.

The product orysastrobin was used as commercial finished formulation and diluted with water to the stated concentration of the active compound.

The stock solutions were mixed according to the ratio, pipetted onto a micro titer plate (MTP) and diluted with water to the stated concentrations. A spore suspension of the respective pathogen in the respective nutrient medium was then added. The plates were placed in a water vapor-saturated chamber at a temperature of 18° C. Using an absorption photometer, the MTPs were measured at 405 nm 7 days after the inoculation.

The measured parameters were compared to the growth of the active compound-free control variant (100%) and the fungus-free and active compound-free blank value to determine the relative growth in % of the pathogens in the respective active compounds. These percentages were converted into efficacies.

The expected efficacies of active compound mixtures were determined using Colby's formula [R. S. Colby, "Calculating synergistic and antagonistic responses of herbicide combinations", Weeds 15, 20-22 (1967)] and compared with the observed efficacies.

Use Example 1. Activity Against the Late Blight Pathogen *Phytophthora infestans*

A spore suspension of *Phytophthora infestans* containing a pea juice-based aqueous nutrient medium or DDC medium was used. Results are given in Table 1.

TABLE 1

| Active compound/mixture | Concentration (ppm) | Mixture ratio | Observed efficacy | Calculated efficacy acc. to Colby (%) |
|---|---|---|---|---|
| II-6 | 0.063 | — | 7 | |
| I-13 | 0.063 | — | 4 | |
| II-6 + I-13 | 0.063 + 0.063 | 1:1 | 65 | 10 |

Use Example 2. Activity Against the Rice Blast Pathogen *Pyricularia oryzae*

A spore suspension of *P. oryzae* containing an aqueous viomalt or yeast-bactopeptone-glycerine solution was used. Results are given in Table 2.

TABLE 2

| Active compound/mixture | Concentration (ppm) | Mixture ratio | Observed efficacy | Calculated efficacy acc. to Colby (%) |
|---|---|---|---|---|
| II-2 | 0.016 | — | 6 | |
| I-13 | 0.00025 | — | 7 | |
| II-2 + I-13 | 0.016 + 0.00025 | 63:1 | 32 | 13 |

Use Example 3. Activity Against the Wheat Leaf Spot Pathogen *Leptosphaeria nodorum*

A spore suspension of *L. nodorum* containing aqueous viomalt or yeast-bactopeptone-glycerine solution was used. Results are given in Table 3.

TABLE 3

| Active compound/mixture | Concentration (ppm) | Mixture ratio | Observed efficacy | Calculated efficacy acc. to Colby (%) |
|---|---|---|---|---|
| II-6 | 0.004 | — | 7 | |
| I-13 | 0.004 | — | 21 | |
| II-6 + I-13 | 0.004 + 0.004 | 1:1 | 51 | 26 |

The invention claimed is:

1. A mixture, comprising as active components
1) at least one compound of formula I wherein
n is an integer and is 0, 1, 2, 3, 4 or 5; and
R, which may be the same or different to any other R, is halogen, hydroxyl, carboxyl, $C_1$-$C_4$-alkyl, $C_2$-$C_4$-alkenyl, $C_2$-$C_8$-alkynyl, $C_1$-$C_4$-haloalkyl, $C_1$-$C_4$-alkoxy, $C_1$-$C_4$-haloalkoxy, $C_1$-$C_4$-alkylsulfanyl, $C_1$-$C_4$-haloalkylsulfanyl, $C_1$-$C_6$-alkoxyimino-$C_1$-$C_4$-alkyl, $C_2$-$C_6$-alkenyloxyimino-$C_1$-$C_4$-alkyl, $C_2$-$C_6$-alkynyloxyimino-$C_1$-$C_4$-alkyl, $C_1$-$C_4$-alkoxyimino-$C_1$-$C_4$-alkyl, $C_1$-$C_6$-alkoxyimino-, $C_2$-$C_6$-alkenyloxyimino-, $C_2$-$C_6$-alkynyloxyimino-, $C_2$-$C_6$-haloalkenyloxyimino-, $C_3$-$C_6$-cycloalkyl, $C_3$-$C_6$-cycloalkenyl, or phenyl;

and 2) at least one fungicidally active compound II selected from group consisting of:
2-[2-chloro-4-(4-chlorophenoxy)phenyl]-1-(1,2,4-triazol-1-yl)pentan-2-ol; 1-[4-(4-chlorophenoxy)-2-(trifluoromethyl)phenyl]-1-cyclopropyl-2-(1,2,4-triazol-1-yl)ethanol; 2-[4-(4-chlorophenoxy)-2-(trifluoromethyl)phenyl]-1-(1,2,4-triazol-1-yl)butan-2-ol; 2-[2-chloro-4-(4-chlorophenoxy)phenyl]-1-(1,2,4-triazol-1-yl)butan-2-ol; 2-[4-(4-chlorophenoxy)-2-(trifluoromethyl)phenyl]-3-methyl-1-(1,2,4-triazol-1-yl)butan-2-ol; 2-[4-(4-chlorophenoxy)-2-(trifluoromethyl)phenyl]-1-(1,2,4-triazol-1-yl)propan-2-ol; 2-[2-chloro-4-(4-chlorophenoxy)phenyl]-3-methyl-1-(1,2,4-triazol-1-yl)butan-2-ol; 2-[4-(4-chlorophenoxy)-2-(trifluoromethyl)phenyl]-1-(1,2,4-triazol-1-yl)pentan-2-ol; 2-[4-(4-fluorophenoxy)-2-(trifluoromethyl)phenyl]-1-(1,2,4-triazol-1-yl)propan-2-ol; 2-[2-chloro-4-(4-chlorophenoxy)phenyl]-1-(1,2,4-triazol-1-yl)pent-3-yn-2-ol; 1-[2-chloro-4-(4-chlorophenoxy)phenyl]-1-cyclopropyl-2-(1,2,4-triazol-1-yl)ethanol; 1-[2-[2-chloro-4-(4-chlorophenoxy)phenyl]-2-methoxy-pent-3-ynyl]-1,2,4-triazole; 1-[2-[2-chloro-4-(4-chlorophenoxy)phenyl]-2-cyclopropyl-2-methoxy-ethyl]-1,2,4-triazole; 1-[2-[4-(4-chlorophenoxy)-2-(trifluoromethyl)phenyl]-2-methoxy-propyl]-1,2,4-triazole; 2-[2-chloro-4-(4-chlorophenoxy)phenyl]-3,3-dimethyl-1-(1,2,4-triazol-1-yl)butan-2-ol; 1-[2-[4-(4-chlorophenoxy)-2-(trifluoromethyl)phenyl]-2-cyclopropyl-2-methoxy-ethyl]-1,2,4-triazole; 1-[2-[2-chloro-4-(4-chlorophenoxy)phenyl]-2-methoxy-3,3-dimethyl-butyl]-1,2,4-triazole; 1-[2-[4-(4-chlorophenoxy)-2-(trifluoromethyl)phenyl]-2-methoxy-butyl]1,2,4-triazole; 2-[4-(4-chlorophenoxy)-2-(trifluoromethyl)phenyl]-1-(1,2,4-triazol-1-yl)pent-3-yn-2-ol; 1-[2-[4-(4-chlorophenoxy)-2-(trifluoromethyl)phenyl]-2-methoxy-pent-3-ynyl]-1,2,4-triazole; 2-[4-(4-chlorophenoxy)-2-(trifluoromethyl)phenyl]-1-(1,2,4-triazol-1-yl)but-3-yn-2-ol; 2-[2-chloro-4-(4-chlorophenoxy)phenyl]-1-(1,2,4-triazol-1-yl)propan-2-ol; 2-[2-chloro-4-(4-fluorophenoxy)phenyl]-1-(1,2,4-triazol-1-yl)propan-2-ol; 1-[2-[2-chloro-4-(4-chlorophenoxy)phenyl]-2-methoxy-propyl]-1,2,4-triazole; 1-[2-[2-chloro-4-(4-chlorophenoxy)phenyl]-2-methoxy-butyl]-1,2,4-triazole; 1-[2-[2-chloro-4-(4-chlorophenoxy)phenyl]-2-methoxy-pentyl]-1,2,4-triazole; 2-[2-chloro-4-(4-chlorophenoxy)phenyl]-1,1,1-trifluoro-3-(1,2,4-triazol-1-yl)propan-2-ol; 2-[2-chloro-4-(4-chlorophenoxy)phenyl]-3-fluoro-1-(1,2,4-triazol-1-yl)butan-2-ol hydrochloride; 2-[2-chloro-4-(4-chlorophenoxy)phenyl]-1-(1,2,4-triazol-1-yl)pent-4-yn-2-ol; 2-[2-chloro-4-(4-chlorophenoxy)phenyl]-1- methoxy-3-(1,2,4-triazol-1-yl)propan-2-ol; 2-[2-chloro-4-(4-fluorophenoxy)phenyl]-1-methoxy-3-(1,2,4-triazol-1-yl)propan-2-ol;

wherein compound I and compound II are present in a synergistically effective amount.

2. The mixture according to claim 1, comprising a compound I and a compound II in a weight ratio of from 100:1 to 1:100.

3. The mixture according to claim 1, wherein component 2) is selected from 1-[4-(4-chlorophenoxy)-2-(trifluoromethyl)phenyl]-1-cyclopropyl-2-(1,2,4-triazol-1-yl)ethanol, 2-[4-(4-chlorophenoxy)-2-(trifluoromethyl)phenyl]-3-methyl-1-(1,2,4-triazol-1-yl)butan-2-ol, 2-[4-(4-chlorophenoxy)-2-(trifluoromethyl)phenyl]-1-(1,2,4-triazol-1-yl)propan-2-ol, and 1-[2-chloro-4-(4-chlorophenoxy)phenyl]-1-cyclopropyl-2-(1,2,4-triazol-1-yl)ethanol.

4. The mixture according to claim 1, wherein component 1) and component 2) are present in a total weight ratio of from 100:1 to 1:100 wherein the total weight of component 2) is based on the amount of the solid material (dry matter) of component 2).

5. The mixture according to claim 1, wherein the at least one compound of formula I is selected from (Z,2E)-5-[1-(4-chlorophenyl)pyrazol-3-yl]oxy-2-methoxyimino-N,3-dimethyl-pent-3-enamide, (Z,2E)-5-[1-(2,4-difluorophenyl)pyrazol-3-yl]oxy-2-methoxy-imino-N,3-dimethyl-pent-3-enamide, (Z,2E)-5-[1-(2,4-dichlorophenyl)pyrazol-3-yl]oxy-2-methoxyimino-N,3-dimethyl-pent-3-enamide, (Z,2E)-5-[1-(2-chloro-4-methyl-phenyl)pyrazol-3-yl]oxy-2-methoxyimino-N,3-dimethyl-pent-3-enamide, (Z,2E)-2-methoxyimino-N,3-dimethyl-5-[1-(p-tolyl)pyrazol-3-yl]oxy-pent-3-enamide, (Z,2E)-5-[1-(2-methyl-4-fluoro-phenyl)pyrazol-3-yl]oxy-2-methoxyimino-N,3-dimethyl-pent-3-enamide, (Z,2E)-2-methoxyimino-N,3-dimethyl-5-[1-[4-(trifluoromethyl)phenyl]pyrazol-3-yl]oxy-pent-3-enamide, (Z,2E)-5-[1-(3,4-dichlorophenyl)pyrazol-3-yl]oxy-2-methoxyimino-N,3-dimethyl-pent-3-enamide, (Z,2E)-5-[1-(3,4-dimethylphenyl)pyrazol-3-yl]oxy-2-methoxyimino-N,3-dimethyl-pent-3-enamide, (Z,2E)-5-[1-(4-fluoro-3-methyl-phenyl)pyrazol-3-yl]oxy-2-methoxy-imino-N,3-dimethyl-pent-3-enamide, (Z,2E)-5-[1-(3-chloro-4-fluoro-phenyl)pyrazol-3-yl]oxy-2-methoxyimino-N,3-dimethyl-pent-3-enamide, (Z,2E)-5-[1-(3-fluoro-4-chloro-phenyl)pyrazol-3-yl]oxy-2-methoxyimino-N,3-dimethyl-pent-3-enamide, (Z,2E)-5-[1-(4-chloro-2-fluoro-phenyl)pyrazol-3-yl]oxy-2-methoxyimino-N,3-dimethyl-pent-3-enamide, (Z,2E)-5-[1-[4-(difluoromethoxy)phenyl]pyrazol-3-yl]oxy-2-methoxyimino-N,3-dimethyl-pent-3-enamide, (Z,2E)-5-[1-(3-cyclopropylphenyl)pyrazol-3-yl]oxy-2-methoxyimino-N,3-dimethyl-pent-3-enamide, (Z,2E)-5-[1-[4-chloro-3-(trifluoromethyl)phenyl]pyrazol-3-yl]oxy-2-methoxyimino-N,3-dimethyl-pent-3-enamide, (Z,2E)-2-methoxyimino-N,3-dimethyl-5-[1-(3,4,5-trifluoro-phenyl)pyrazol-3-yl]oxy-pent-3-enamide and (Z,2E)-2-methoxy-imino-N,3-dimethyl-5-[1-[4-(trifluoromethylsulfanyl)phenyl]pyrazol-3-yl]oxy-pent-3-enamide.

6. The mixture according to claim 5, wherein component 1) is selected from (Z,2E)-5-[1-(4-chlorophenyl)pyrazol-3-yl]oxy-2-methoxyimino-N,3-dimethyl-pent-3-enamide, (Z,2E)-5-[1-(2,4-dichlorophenyl)pyrazol-3-yl]oxy-2-methoxyimino-N,3-dimethyl-pent-3-enamide and (Z,2E)-5-[1-(4-chloro-2-fluoro-phenyl)pyrazol-3-yl]oxy-2-methoxyimino-N,3-dimethyl-pent-3-enamide.

7. An agrochemical composition, comprising a solvent or solid carrier and a mixture according to claim 1.

8. The composition according to claim 7 further comprising seed in an amount of from 1 g to 1000 g active components per 100 kg of seed.

9. A method for controlling phytopathogenic harmful fungi, comprising treating the fungi, their habitat or the seed, the soil or the plants to be protected against fungal attack with an effective amount of the mixture as defined in claim 1.

10. Plant propagation material coated with the mixture as defined in claim 1.

11. The method of claim 9, wherein the mixture comprises a compound I and a compound II in a weight ratio of from 100:1 to 1:100.

12. The method of claim 9, wherein component 2) is selected from 1-[4-(4-chlorophenoxy)-2-(trifluoromethyl)phenyl]-1-cyclopropyl-2-(1,2,4-triazol-1-yl)ethanol, 2-[4-(4-chlorophenoxy)-2-(trifluoromethyl)phenyl]-3-methyl-1-(1,2,4-triazol-1-yl)butan-2-ol, 2-[4-(4-chlorophenoxy)-2-(trifluoromethyl)phenyl]-1-(1,2,4-triazol-1-yl)propan-2-ol and 1-[2-chloro-4-(4-chlorophenoxy)phenyl]-1-cyclopropyl-2-(1,2,4-triazol-1-yl)ethanol.

13. The method of claim 9, wherein component 1) and component 2) are present in a total weight ratio of from 100:1 to 1:100 wherein the total weight of component 2) is based on the amount of the solid material (dry matter) of component 2).

14. The method of claim 9, wherein the at least one compound of formula I is selected from (Z,2E)-5-[1-(4-chlorophenyl)pyrazol-3-yl]oxy-2-methoxyimino-N,3-dimethyl-pent-3-enamide, (Z,2E)-5-[1-(2,4-difluorophenyl)pyrazol-3-yl]oxy-2-methoxyimino-N,3-dimethyl-pent-3-enamide, (Z,2E)-5-[1-(2,4-dichlorophenyl)pyrazol-3-yl]oxy-2-methoxyimino-N,3-dimethyl-pent-3-enamide, (Z,2E)-5-[1-(2-chloro-4-methyl-phenyl)pyrazol-3-yl]oxy-2-methoxyimino-N,3-dimethyl-pent-3-enamide, (Z,2E)-2-methoxyimino-N,3-dimethyl-5-[1-(p-tolyl)pyrazol-3-yl]oxy-pent-3-enamide, (Z,2E)-5-[1-(2-methyl-4-fluoro-phenyl)pyrazol-3-yl]oxy-2-methoxyimino-N,3-dimethyl-pent-3-enamide, (Z,2E)-2-methoxyimino-N,3-dimethyl-5-[1-[4-(trifluoromethyl)phenyl]pyrazol-3-yl]oxy-pent-3-enamide, (Z,2E)-5-[1-(3,4-dichlorophenyl)pyrazol-3-yl]oxy-2-methoxyimino-N,3-dimethyl-pent-3-enamide, (Z,2E)-5-[1-(3,4-dimethylphenyl)pyrazol-3-yl]oxy-2-methoxyimino-N,3-dimethyl-pent-3-enamide, (Z,2E)-5-[1-(4-fluoro-3-methyl-phenyl)pyrazol-3-yl]oxy-2-methoxy-imino-N,3-dimethyl-pent-3-enamide, (Z,2E)-5-[1-(3-chloro-4-fluoro-phenyl)pyrazol-3-yl]oxy-2-methoxyimino-N,3-dimethyl-pent-3-enamide, (Z,2E)-5-[1-(3-fluoro-4-chloro-phenyl)pyrazol-3-yl]oxy-2-methoxyimino-N,3-dimethyl-pent-3-enamide, (Z,2E)-5-[1-(4-chloro-2-fluoro-phenyl)pyrazol-3-yl]oxy-2-methoxyimino-N,3-dimethyl-pent-3-enamide, (Z,2E)-5-[1-[4-(difluoromethoxy)phenyl]pyrazol-3-yl]oxy-2-methoxyimino-N,3-dimethyl-pent-3-enamide, (Z,2E)-5-[1-(3-cyclopropylphenyl)pyrazol-3-yl]oxy-2-methoxyimino-N,3-dimethyl-pent-3-enamide, (Z,2E)-5-[1-[4-chloro-3-(trifluoromethyl)phenyl]pyrazol-3-yl]oxy-2-methoxyimino-N,3-dimethyl-pent-3-enamide, (Z,2E)-2-methoxyimino-N,3-dimethyl-5-[1-(3,4,5-trifluoro-phenyl)pyrazol-3-yl]oxy-pent-3-enamide and (Z,2E)-2-methoxy-imino-N,3-dimethyl-5-[1-[4-(trifluoromethylsulfanyl)phenyl]pyrazol-3-yl]oxy-pent-3-enamide.

15. The method of claim 14, wherein component 1) is selected from (Z,2E)-5-[1-(4-chlorophenyl)pyrazol-3-yl]oxy-2-methoxyimino-N,3-dimethyl-pent-3-enamide, (Z,2E)-5-[1-(2,4-dichlorophenyl)pyrazol-3-yl]oxy-2-methoxyimino-N,3-dimethyl-pent-3-enamide and (Z,2E)-5-

[1-(4-chloro-2-fluoro-phenyl)pyrazol-3-yl]oxy-2-methoxy-imino-N,3-dimethyl-pent-3-enamide.

\* \* \* \* \*